United States Patent
McCutchen-Maloney

(12) 
(10) Patent No.: US 6,365,355 B1
(45) Date of Patent: *Apr. 2, 2002

(54) CHIMERIC PROTEINS FOR DETECTION AND QUANTITATION OF DNA MUTATIONS, DNA SEQUENCE VARIATIONS, DNA DAMAGE AND DNA MISMATCHES

(75) Inventor: Sandra L. McCutchen-Maloney, Pleasanton, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/650,855

(22) Filed: Aug. 29, 2000

Related U.S. Application Data

(60) Provisional application No. 60/192,764, filed on Mar. 28, 2000.

(51) Int. Cl.[7] .......................... C12Q 1/68; G01N 33/53; C07K 1/00; C07H 21/04
(52) U.S. Cl. ............................ 435/6; 435/7.1; 530/350; 536/23.2; 536/23.4
(58) Field of Search ...................... 435/6, 7.1; 530/350; 536/23.2, 23.4

(56) References Cited

U.S. PATENT DOCUMENTS

| | | | |
|---|---|---|---|
| 5,567,627 A | 10/1996 | Lehnen | 436/518 |
| 5,683,877 A * | 11/1997 | Lu-Chang et al. | 435/6 |
| 5,702,894 A * | 12/1997 | Modrich et al. | 435/6 |
| 5,736,330 A | 4/1998 | Fulton | 435/6 |
| 5,750,335 A * | 5/1998 | Gifford | 435/6 |
| 5,830,707 A | 11/1998 | Bushman | 435/69.7 |
| 5,834,318 A | 11/1998 | Buettner | 436/518 |
| 5,871,992 A | 2/1999 | Teebor et al. | 435/199 |
| 5,905,025 A | 5/1999 | Marsolier et al. | 435/6 |
| 5,916,804 A | 6/1999 | Bushman | 435/325 |
| 5,919,623 A * | 7/1999 | Taylor | 435/6 |
| 5,922,855 A | 7/1999 | Liskay et al. | 536/23.5 |
| 5,948,627 A | 9/1999 | Lee | 435/7.24 |
| 6,008,031 A * | 12/1999 | Modrich et al. | 435/200 |
| 6,027,877 A * | 2/2000 | Wagner, Jr. | 435/6 |
| 6,110,684 A * | 8/2000 | Kemper et al. | 435/6 |

FOREIGN PATENT DOCUMENTS

| | | | |
|---|---|---|---|
| EP | 0-596 028 B1 * | 5/1994 | |
| JP | 10215897 | 8/1998 | C12Q/1/68 |
| WO | WO 95/14088 | 5/1995 | C12N/15/12 |
| WO | WO 98/17684 | 4/1998 | C12N/9/22 |
| WO | WO 98/46796 | 10/1998 | C12Q/1/68 |
| WO | WO 99/22029 | 5/1999 | C12Q/1/68 |
| WO | WO 99/36564 | 7/1999 | C12P/1/68 |

OTHER PUBLICATIONS

Lew, A., et al. "Affinity Selection of Polumerase Chain Reaction Products by DNA–Binding Proteins", Methods in Enzymology 218:526–534 (1993).

Wagner, R., et al., "Mutation detection Using Immobilized Mismatch Binding Protein (MutS)", Nucleic Acids Research 23:(19)3944–3948 (1995).

Wright, W., et al. "CASTing for multicomponent DNA–binding complexes", TIBS pp. 77–80 (1993).

* cited by examiner

*Primary Examiner*—Kenneth R. Horlick
(74) *Attorney, Agent, or Firm*—Alan H. Thompson

(57) ABSTRACT

Chimeric proteins having both DNA mutation binding activity and nuclease activity are synthesized by recombinant technology. The proteins are of the general formula A-L-B and B-L-A where A is a peptide having DNA mutation binding activity, L is a linker and B is a peptide having nuclease activity. The chimeric proteins are useful for detection and identification of DNA sequence variations including DNA mutations (including DNA damage and mismatches) by binding to the DNA mutation and cutting the DNA once the DNA mutation is detected.

64 Claims, 1 Drawing Sheet

CHIMERIC PROTEINS FOR DETECTION AND QUANTITATION OF DNA MUTATIONS, DNA SEQUENCE VARIATIONS, DNA DAMAGE AND DNA MISMATCHES

RELATED APPLICATION

This application claims the benefit under 35 U.S.C. § 119(e) of U.S. provisional patent application No. 60/192,764, filed Mar. 28, 2000, which is hereby incorporated by reference in its entirety. This application is also related to co-pending application Ser. No. 09/651,656 entitled DETECTION AND QUANTITATION OF SINGLE NUCLEOTIDE POLYMORPHISMS, DNA SEQUENCE VARIATIONS, DNA MUTATIONS. DNA DAMAGE AND DNA MISMATCHES filed Aug. 29, 2000 and which is hereby incorporated by reference in its entirety.

The United States Government has rights in this invention pursuant to Contract No. W-7405-ENG-48 between the U.S. Department of Energy and the University of California for the operation of Lawrence Livermore National Laboratory.

FIELD OF THE INVENTION

The present invention relates to the field of molecular biology, and more particularly, detection of DNA sequence variation, DNA mutations, DNA damage and DNA base pair mismatches. In particular, the invention relates to proteins including chimeric proteins capable of detecting DNA sequence variations, DNA mutations, damaged DNA or DNA with mismatched base pairs.

BACKGROUND OF THE INVENTION

Natural DNA sequence variation exists in identical genomic regions of DNA among individual members of a species. It is of interest to identify similarities and differences in such genomic regions of DNA because such information can help identify sequences involved in susceptibility to disease states as well as provide genetic information for characterization and analysis of genetic material.

When a cell undergoes reproduction, its DNA molecules are replicated and precise copies are passed on to its descendants. The linear base sequence of a DNA molecule is maintained during replication by complementary DNA base pairing. Occasionally, an incorrect base pairing does occur during DNA replication, which, after further replication of the new strand, results in a double-stranded DNA offspring with a sequence containing a heritable single base difference from that of the parent DNA molecule. Such heritable changes are called "genetic polymorphisms, genetic mutations," "single base pair mutations," "point mutations" or simply, "DNA mismatches". In addition to random mutations during DNA replication, organisms are constantly bombarded by endogenous and exogenous genotoxic agents which injure or damage DNA. Such DNA damage or injury can result in the formation of DNA mismatches or DNA mutations such as insertions or deletions.

The consequences of natural DNA sequence variation, DNA mutations, DNA mismatches and DNA damage range from negligible to lethal, depending on the location and effect of the sequence change in relation to the genetic information encoded by the DNA. In some instances, natural DNA sequence variation, DNA mutations, DNA mismatches and DNA damage can lead to cancer and other diseases of which early detection is critical for treatment.

There is thus a tremendous need to be able to rapidly identify differences in DNA sequences among individuals. In addition there is a need to identify DNA mutations, DNA mismatches and DNA damage to provide for early detection of cancer and other diseases.

SUMMARY OF THE INVENTION

The present invention concerns the use of proteins that function biologically to recognize DNA mutations and their application in defined systems for detecting and mapping DNA mutations, DNA mismatches and DNA damage. The present invention provides methods for using such DNA mutation recognition proteins, alone or in combination with other proteins, for detecting DNA sequence variability, detecting and localizing DNA mutations and for comparing DNA sequences among individuals of a species.

In one embodiment, the present invention is directed to chimeric proteins where the chimeric protein includes a DNA mutation binding protein, a linker and a nuclease.

The DNA mutation binding proteins of the chimeric proteins of the invention will bind to genetic mutations, single base pair mutations, point mutations, DNA mismatches, DNA insertions, DNA deletions, DNA transversions, DNA transitions, frameshift mutations, damaged DNA, and other changes or alterations in a normal or wild type DNA sequence.

DNA mutation binding proteins which find use in the invention include human MutS homologue2 (hMSH2), xeroderma pigmentosum complementation group A (XPA), xeroderma pigmentosum C (XPC), xeroderma pigmentosum complementation group E (XPE), *Thermus thermophilus* Mut S (TthMutS), thymine DNA glycosylase (TDG), *Escherechia coli* Fpapy-DNA glycosylase, *Escherechia coli* endonuclease III, *Escherechia coli* exonuclease III, *Escherechia coli* endonuclease IV, T4 endonuclease, *Escherechia coli* uracil DNA glycosylase, *Escherachia coli* A/G-specific adenine DNA glycosylase (MutY), *Escherechia coli* Uvr A DNA mutation binding protein, *Escherechia coli* Uvr B DNA mutation binding protein and other DNA damage binding proteins.

The DNA mutation binding proteins of the invention include those proteins having amino acid sequences depicted in SEQ ID NO:1, 3, 7, 9, 11, 15, 19, 21, 23, 25, 29, 31, 39, 35, 37, 101 and 103. The DNA mutation binding proteins of the invention are encoded by DNA which have the nucleotide sequences depicted in SEQ ID NO:2, 4, 8, 10, 12, 16, 20, 22, 24, 26, 30, 32, 40, 36, 38, 102 and 104.

The nucleases of the chimeric proteins of the invention are proteins and peptides capable of cleaving or cutting DNA. Nucleases include the N-terminus of human excision repair cross-complementing rodent repair deficiency (XPF), *Serratia marcescens* nuclease (Nuc), *Escherechia coli* Fpapy-DNA glycosylase; *Escherechia coli* endonuclease III; *Escherechia coli* endonuclease IV; T4 endonuclease; *Escherechia coli* uracil DNA glycosylase; *Escherechia coli* A/G-specific adenine DNA glycosylase, *Escherechia coli* Uvr B nuclease, *Escherechia coli* Uvr C nuclease and other DNA nucleases.

The nucleases include those proteins having amino acids depicted in SEQ ID NO:5, 11, 13, 25, 31, 35, 37, 39, 103 and 105. The nucleases are encoded by DNA having the nucleotide sequences depicted in SEQ ID NO 6, 12, 14, 26, 31, 36, 38, 40, 104 and 106.

In one embodiment, the chimeric proteins of the invention are recombinant proteins having the formula A-L-B or B-L-A, wherein: A is a peptide having DNA mutation binding activity; L is a linker peptide; and B is a peptide having nuclease activity. The invention is further directed to DNA encoding the chimeric proteins of the invention. The DNA may be in a vector. Furthermore, the vector may be in a suitable host such as bacteria, yeast or fungi.

In another embodiment, the present invention is directed to an isolated and purified chimeric protein comprising a pair of proteins wherein the pair of proteins are selected from the group consisting of XPF and XPA, XPF and hMSH2, XPA and XPF, hMSH2 and XPF, Nuc and hMSH2, Nuc and XPA, MutS and XPF, XPF and MutS, Nuc and MutS, XPA and XPF, and Nuc and XPA, wherein XPF is human excision repair cross-complementing rodent repair deficiency, XPA is xeroderma pigmentosum complementation group A, hMSH2 is human MutS homologue2, Nuc is *Serratia marcescens* nuclease and TthMutS is *Thermus thermophilus* Mut S.

The linker peptide of the chimeric peptide of the invention generally consists of 8 amino acids rich in glycine and proline or other amino acids known to disrupt protein secondary structure. For example, the sequence GSGPSPGS (SEQ ID NO:17) finds use in the invention. However, in some circumstances the linker peptides will be as short as zero amino acids where the nuclease and DNA binding protein retain activity in the absence of a linker peptide. In other circumstances the peptide will have up to 5, 6, 7, 8 9 10, 11–15, 16–20 or 21–30 amino acids.

In another embodiment, the present invention is directed to an isolated and purified nucleic acid encoding a chimeric polypeptide comprising a DNA mutation binding protein and a nuclease. The nucleic acid may by in a nucleic acid construct. The nucleic acid construct may be operably associated with an expression control sequence functional in a microbial cell such as a bacterial cell.

In another embodiment, the present invention is directed to a recombinant bacterial cell comprising a nucleic acid encoding a chimeric polypeptide comprising a DNA mutation binding protein and a nuclease.

In another embodiment, the present invention is directed to an isolated and purified nucleic acid encoding a chimeric protein having the formula A-L-B or B-L-A, wherein:A is a peptide having DNA mutation binding activity; L is a linker peptide; and B is a peptide having nuclease activity.

In another embodiment, the present invention is directed to a method of detecting a DNA sequence variation, comprising: a) obtaining a polynucleotide; b) obtaining a chimeric protein wherein the chimeric protein has a DNA mutation binding region and nuclease region wherein the DNA binding region recognizes DNA mutations; c) forming a mixture of the polynucleotide and the chimeric protein; d) forming a reacted sample by incubating the mixture under conditions wherein if the polynucleotide includes mutated DNA, the DNA damage protein binds to said mutated DNA and the nuclease cuts said mutated DNA; and e) analyzing the reacted sample to determine the extent of cleavage of the polynucleotide.

The DNA sequence variation may be a DNA mutation.

BRIEF DESCRIPTION OF THE SEQUENCE LISTING

Figure 1:
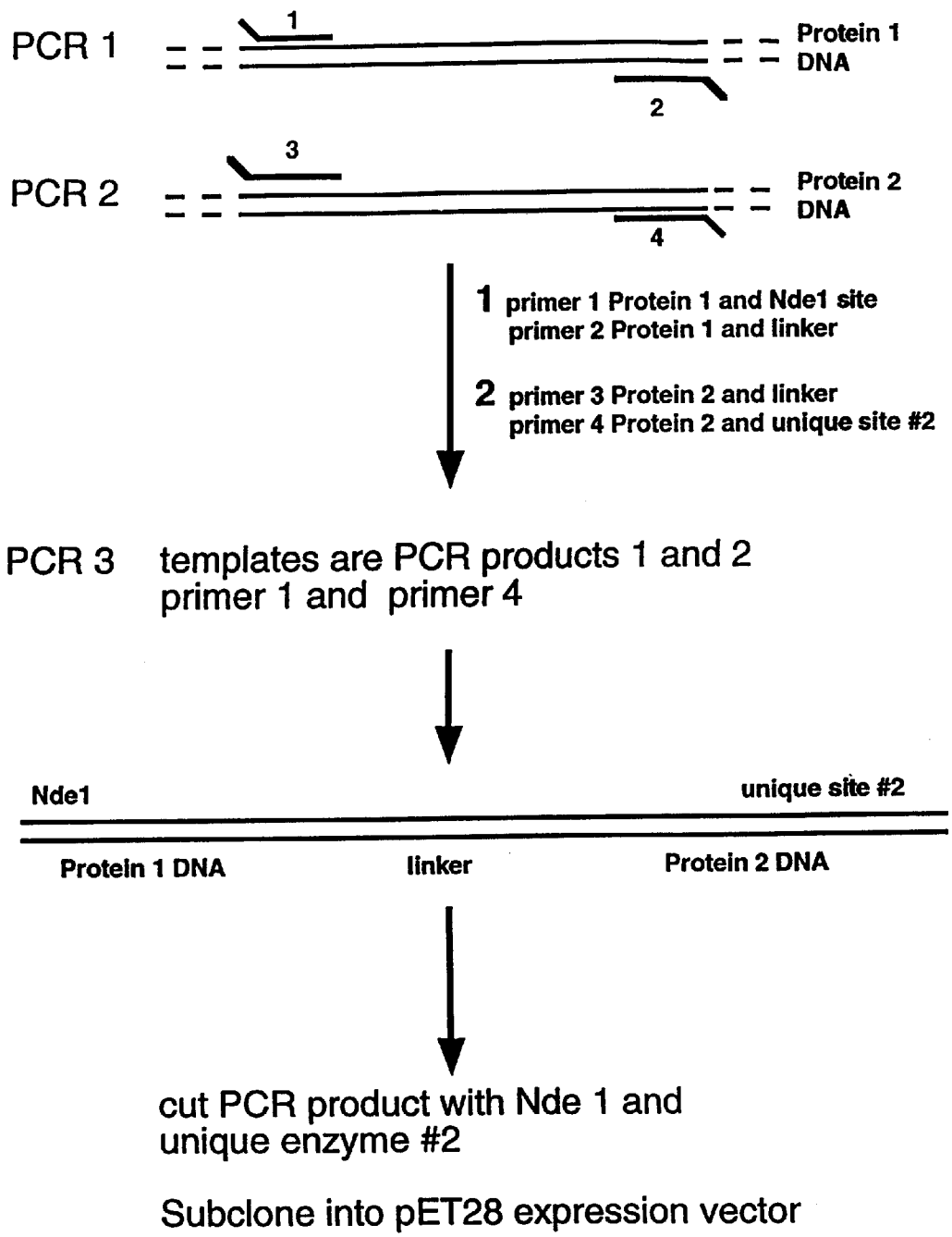
FIG. 1 shows a schematic diagram of the overlap extension PCR methodology utilized to produce the chimeric proteins of the invention.

SEQ ID NO:1 shows amino acids 637–877 of human Mut S homologue 2, hMSH2 which is the active fragment of hMSH2.

SEQ ID NO:2 shows the DNA sequence encoding amino acids 637–877 of hMSH2 which is the active fragment of hMSH2.

SEQ ID NO:3 shows the protein sequence of the full-length hMSH2 polypeptide.

SEQ ID NO:4 shows the DNA sequence encoding the full-length hMSH2.

SEQ ID NO:5 shows the full length protein sequence of the *Serratia marcescens* nuclease (Nuc).

SEQ ID NO:6 shows the DNA sequence of the full-length *Serratia marcescens* nuclease (Nuc).

SEQ ID NO:7 shows the protein sequence of the human xeroderma pigmentosum, complementation group A (XPA).

SEQ ID NO:8 shows the DNA sequence of the human xeroderma pigmentosum, complementation group A (XPA).

SEQ ID NO:9 shows amino acids 98–219 of human XPA which is the active fragment of human XPA.

SEQ ID NO:10 shows the DNA sequence encoding amino acids 98–219 of human XPA which is the active fragment of human XPA.

SEQ ID NO:11 shows amino acids 12–378 of human excision repair cross-complementing rodent repair deficiency, complementation group 4 protein (XPF, also referred to as ERCC4) which is the active fragment of XPF.

SEQ ID NO:12 shows the DNA sequence encoding amino acids 12–378 of human excision repair cross-complementing rodent repair deficiency, complementation group 4 (XPF, also referred to as ERCC4) which is the active fragment of XPF.

SEQ ID NO:13 shows the full length protein sequence of human excision repair cross-complementing rodent repair deficiency, complementation group 4 (XPF).

SEQ ID NO:14 shows the DNA sequence encoding the full-length human excision repair cross-complementing rodent repair deficiency, complementation group 4 (XPF, also referred to as ERCC4).

SEQ ID NO:15 shows the protein sequence of the *Thermus thermophilus* MutS DNA mutation binding protein.

SEQ ID NO:16 shows the DNA sequence encoding the *Thermus thermophilus* mutS gene DNA mutation binding protein.

SEQ ID NO:17 shows a synthetic linker peptide sequence.

SEQ ID NO:18 shows the DNA sequence encoding a synthetic peptide linker.

SEQ ID NO:19 shows the protein sequence of human xeroderma pigmentosum, complementation group C (XPC).

SEQ ID NO:20 shows the DNA sequence encoding human xeroderma pigmentosum, complementation group C (XPC).

SEQ ID NO:21 shows the protein sequence of the human xeroderma pigmentosum group E, UV-damaged binding factor, XPE.

SEQ ID NO:22 shows the DNA sequence encoding the human xeroderma pigmentosum group E, UV-damaged binding factor, XPE.

SEQ ID NO:23 shows the protein sequence of *Escherechia coli* Fapy-DNA glycosylase, Fpg.

SEQ ID NO:24 shows the DNA sequence encoding the *Escherechia coli* fpg gene for Fapy-DNA glycosylase, Fpg.

SEQ ID NO:25 shows the protein sequence of *Escherechia coli* endonuclease III, Endo III.

SEQ ID NO:26 shows the DNA sequence of the *Escherechia coli* nth gene encoding endonuclease III, Endo III.

SEQ ID NO:27 shows the protein sequence of *Escherechia coli* endonuclease VIII, Endo VIII.

SEQ ID NO:28 shows the DNA sequence encoding the *Escherechia coli* endonuclease VIII, Endo VIII.

SEQ ID NO:29 shows the protein sequence of the *Escherechia coli* exonuclease III, Exo III.

SEQ ID NO:30 shows the DNA sequence of *Escherechia coli* xthA gene encoding exonuclease III, Exo III.

SEQ ID NO:31 shows the protein sequence of the *Escherechia coli* endonuclease IV, Endo IV.

SEQ ID NO:32 shows the DNA sequence of *Escherechia coli* nfo gene encoding endonuclease IV, Endo IV.

SEQ ID NO:33 shows the protein sequence for a synthetic T4 endonuclease V, T4 endo.

SEQ ID NO:34 shows the DNA sequence for a synthetic T4 endonuclease V (T4endV) gene, T4 endo V.

SEQ ID NO:35 shows the protein sequence of the *Escherechia coli* uracil DNA glycosylase, ung.

SEQ ID NO:36 shows the DNA sequence of the *Escherechia coli* ung gene encoding uracil DNA glycosylase, ung.

SEQ ID NO:37 shows the protein sequence of *Escherechia coli* (strain K-12) A/G-specific adenine glycosylase, MutY.

SEQ ID NO:38 shows the DNA sequence of *Escherechia coli* (strain K-12) A/G-specific adenine glycosylase (micA) gene, MutY.

SEQ ID NO:39 shows the protein sequence of a synthetic T4 endonuclease, T4 endo.

SEQ ID NO:40 shows the DNA sequence of a synthetic T4 endonuclease (T4endV) gene, T4 endo.

SEQ ID NO:41 shows the protein sequence of a thymine DNA-glycosylase (TDG).

SEQ ID NO:42 shows the DNA sequence of a thymine DNA-glycosylase (TDG).

SEQ ID NO:43–44 show PCR primers for amplification of XPF at the N-terminus.

SEQ ID NO,45–46 show PCR primers for amplification of XPF at the C-terminus.

SEQ ID NO:47–48 show PCR primers for the amplification of the XPA domain at the N-terminus.

SEQ ID NO:49–50 show PCR primers for the amplification of the XPA domain at the C-terminus.

SEQ ID NO:51–52 show PCR primers for the amplification of the hMSH2 domain at the N-terminus.

SEQ ID NO:53–54 show PCR primers for the amplification of the hMSH2 domain at the C-terminus.

SEQ ID NO:55–56 show PCR primers for the amplification of Nuc at the N-terminus.

SEQ ID NO:57–58 show PCR primers used to amplify the XPF-XPA cDNA chimera.

SEQ ID NO:59–60 show PCR primers used to amplify the XPF-hMSH2 cDNA chimera.

SEQ ID NO:61–62 show PCR primers used to amplify the XPA-XPF cDNA chimera.

SEQ ID NO:63–64 show the PCR primers used to amplify the hMSH2-XPF cDNA chimera.

SEQ ID NO:65–66 show the PCR primers used to amplify Nuc-hMSH2 cDNA chimera.

SEQ ID NO:67–68 show the PCR primers used to amplify the Nuc-XPA cDNA chimera.

SEQ ID NO:69–70 show PCR primers for amplification of MutS at the N-terminus.

SEQ ID NO:71–72 show PCR primers for amplification of MutS at the C-terminus.

SEQ ID NO:73–74 show PCR primers for amplification of Nuc at the N-terminus.

SEQ ID NO:75–76 show PCR primers for the amplification of the XPF domain at the N-terminus.

SEQ ID NO:77–78 show PCR primers for the amplification of XPF domain at the C-terminus.

SEQ ID NO:79–80 show the PCR primers used to amplify the MutS-XPF cDNA chimera.

SEQ ID NO:81–82 show the PCR primers used to amplify the XPF-MutS cDNA chimera.

SEQ ID NO:83–84 show the PCR primers used to amplify the Nuc-MutS cDNA chimera.

SEQ ID NO:85–86 show PCR primers used to amplify XPA at the N-terminus.

SEQ ID NO:87–88 show the PCR primers used to amplify XPA at the C-terminus.

SEQ ID NO:89–90 show the PCR primers used to amplify Nuc at the N-terminus.

SEQ ID NO:91–92 show the PCR primers used to amplify XPF at the N-terminus.

SEQ ID NO:93–94 show the PCR primers used to amplify XPF at the C-terminus.

SEQ ID NO:95–96 show the PCR primers used to amplify the XPA-XPF cDNA chimera.

SEQ ID NO:97–98 show the PCR primers used to amplify the XPF-XPA cDNA chimera.

SEQ ID NO:99–100 show the PCR primers used to amplify the Nuc-XPA cDNA chimera.

SEQ ID NO:101 shows the protein sequence of *Escherechia coli* Uvr A DNA-binding protein.

SEQ ID NO:102 shows the DNA sequence of the *Escherechia coli* UVr A DNA-binding protein gene.

SEQ ID NO:103 shows the protein sequence of *Escherechia coli* Uvr B nuclease and damage recognition protein.

SEQ ID NO:104 shows the DNA sequence of the *Escherechia coli* UVr B nuclease and damage recognition protein gene.

SEQ ID NO:105 shows the protein sequence of *Escherechia coli* Uvr C nuclease.

SEQ ID NO:106 shows the DNA sequence of the *Escherechia coli* UVr C nuclease.

DETAILED DESCRIPTION OF THE INVENTION

In order to more completely understand the invention, the following definitions are provided.

DNA Sequence Variability: DNA Sequence Variability is the DNA sequence variation between one DNA sequence and a second DNA sequence. Either the first or the second DNA sequence may be a reference or control sequence such as a wild type sequence. DNA sequence variability is the differences in the DNA sequence between the reference or control sequence and another sequence of interest.

Two DNA sequences of interest may be compared by hybridization under conditions which permit base pairing between the two strands. Differences in the two sequences result in mismatches or mutations in hybrid.

DNA Mutation: A DNA mutation is a change in a DNA sequence from a normal or wildtype sequence to a mutated or different sequence resulting in mutated DNA. DNA mutations include DNA sequence variability, genetic mutations, single base pair mutations, point mutations, DNA mismatches, DNA insertions, DNA deletions, DNA transversions, DNA transitions, frameshift mutations, damaged DNA, and other changes or alterations in a normal or wild type DNA sequence.

DNA Transition: A DNA transition is a change in a DNA sequence involving the substitution of one purine or pyrimidine for the other (e.g., adenine for guanine, cytosine for thymidine or vice versa).

DNA Transversion: A DNA transversion is a change in a DNA sequence in which a purine is substituted for a pyrimide or vice versa (e.g., adenine for cytosine or thymidine, guanine for cytosine or thymidine or vice versa).

DNA Insertion: A DNA insertion is the addition of 1, 2, 3 or more nucleotides in a strand of a DNA double helix.

DNA Deletion: A DNA deletion mutation is the deletion or removal of 1, 2, 3 or more nucleotides in a strand of a DNA double helix.

Frameshift Mutations: Frameshift mutations are DNA insertions or DNA deletions which effect the translation of the DNA sequence to the encoded amino acid sequence because of the insertion or deletion of particular nucleotides.

DNA Mismatches: A DNA mismatch can include an insertion or a deletion but also refers to a DNA sequence with incorrect base pairing resulting from an error during replication. The normal base pairings are A-T and C-G. Examples of mismatches include A-C, A-G, A-A, T-C, T-G, T-T, C-C, and G-G where "A" represents adenine, "G" represents guanine, "C" represents cytosine and "T" represents thymidine.

Damaged DNA: The individual nucleotides of a DNA sequence can be altered in their chemistry or sequence thus resulting in damaged DNA. By this definition (from "DNA Repair and Mutageneis" by E. C. Friedberg, G. C. Walker and W. Siede, ASM Press, Washington, D.C. 1995, which is hereby incorporated by reference), all the other definitions provided here fall under DNA damage which can be subclassified into spontaneous damage or environmentally induced damage. Examples of damaged DNA include: mismatches, tautomeric shifts, deaminated bases, uracil incorporated DNA, lost bases also known as depurinated or depyrimidinated DNA, oxidatively and radically induced damaged DNA, ionization (UV) induced damaged DNA, and chemically induced damaged DNA (induced by alkylating agents, cross linking agents, psoralens, metabolites such as heterocyclic amines, N-2-acetyl-2-aminofluorene, benzopyrene, aflatoxins, N-methyl-N-nitro-N-nitrosoguanidine, and 4-nitroquinoline-1-oxide).

DNA Mutation Binding Proteins: DNA mutation binding proteins are proteins and peptides capable of detecting differences in DNA sequences including DNA mutations and binding to such mutated DNA. Such DNA mutation binding proteins include human MutS homologue2 (hMSH2), xeroderma pigmentosum complementation group A (XPA), xeroderma pigmentosum C (XPC), xeroderma pigmentosum complementation group E (XPE), *Thermus thermophilus* Mut S (TthMutS), thymine DNA glycosylase (TDG), *Escherechia coli* Fpapy-DNA glycosylase, *Escherechia coli* endonuclease III, *Escherechia coli* exonuclease III, *Escherechia coli* endonuclease IV, T4 endonuclease, *Escherechia coli* uracil DNA glycosylase, *Escherechia coli* A/G-specific adenine DNA glycosylase (MutY), *Escherechia coli* Uvr A, *Escherechia coli* Uvr and other DNA damage binding proteins.

Nucleases: Nucleases are proteins and peptides capable of cleaving or cutting DNA. Nucleases include the N-terminus of human excision repair cross-complementing rodent repair deficiency (XPF), *Serratia marcescens* nuclease (Nuc), *Escherechia coli* Fpapy-DNA glycosylase; *Escherechia coli* endonuclease III; *Escherechia coli* endonuclease IV; T4 endonuclease; *Escherechia coli* uracil DNA glycosylase; *Escherechia coli* A/G-specific adenine DNA glycosylase, *Escherechia coli* Uvr B, *Escherechia coli* Uvr C and other DNA nucleases.

Chimeric Proteins: A chimeric protein is a fusion or linkage of two or more different peptides. Generally, the linked peptides are joined or linked by a linker peptide. Chimeric proteins generally have all or a substantial portion of a first polypeptide linked at the amino(N-) or carboxy (C-) terminus to all or a portion of a second polypeptide. The term "chimeric protein" as used herein refers to a C-terminal to N-terminal fusion of a first protein and a second protein where one of the proteins generally a DNA mutation binding protein and the other protein is generally a nuclease. The fusion proteins of the present invention include constructs in which the C-terminal portion of the first protein is fused to the N-terminal portion of the second and also constructs in which the C-terminal portion of the second protein is fused to the N-terminal portion of the first protein. More specifically, in this invention each DNA mutation binding protein and each nuclease can be placed at either the N- or C-terminus of the chimera.

Chimeric cDNA: Chimeric cDNA refers to the cDNA encoding the chimeric proteins of the invention.

Linker Peptide: Linker peptides are short peptides which link two peptides in a chimeric protein. Linker peptides generally have random coil structures. Linker peptides are designed to maintain the activity of the two linked peptides. In particular, the linker peptide of this invention is designed so as not to interrupt the normal fold of the nuclease or the DNA binding domains DNA damage binding protein of the proteins forming the chimera. Linker peptides can consist of any amino acid in a variety of combinations of various lengths. A preferred linker consists of eight amino acids rich in glycine and proline. Glycine and proline residues are utilized because they are known to disrupt protein secondary structure. Disruption of protein secondary structure in a chimera serves to keep the proteins active while maintaining the peptides at a short distance from each other. This separation of the two peptides helps ensure correct folding of the individual proteins as well as the retention of native function.

Recombinant: Recombinant means to be produced by recombinant DNA technology.

Taking into account these definitions, the present invention concerns chimeric proteins that recognize differences in DNA sequences including mutated DNA and their use in defined systems for identifying, detecting and mapping DNA sequence variations, DNA mutations including DNA mismatches and DNA damage.

A. Chimeric Proteins

The present invention is directed to chimeric proteins having DNA binding activity and nuclease activity wherein the DNA binding activity recognizes damaged DNA. In one embodiment, the present invention is directed to chimeric proteins having sequences presented by the formulae:

A-L-B and B-L-A wherein A is a peptide having DNA mutation binding activity and capable of binding to mutated DNA, B is a peptide having nuclease activity and L is a linker peptide. The chimeric proteins are linked in such a manner as to produce a single protein which retains the biological activity of both A and B.

1. DNA Mutation Binding Proteins (A)

DNA mutation binding proteins are proteins and peptides capable of detecting DNA mutations and binding to such mutated DNA. Such DNA mutation binding proteins which find use in the chimeric proteins of the invention include but are not limited to the following proteins:

Human Mut S homolog 2 (hMSH-2) functions in mismatch repair, has ATPase activity and recognizes primarily G-T mismatches. It is useful for DNA mismatch recognition.

Human Xeroderma pigmentosum (XPA) functions in nucleotide excision repair. The protein primarily recognizes UV induced DNA damage. The protein is useful for DNA damage recognition.

Human Xeroderma pigmentosum (XPC) functions in nucleotide excision repair. The protein primarily recognizes UV induced DNA damage and is useful for DNA damage recognition.

Human Xeroderma pigmentosum (XPE) functions in nucleotide excision repair. The protein primarily recognizes UV induced DNA damage and is useful for DNA damage recognition.

*Thermus thermophilus* Mut S (TthMuts) is a thermostabile (heat stable) protein which functions in mismatch repair. This protein recognizes all mismatches. It is useful for mismatch recognition. It is particularly useful in the invention because of its thermostability and ability to recognize all mismatches and potentially DNA damage.

*Mehtanococcus thermoautotropicum* (TDG) is a thermostabile protein which recognizes T/G mismatches. This protein is particularly useful because of its DNA mismatch recognition and thermostability.

*Escherechia coli* Fapy-DNA glycosylase recognizes DNA damage by oxidative injury. *Escherechia coil* endonuclease III recognizes primarily apurinic (abasic) sites. *Escherechia coli* endonuclease IV also recognizes primarily apurinic (abasic) sites. *Escherechia coli* T4 endonuclease recognizes pyrimidine dimers (UV damage). *Escherechia coli* uracil DNA glycosylase recognizes uracil containing DNA. *Escherechia coli* A/G-specific adenine DNA glycosylase (MutY) recognizes G/A mismatches.

Some of the DNA mutation binding proteins also have nuclease activity. In those circumstances, the DNA mutation binding proteins may be useful alone without the additional nuclease in the chimera. Alternatively, if the DNA binding domain for the DNA mutation binding protein is known, that portion may be attached to a nuclease to form a chimera.

2. Nucleases: (B)

Nucleases are proteins capable of cleaving or cutting DNA. Nucleases which find use in the chimeric proteins of the invention include but are not limited to the following proteins.

The N-terminus of XPF functions in nucleotide excision repair in complex with ERCC1 and XPA to repair various forms of DNA damage. The N-terminus of XPF contains an endonuclease function and thus functions in the chimeras to cut DNA. The N-terminus of XPF appears to be nonspecific and can cut both double and single stranded DNA.

*Serratia marcescens* nuclease (Nuc) is a very stable, nonspecific nuclease that serves a protective role in *S. marcescens*. In the chimeras, this nuclease functions to cut DNA.

*Escherechia coli* Fapy-DNA glycosylase functions in the excision of 8-oxoguanine and formamidopyrimidines. This enzyme removes these nucleotides and leaves a gap in the DNA sequence.

*Escherechia coli* endonuclease III is an endonuclease that functions to repair DNA damaged by radiation, oxidation and UV light.

*Escherechia coli* exonuclease III functions to repair abasic sites, and DNA damaged by oxidation and alkylation.

*Escherechia coli* endonuclease IV functions to repair abasic sites, and DNA damaged by oxidation and alkylation.

*Escherechia coli* T4 endonuclease repairs UV damaged DNA by removing the damaged base.

*Escherechia coli* uracil DNA glycosylase removed deaminated cytosine or uracil from DNA.

*Escherechia coli* A/G-specific adenine DNA glycosylase cuts at G/A mismatches and oxidative damage.

*Escherechia coli* TDG cuts at G/T mismatches and deaminated cytosine or uracil.

3. Linker Peptides: (L)

Linker peptides are short peptides with random coil structures used to link two peptides or proteins in the chimeric proteins of the invention. Linker peptides are designed to maintain the activity and native folded structure of the two linked peptides or proteins. In particular, the linker peptides of this invention are designed so as not to interrupt the tertiary structure of the nucleases or the DNA binding domains of the DNA binding proteins. The length of the linker is not critical so long as the peptides retain their activity in the chimera. The linker peptide generally consists of 8 amino acids rich in glycine and proline or other amino acids, known to disrupt protein secondary structure. For example, the sequence GSGPSPGS (SEQ ID NO:17) finds use in the invention. However, in some circumstances the linker peptides will be as short as zero amino acids where the nuclease and DNA binding protein retain activity in the absence of a linker peptide. In other circumstances the peptide will have up to 5, 6, 7, 8 9 10, 11–15, 16–20 or 21–30 amino acids.

B. Polypeptide Variants

In addition to the full length sequences described above, various functional domains or fragments for proteins such as XPF, XPA and hMSH-2 have been identified and find use in the chimeric proteins of the invention. These functional domains or fragments are included in the full length sequences. Such functional domains include amino acid sequences 637–877 of hMSH2 depicted in SEQ ID NO:1; amino acid sequences 98–219 of XPA depicted in SEQ ID NO: 9; amino acid sequences 12–378 of XPF depicted in SEQ ID NO: 11. These functional domains can be used in the chimeric proteins of the invention. Use of functional domains simplifies protein expression and purification. The functional domains are generally more stable in vitro than the longer full length proteins.

The present invention also includes the use of modified proteins having amino acid sequences similar to those of the native or wild type proteins described herein, but into which modifications are naturally provided (e.g., allelic variations in the nucleotide sequence which may result in amino acid changes in the polypeptides) or deliberately engineered modifications. Such modifications in the sequences may include the replacement, insertion or deletion of one or more amino acid residues in the coding sequence. For example, the modified protein may contain one or more additional amino acids at one or both ends of the polypeptide chain; may have an amino acid sequence which differs from that of the naturally-occurring protein; or may be an active fragment or domain of the naturally-occurring protein as discussed above. The term "substantially identical," is used herein to encompass such potential modifications, and specifically herein means that a particular subject sequence, for example, a mutant sequence, varies from the native sequence by one or more substitutions, deletions, or additions, the net effect of which is to retain biological activity of the protein when derived as a chimeric fusion protein. Generally the modified proteins will have at least 80% of the activity of the unmodified protein. However, in some circumstances the activity of the modified protein will be higher than the native or wild type protein.

As illustrative modifications of the proteins of this invention, one acidic amino acid, such as aspartic acid, may be substituted for another acidic amino acid such as glutamic acid; or a basic amino acid, such as lysine, arginine or histidine may be substituted for another basic amino acid; or a non-polar amino acid, such as alanine, glycine, leucine or isoleucine may be substituted for another non-polar amino acid.

C. Formation of Chimeric Proteins

The chimeric proteins of the invention are produced by recombinant technology. As a first step, a chimeric cDNA is produced by linking two cDNA's by overlap extension PCR methodology as described in Innis, M. A. et al. (1990) *PCR Protocols: A Guide to Methods and Applications*, Academic Press, San Diego, Calif. and as detailed in the Example section below. Four PCR primers are required to produce each chimeric cDNA as illustrated in FIG. 1. In the first PCR reaction, primer 1 amplifies the N-terminal coding region of the first protein while incorporating an Nde I restriction site and primer 2 amplifies the C-terminal coding region of the first protein while incorporating half of the linker. In a second PCR reaction, primer 3 amplifies the N-terminal coding region of the second protein while incorporating the other half of the linker and primer 4 amplifies the C-terminal coding region of the second protein while incorporating a second unique restriction site. A third PCR reaction uses the products of the first two PCR reactions as a template and the end primers 1 and 4 to produce the chimeric cDNA PCR product.

The full length chimeric cDNA PCR products are digested at unique restriction sites and subcloned into a suitable vector such as the pET28 or pET31 expression vector available from Novagen. Once cloned into a suitable cloning vector, the chimeric protein may be produced in large quantities in a host for the vector. Specific examples of chimeric protein synthesis are illustrated in the Example section below.

D. Purification of Proteins

In most circumstances, it will be desirable to purify the chimeric proteins or variants thereof. The pET28, pET31 or other suitable expression vector containing the chimeric cDNA of interest is grown in bacteria under conditions suitable to express the chimeric protein in large quantities. The chimeric proteins are then purified from the host cell. Protein purification techniques are well known to those of skill in the art. These techniques involve, at one level, the crude fractionation of the host cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. A particularly efficient method of purifying peptides is fast protein liquid chromatography (FPLC) or even HPLC.

Various techniques suitable for use in protein purification will be well known to those of skill in the art. These include, for example, precipitation with ammonium sulphate, polyethylene glycol (PEG), antibodies and the like or by heat denaturation, followed by centrifugation; chromatography such as ion exchange, gel filtration, reverse phase, hydroxylapatite and, affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified chimeric protein or peptide.

In one embodiment, the chimeric proteins of the invention are expressed with an N-terminal His-tag (Histidine tag). Expression conditions are optimized for soluble expression of the chimeric protein. Nickel affinity chromatography can be used for purification of the chimeric proteins using the affinity of the His-tag for metal ions.

There is no general requirement that the chimeric proteins always be provided in their most purified state. Indeed, it is contemplated that less substantially purified products will have utility in certain embodiments. Partial purification may be accomplished by using fewer purification steps in combination, or by utilizing different forms of the same general purification scheme.

E. Detection and Quantitation

Electrophoresis assays and other procedures well known to those of skill in the art of molecular biology can readily be used to detect differences in DNA sequences including DNA mutations, DNA damage and DNA mismatches using the chimeric proteins of the invention. Electrophoresis assays can be readily used to separate and distinguish DNA molecules on the basis of size and charge. Such procedures are well known in the art as described in Sambrook, et al. *Molecular Cloning A Laboratory Manual* 2nd Ed. (1989) Cold Spring Harbor Laboratory Press, which is hereby incorporated by reference.

In this invention, the chimeric proteins are utilized to detect DNA sequence variations or DNA mutations and cleave at sites of DNA damage or mismatch. The activity of the chimeric peptides is monitored by an in vitro gel assay utilizing genomic DNA, plasmid DNA or synthetic oligonucleotides with known quantities of DNA damage or mismatches as controls. The chimeras are incubated with the various forms of DNA and a comparison is made between the cleavage of damaged DNA, mismatched DNA and double stranded DNA to DNA with no damage or mismatches. The chimeras, by their ability to detect damage and mismatches, preferentially cleave the damaged and mismatched DNA.

Damaged or mismatched DNA useful as control molecules in the invention are available from commercial sources such as Operon Technologies, Alameda, Calif. 94501. Examples of damaged DNA used in the invention include an abasic site and a thymine-thymine dimer (both naturally occurring) as well as a cholesterol adduct (commonly used to mimic DNA damage in vivo). Phip adducts, heterocylic amines that form as a result of carcinogenic metabolites, are also used in the invention. In addition, all possible DNA mismatch combinations can be utilized. For example, a 40 base pair oligonucleotides are synthesized with the desired DNA damage or mismatches in the center of one strand of DNA.

Other control DNA molecules include genomic and plasmid DNA available from commercial sources such as Sigma Pharmaceuticals, which may be treated with UV light to induce thymine-thymine dimers and 6-4 photoproducts.

F. Analysis of DNA Sequence Variability

The chimeric proteins of the invention are useful for analysis of DNA sequence variability. In one embodiment, a specific DNA sequence is chosen as a control sequence. This control sequence is also known as a reference or wildtype sequence. Other DNA sequences are compared to the control sequence and are known as sample DNA sequences. The control sequence may be supplied as a single stranded or double stranded sequence. The DNA sample to be analyzed may be supplied as a single stranded or double stranded sequence. The control and sample DNAs are then incubated under conditions to permit annealing of complementary strands to form a control/sample DNA hybrid. The control/sample DNA hybrid is then incubated with the chimeric proteins of the invention. If there is a difference between the control and sample DNA sequences, there will be a DNA mutation in the hybrid DNA. Such DNA mutation may simply be normal genetic variation between different sequences. As such the chimeric proteins of the invention find use in measuring or detecting genome sequence variations.

G. Use of Chimeric Proteins for Disease Detection

The chimeric proteins of the invention are useful for identifying mutations involved in diseases. Such diseases are characterized by DNA mutations. Exemplary diseases include without limitation, diseases such as cystic fibrosis, generalized myotonia and myotonia congenita, hyperkalemic periodic paralysis, hereditary ovalocytosis, hereditary spherocytosis and glucose malabsorption; which are associated with mutations in the genes encoding ion transporters; multiple endocrine neoplasia, which is associated with mutations in the MEN2a, b, and MEN1 genes; familial medullary thyroid carcinoma, and Hirschsprung's disease, which are associated with mutations in the ret proto-oncogene; familial hypercholesterolemia, which is associated with mutations in the LDL receptor gene; neurofibromatosis and tuberous sclerosis, which are associated with mutations in the NF1 gene and NF type 2 gene; breast and ovarian cancer, which are associated with mutations in the BRCA1, BRCA2, BRCA3 genes; familial adenomatous polyposis, which is associated with mutations in the APC gene; severe combined immunodeficiency, which is associated with mutations in the adenosine deaminase gene; xeroderma pigmentosum, which is associated with mutations in the XPAC gene; Cockayne's syndrome, which is associated with mutations in the ERCC6 excision repair gene; fragile X, which is associated with mutations in the fmrI gene; Duchenne's muscular dystrophy, which is associated with mutations in the Duchenne muscular dystrophy gene; myotonic dystrophy, which is associated with mutations in the myotonic dystrophy protein kinase gene; bulbar muscular dystrophy, which is associated with mutations in the androgen receptor genes; Huntington's disease, which is associated with mutations in the Huntington's gene; Peutz-jegher's syndrome; Lesch-Nyhan syndrome, which is associated with mutations in the HPRT gene; Tay-Sachs disease, which is associated with mutations in the HEXA gene; congenital adrenal hyperplasia, which is associated with mutations in the steroid 21-hydroxylase gene; primary hypertension, which is associated with mutations in the angiotensin gene; hereditary non-polyposis, which is associated with mutations in the hNMLH1 gene; colorectal carcinoma, which is associated with mutations in the 2 mismatch repair genes; colorectal cancer, which is associated with mutations in the APC gene; forms of Alzheimer's disease which have been associated with the apolipoprotein E gene, retinoblastoma, which is associated with mutations in the Rb gene; Li-Fraumeui syndrome, which is associated with mutations in the p53 gene; various malignancies and diseases that are associated with translocations: e.g., in the bcr/abl, bcl-2 gene; chromosomes 11 to 14 and chromosomes 15 to 17 transpositions.

The invention having been fully described is now exemplified by the following non-limiting examples.

EXAMPLES

General

Illustrative of the invention, the following chimeras were isolated and purified.

| Chimera # | Chimera |
|---|---|
| 1 | XPF (fragment)-linker-XPA (fragment) |
| 2 | XPF (fragment)-linker-hMSH2 (fragment) |
| 3 | XPA (fragment)-linker-XPF (fragment) |
| 4 | hMSH2 (fragment)-linker-XPF (fragment) |
| 5 | Nuc (full)-linker-hMSH2 (fragment) |
| 6 | Nuc (full)-linker-XPA (fragment) |
| 7 | MutS (full)-linker-XPF (fragment) |
| 8 | XPF (fragment)-linker-MutS (full) |
| 9 | Nuc (full)-linker-MutS (full) |
| 10 | XPA (full)-linker-XPF (fragment) |
| 11 | XPF (fragment)-linker-XPA (full) |
| 12 | Nuc (full)-linker-XPA (full) |

The linker peptides all had the following acid sequence: GSGPSPGS (SEQ ID NO:17). The various components of the chimeras are identified as either "full" or "fragment" where "full" refers to the full length peptide and "fragment" refers to an active fragment or functional domain of the full length peptide. The active fragment of XPF is amino acids 12–378 (SPQ ID NO: 11) of the full length peptide. The active fragment of XPA is amino acids 98–219 (SEQ ID NO: 9) of the full length peptide. The active fragment of hMSH2 is amino acids 637–877 (SEQ ID NO: 1) of the full length peptide.

The chimeric peptides are produced by recombinant technology as detailed in FIG. 1. As a first step, a chimeric cDNA is produced by linking two cDNAs by overlap PCR extension technology. The primers used to produce the chimeric cDNA's are identified by the region of the peptide encoded by cDNA. For example, chimera #1 includes XPF at the N-terminus of the chimeric peptide and XPA at the C-terminus of the chimeric peptide. In contrast, chimera 3 includes XPA (fragment) at the N-terminus and XPF at the C-terminus of the chimeric peptide.

Example 1

Synthesis of Chimeras 1–6
a) XPF, XPA, hMSH-2 and Nuc

The cDNA's for chimeras 1–6 were synthesized in a multistep PCR procedure. As a first step, XPF at the C and N termini, XPA at the C and N termini, hMSH2 at the C and N termini and Nuc at the N-terminus were synthesized by PCR.

For the PCR reactions, 100 ng cDNA template was used for each reaction. XPA and XPF were cloned at Lawrence Livermore National Laboratory (LLNL) Livermore, Calif. U.S.A. Bot. The XPF cDNA template and the XPA cDNA template are available from LLNL. The hMSH2 cDNA template is available from Dr. Adrian Whitehouse, St. James University, UK. The nuc cDNA template is available from Dr. Michael Benedik, Baylor College of Medicine, Tex., U.S.A. The PCR reactions contained a pair of primers with 100 pmol of each primer, 100 µM each dNTP, 10 µl 10× buffer (final concentration 20 mM Tris-HCl, 50 mM KCl, 2 mM MgCl$_2$, pH 8.4) and 100 mg cDNA. One µl of Taq polymerase enzyme was used. The reaction volume was brought to 100 µl with water. The PCR conditions were as follows: 94° C. for 3 minutes; 94° C., 1 min; 50° C., 1 min; and 72° C. for 3 minutes. The cycle was repeated 25 times and the final product stored at 4° C. Gibco Platinum Taq polymerase was utilized. The dNTPs were obtained from Perkin Elmer.

The primer pairs as outlined below were utilized to produce the indicated portion of the cDNA chimera. Each primer pair was utilized in a PCR reaction with the corresponding cDNA as a template. For example, for XPF at the N-terminus, the XPF cDNA template was utilized with primers having sequences depicted as SEQ ID NO:43 and 44 as indicated below to produce the XPF at the N-terminus PCR product using the PCR conditions outlined above.

(1) XPF (fragment) at N-terminus ctc cat atg gcg ccg ctg ctg gag (SEQ ID NO: 43)

act acc agg act agg acc act acc gtt gct ttc tag gac cag (SEQ ID NO: 44)

(2) XPF (fragment) at C-terminus ggt agt ggt cct agt cct ggt agt atg gcg ccg ctg ctg gag (SEQ ID NO: 45)

ctc gag ctc tca gtt gct ttc tag gac cag (SEQ ID NO: 46)

(3) XPA (fragment) at N-terminus ctc cat atg gaa ttt gat tat gta ata tgc g (SEQ ID NO: 47)

act acc agg act agg acc act acc aaa ttt ctt ctg ttt cat ttt ttc tcg g (SEQ ID NO: 48)

(4) XPA (fragment) at C-terminus ggt agt ggt cct agt cct ggt agt atg gaa ttt gat tat gta ata tgc g (SEQ ID NO: 49)

ctc gag ctc tca aaa ttt ctt ctg ttt cat ftt ttc tcg g (SEQ ID NO: 50)

(5) hMSH2 (fragment) at N-terminus ctc cat atg tcc agg cat gct tgt gtt g (SEQ ID NO: 51)

act acc agg act agg acc act acc tct ttc cag ata gca ctt c (SEQ ID NO: 52)

(6) hMSH2 (fragment) at C-terminus ggt agt ggt cct agt cct ggt agt tcc agg cat gct tgt gtt g (SEQ ID NO: 53)

ctc gag ctc tca tct ttc cag ata gca ctt c (SEQ ID NO: 54)

(7) Nuc at N-terminus ctc cca tgg gct tta aca aca aga tgt tgg cct tgg ccg cc (SEQ ID NO: 55)

act acc agg act agg acc act acc gtt ttt gca gcc cat caa ctc cgg (SEQ ID NO: 56)

b) Synthesis of Chimeras 1–6

The PCR reaction products from Example 1 a) above were utilized as templates for final PCR reactions to produce chimeric cDNAs 1–6. These PCR reaction products can be mixed and matched in various combinations in subsequent PCR reactions to produce various cDNA chimeras in addition to those explicitly exemplified.

For chimera 1, the PCR reaction products XPF at the N-terminus and XPA at the C-terminus were utilized as template in the final PCR reaction.

For chimera 2, the PCR reaction products XPF at the N-terminus and hMSH2 at the C-terminus were utilized as template in the final PCR reaction.

For chimera 3, the PCR reaction product XPA at the N-terminus and XPF at the C-terminus were utilized as template in the final PCR reaction.

For chimera 4, the PCR reaction product hMSH2 at the N-terminus and XPF at the C-terminus were utilized as template in the final PCR reaction.

For chimera 5, the PCR reaction products Nuc at the N-terminus and hMSH2 at the C-terminus were utilized as template in the final PCR reaction.

For chimera 6, the PCR reaction products Nuc at the N-terminus and and XPA at the C-terminus were utilized as template in the final PCR reaction.

The PCR reaction components and conditions were as follows.

Each final PCR reaction contained 100 ng PCR of reaction product template from Example 1a) as indicated above, 100 pmol of each primer as indicated below, 100 µM each dNTP, 10 µl 10× buffer (final concentration 20 mM Tris-HCl, 50 mM KCl, 2 mM MgCl$_2$, pH 8.4. One µl of Taq polymerase enzyme was used. The reaction volume was brought to 100 µl with water. The PCR conditions were as follows: 94° C. for 3 minutes; 94° C., 1 min; 50° C., 1 min; and 72° C. for 3 minutes. The cycle was repeated 30 times and the final product stored at 4° C. Gibco Platinum Taq polymerase was utilized. The dNTPs were obtained from Perkin Elmer.

The primers for the final PCR reactions were as follows:

(1) Chimera 1: XPF (fragment)-linker-XPA (fragment)

ctc cat atg gcg ccg ctg (SEQ ID NO: 57)

ctc gag ctc tca aaa ttt c (SEQ ID NO: 58)

(2) Chimera 2: XPF (fragment)-linker-hMSH2 (fragment)

ctc cat atg gcg ccg ctg (SEQ ID NO: 59)

ctc gag ctc tca tct ttc (SEQ ID NO: 60)

(3) Chimera 3: XPA (fragment)-linker-XPF (fragment)

ctc cat atg gaa ttt gat (SEQ ID NO:61)

ctc gag ctc tca gtt gct (SEQ ID NO:62)

(4) Chimera 4: hMSH2 (fragment)-linker-XPF (fragment)

ctc cat atg tcc agg cat (SEQ ID NO: 63)

ctc gag ctc tca gtt gct (SEQ ID NO: 64)

(5) Chimera 5: Nuc-linker-hMSH2 (fragment)

ctc cca tgg gct tta aca (SEQ ID NO:65)

ctc gag ctc tca tct ttc (SEQ ID NO: 66)

(6) Chimera 6: Nuc-linker-XPA (fragment)

ctc cca tgg gct tta aca (SEQ ID NO: 67)

ctc gag ctc tca aaa ttt c (SEQ ID NO: 68)

The PCR reaction products were purified by gel electrophoresis and subcloned into plasmids as described in Example 4 below.

Example 2

Synthesis of Chimeras 7–9 a) MutS, XPF Domain and Nuc

The cDNAs for chimeras 7–9 were synthesized in a multistep PCR procedure. As a first step, MutS at the N-terminus, MutS at the C-terminus, XPF domain at the N- and C-termini and Nuc at the N-terminus were synthesized. For the PCR reactions, 100 ng cDNA template was used for each reaction. The MutS cDNA template is available from Dr. Adrian Whitehouse, St. James University, UK. The XPF cDNA template is available from LLNL. The nuc cDNA template is available from Dr. Michael Benedik, Baylor College of Medicine, Tex. Each PCR reaction contained a pair of PCR primers 100 pmol of each primer indicated below, 100 µM each dNTP, 10 µl 10× buffer (final concentration 20 mM Tris-HCl, 50 mM KCl, 2 mM MgCl$_2$, pH 8.4) and 100 ng of cDNA template. One µl of Taq polymerase enzyme was used in the reaction. The reaction volume was brought to 100 µl with water. The PCR conditions were as follows: 94° C. for 5 minutes; 94° C. for 1 min; 60° C. for 1 min; and 72° C. for 1.5 minutes. The cycle was repeated 30 times and the final product stored at 4° C. Gibco Platinum Taq polymerase was utilized. The dNTPs were obtained from Perkin Elmer.

The primer pairs as outlined below were utilized in the PCR reactions. Each primer pair was utilized in a PCR reaction with the corresponding cDNA as a template. For example, for MutS at the N-terminus, the MutS cDNA template was utilized with the primers depicted below having been assigned SEQ ID NO:69 and 70 in a PCR reaction to produce the MutS at the N-terminus PCR product.

(1) MutS at N-terminus ctc cat atg ggg ggg tat ggc gga gtt aag (SEQ ID NO:69)

act acc agg act agg acc act acc ccc ctt cat gct acc cag ggg gag (SEQ ID NO:70)

(2) MutS at C-terminus ggt agt ggt cct agt cct ggt agt atg ggg ggg tat ggc gga gtt aag (SEQ ID NO:71)

ctc gtc gac tca ccc ctt cat gct acc cag ggg (SEQ ID NO:72)

(3) Nuc at N-terminus ctc cat atg cgc ttt aac aac aag atg ttg gcc ttg gcc gcc (SEQ ID NO:73)

act acc agg act agg acc act acc gtt ttt gca gcc cat caa ctc cgg (SEQ ID NO: 74)

(4) XPF (fragment) at N-terminus ctc cat atg gcg ccg ctg ctg gag (SEQ ID NO: 75)

ggt agt ggt cct agt cct ggt agt gtt gct ttc tag gac cag (SEQ ID NO:76)

(5) XPF (fragment) at C-terminus act acc agg act agg acc act acc atg gcg ccg ctg ctg gag (SEQ ID NO: 77)

ctc gtc gac tca gtt gct ttc tag gac cag (SEQ ID NO: 78)

b) Synthesis of Chimeras 7–9

The PCR reaction products from Example 2 a) above were utilized as template for a final PCR reaction to produce chimeric cDNAs 7–9. These PCR reaction products can be mixed and matched in various combinations in subsequent PCR reactions to produce various cDNA chimeras in addition to those exemplified herein.

For chimera 7, the PCR reaction products MutS at the N-terminus and XPF domain at the C-terminus were utilized as template in a final PCR reaction.

For chimera 8, the PCR reaction products XPF domain at the N-terminus and MutS at the C-terminus were utilized as template in a final PCR reaction.

For chimera 9, the PCR reaction products Nuc at the N-terminus and MutS at the C-terminus were utilized in a final PCR reaction.

Each final PCR reaction contained 100 ng of PCR product template from Example 2a) as indicated above and 100 pmol of each primer as indicated below. Each reaction contained 100 µM for each dNTP from Perkin Elmer, 10 µl 10× buffer (final concentration 20 mM Tris-HCl, 50 mM KCl, 2 mM MgCl$_2$, pH 8.4). One µl Taq polymerase was utilized. The reaction volume was brought to 100 µl with water. The PCR conditions were as follows: 94° C. for 1 minute; 94° C. for 30 seconds and 68° C. for 3 minutes. This reaction cycle was repeated for 30 repetitions. After completion of the 30 repetitions, the reaction was run at 68° C. for 3 minutes followed by 15 minutes at 15° C. Finally, the reaction products were stored at 4° C. A Clontech Advantage PCR kit was utilized along with the Klen Taq polymerase.

Chimera 7: MutS-linker-XPF (fragment)

ctc cat atg ggg ggg tat ggc gga gtt aag (SEQ ID NO: 79)

ctc gtc gac tca gtt gct ttc tag gac cag ttc c (SEQ ID NO: 80)

Chimera 8: XPF (fragment)-linker-MutS ctc cat atg gcg ccg ctg ctg gag tac (SEQ ID NO: 81)

ctc gtc gac tca ccc ctt cat gct acc cag ggg (SEQ ID NO: 82)

Chimera 9: Nuc-linker-MutS ctc cat atg cgc ttt aac aac aag atg ttg gcc ttg gcc gcc c (SEQ ID NO: 83)

ctc gtc gac tca ccc ctt cat gct acc cag ggg (SEQ ID NO: 84)

Example 3

Synthesis of Chimeras 10–12 a) XPA, Nuc and XPF

The cDNAs for chimeras 10–12 were synthesized in a multistep PCR procedure. As a first step, XPA at the C and N termini, XPF at the C and N termini and Nuc at the N-terminus were synthesized.

One hundred (100) ng cDNA template was used for each PCR reaction. XPF was cloned at LLNL and the cDNA is available from LLVL. XPA was cloned at LLNL and the cDNA is available from LLNL. The nuc cDNA template is available from Dr. Michael Benedik, Baylor College of Medicine, Tex. Each PCR reaction contained 100 pmol of each primer indicated below, 100 µM each dNTP (from Perkin Elmer) 10 µl 10× buffer (final concentration 20 mM tris-HCl, 50 mM KCl, 2 mM MgCl$_2$, pH 8.4) and 100 ng cDNA templete. One µl Taq polymerase including 2 mM MgCl$_2$ was utilized in the PCR reaction. The reaction volume was brought to 100 µl with water. The PCR reaction conditions were as follows: 94° C. for 3 minutes; 94° C. for 1 minute, 60° C. for 1 minute and 72° C. for 3 minutes repeated 30 times. The reaction products were stored at 4° C. Gibco Platinum Taq Polymerase was utilized.

The following primer pairs were utilized in the PCR reactions. Each primer pair was utilized in a PCR reaction with the corresponding cDNA as a template. For example, for XPA at the N-terminus, the XPA cDNA template was utilized with the primers depicted below having been assigned SEQ ID NO:'s 85 and 86.

(1) XPA at N-terminus ctc cat atg gcg gcg gcc gac g (SEQ ID NO:85)

act acc agg act agg acc act acc gtt cat ggc cac aca tag tac aag (SEQ ID NO:86)

(2) XPA at C-terminus ggt agt ggt cct agt cct ggt agt atg gcg gcg gcc gac g (SEQ ID NO 87)

ctc gag ctc tca gtt cat ggc cac aca tag tac aag (SEQ ID NO:88)

(3) Nuc at N-terminus ctc cat atg cgc ttt aac aac aag atg ttg gcc ttg gcc gcc (SEQ ID NO:89)

act acc agg act agg acc act acc gtt ttt gca gcc cat caa ctc cgg (SEQ ID NO:90)

(4) XPF (fragment) at N-terminus ctc cat atg gcg ccg ctg ctg gag (SEQ ID NO:91)

ggt agt ggt cct agt cct ggt agt gtt gct ttc tag gac cag (SEQ ID NO:92)

(5) XPF (fragment) at C-terminus act acc agg act agg acc act acc atg gcg ccg ctg ctg gag (SEQ ID NO:93)

ctc gag ctc tca gtt gct ttc tag gac cag (SEQ ID NO:94)

b) Synthesis of Chimeras 10–12

The PCR reaction products from Example 3a) above were utilized as template for a final PCR reaction to product chimeric cDNAs 10–12. These PCR reaction products can be mixed and matched in various combinations in subsequent PCR reactions to produce various cDNA chimeras in addition to those specifically exemplified herein.

For chimera 10, the PCR reaction products XPA at the N-terminus and XPF at the C-terminus were utilized as template in a final PCR reaction.

For chimera 11, the PCR reaction products XPF at the N-terminus and XPA at the C-terminus were utilized as a template in a final PCR reaction.

For chimera 12, the PCR reaction products XPF at the N-terminus and XPA at the C-terminus were utilized as a template in a final PCR reaction.

Each final PCR reaction contained 100 ng of PCR reaction product template from Example 3a) as indicated above and 100 pmol of each primer as indicated below. Each reaction contained 100 $\mu$M each dNTP from Perkin Elmer and 10 $\mu$l 10× buffer (final concentration 20 mM Tris-HCl, 50 mM KCl, 2 mM $MgCl_2$ pH 8.4) and 100 ng of PCR reaction product. One $\mu$l Taq polymerase in 2 mM $MgCl_2$ was utilized. The reaction volume was brought to 100 $\mu$l with water.

The PCR reaction conditions were as follows: 94° C. for 1 minute followed by 94° C. for 30 seconds and 68° C. for 3 minutes. This cycle was repeated 30 times. Next, the reaction was heated for 68° C. for 3 minutes followed by 15 minutes at 15° C. The reaction products were stored at 4° C. A Clontech Advantage PCR kit was utilized.

Chimera 10: XPA (full)-linker-XPF (fragment)

ctc cat atg gcg gcg gcc gac g (SEQ ID NO:95)

ctc gag ctc tca gtt gct ttc tag gac cag ttc c (SEQ ID NO:96)

Chimera 11: XPF (fragment)-linker-XPA (full)

ctc cat atg gcg ccg ctg ctg gag tac (SEQ ID NO:97)

ctc gag ctc tca gtt cat ggc cac aca tag tac aag (SEQ ID NO:98)

Chimera 12: Nuc-linker-XPA (full)

ctc cat atg cgc ttt aac aac aag atg ttg (SEQ ID NO:99)

ctc gag ctc tca gtt cat ggc cac aca tag tac aag (SEQ ID NO:100)

Example 4

Chimeric Protein Synthesis

The chimeric cDNAs from Examples 1–4 were purified by gel electrophoresis and cloned into plasmids. Chimeras 1–4 were cut with Nde I and Sac I for subcloning. Chimeras 5–6 were cut with Nco I and Sac I for subdloning. Chimeras 8–9 were cut with Nde I and Sal I for subcloning. Chimeras 10–12 were cut with Nde I and Sac I for subdoning. Chimeric cDNAs 1–4 and 7–12 were subdioned into pET 28 available from Novagen. Chimeric cDNAs 5–6 were subcloned into pET 31 available from Novagen. The pET 28 and pET 31 chimeric expression constructs were transformed into BL21 (DE3) cells for amplification. After plating on selection media, colonies were picked and grown up in 2 liters Luria broth (LB) media+kanamycin (30 $\mu$g/ml) at 25° C. at 125 rpm overnight. The cultures were induced with 0.3 mM isopropyl-$\beta$-D-galactopyranoside IPTG when the optical density of the cultures reached 0.6–1.0 at 600 nm to induce synthesis of the chimeric protein from the cloned cDNA. At induction, the speed of the shaker was in crease d to 225 rpm. The cultured cells were harvested after 4 hours of growth by centrifugation. The pellets were then frozen at −80° C.

Example 5

Chimeric Protein Purification

The pellets from example 4 were thawed on ice and resuspended in 200 ml of HepA buffer (20 mM Tris, 0.5 mM DTT, 0.5 mM EDTA, 100 mM NaCl, 10% glycerol, pH 7.5). One ml of 1 mg/ml lysozyme and 2 ml of 20% Triton X-100 were added to the resuspended pellet to form a resuspended pellet mixture. The resuspended pellet mixture was left on ice for 30 minutes until the cell suspension became viscous. After the 30 minute period, the suspension was sonicated for 4×30 seconds. The sonicated mixture was then centrifuged for 30 minues at 11–13K rpm. The pellet was resuspended in HepA buffer+6M urea and rocked overnight at 4° C. to solubilize the proteins.

After the overnight incubation, the solubilized mixture was centrifuged for 30 minutes at 11–13K rpm. The supernatant was collected and 200 ml of HepA buffer (pH 7.5) was added to reduce the urea concentration to 3M. The mixture was then filtered and run on a 5 ml heparin column (Pharmacia) on a Pharmacia GradiTrac Protein Purification system at 4° C. Proteins were separated on a 200 ml gradient from 100% HepA/0% HepB (HepA with 1 M NaCl) to 0% HepA/100% HepB. Five ml fractions were collected. Purity was assessed by SDS-PAGE. The purest fractions were pooled and stored frozen at −80° C. for storage.

The approximate molecular weights of the various purified chimeric proteins was as follows:

| Chimera | Approximate Molecular Weight |
| --- | --- |
| Chi 1-XPF (fragment)-linker-XPA (fragment) | 54 kDa |
| Chi 2-XPF (fragment)-linker-hMSH2 (fragment) | 68 kDa |
| Chi 3-XPA (fragment)-linker-XPF (fragment) | 54 kDa |
| Chi 4-hMSH2 (fragment)-linker-XPF (fragment) | 68 kDa |
| Chi 5-Nuc (full)-linker-hMSH2 (fragment) | 57.5 kDa |
| Chi 6-Nuc (full)-linker-XPA (fragment) | 43.6 kDa |
| Chi 7-MutS (full)-linker-XPF (fragment) | 130 kDa |
| Chi 8-XPF (fragment)-linker-MutS (full) | 130 kDa |
| Chi 9-Nuc (full)-linker-MutS (full) | 120 kDa |
| Chi 10-XPA (full)-linker-XPF (fragment) | 72 kDa |
| Chi 11-XPF (fragment)-linker-XPA (full) | 72 kDa |
| Chi 12-Nuc (full)-linker-XPA (full) | 61 kDa |

Example 6

Further Protein Purification

The chimeric proteins may be further purified, if desired. However, in most instances, the partially purified chimeras work sufficiently well in the assays the invention to not require further purification. Useful purification columns include NTA (nickle affinity columns) Q and SP ion exchange columns, all available from Pharmacia.

For further protein purification, the purest fractions from Example 5 are pooled. Next, 2.5× volumes of water are added to reduce the salt concentration. Next, 1.7× volumes of buffer A for the selected column (as detailed below) are added. The pH of the protein solution is then adjusted appropriately for each column.

The buffers utilized in the purification protocols are outlined below:

NTA A (20 mM Tris, 200 mM NaCl, 5 mM BME, 10% glycerol, pH 7.5)

NTA B (NTA A with 500 mM imidazole)

Q A (20 mM Tris, 1 mM DTT, 100 mM NaCl, 10% glycerol, pH 8.5)

Q B (Q A with 1M NaCl)

SP A (20 mM MES, 1 mM DTT, 100 mM NaCl, 10% glycerol, pH 6.5)

SP B (SP A with 1 M NaCl)

Example 7

1. Assaying Chimeras for Activity for Damage Detection

A standard assay for cleavage of supercoiled plasmid or genomic DNA was used to test purified chimeric proteins for endonuclease activity. The plasmid or genomic DNA was either undamaged (as supplied) or damaged for 30 minutes with a UV light source (using a Model UVGL-25 hand held UV lamp, 115 volts, 0.16 amps from UVP, Upland, Calif.) to induce DNA mutations.

The reaction mix contained 1 µg DNA in reaction buffer (20 mM Tris-HCl, pH 8.0, 20 mM NaCl, 5 mM $MgCl_2$, 1 mM DTT, 5% glycerol, and 50 µg/mL acetylated bovine serum albumin). Reactions were initiated by the addition of chimeras in the range of 10–200 ng in a total volume of 20 µL. Chimera 6 (Nuc-XPA) and Chimera 4 (MSH-XPF) were utilized. Following incubation for 2 h at 37° C., SDS was added to a final concentration of 0.5% and incubated for an additional 30 min at 37° C. to disrupt protein-DNA complexes. To visualize digestion products, samples were subjected to electrophoresis on a 1% agarose gel, stained for several min in 2 µg/mL ethidium bromide and destained in water. As a blank, reaction buffer was added in place of the protein sample.

The results showed that the chimeras cleave more UV damaged DNA than undamaged DNA indicating that the DNA mutation binding protein is recognizing and binding to the UV light damaged DNA and the nuclease is cutting that DNA. Uncut DNA (no chimera added) shows supercoiled DNA. Damaged DNA is cut by the nuclease of the chimera and was identified as nicked and linear DNA on the gel.

2. Assaying Chimeras for Activity in Mismatch Detection

A standard assy for cleavage of 50 base pair double-stranded oligos containing various mismatches (ordered from Operon, Alameda, Calif.) were used to test purified chimeric proteins for endonuclease activity. The 50 base pair DNA substrate contained a perfect matching complimentary strand or the following mismatches centered within the oligo: G/A, G/G, G/T, C/A, C/T, C/C, A/A, or T/T.

The reaction mix contained 50 pmol DNA in reaction buffer (20 mM Tris-CHl, pH 8.0, 200 mM NaCl, 5 mM $MgCl_2$, 1 mM DTT, 5% glycerol, and 50 µg/mL acetylated bovine serum albumin). Reactions were initiated by the addition of chimeras in the range of 10–50 ng in a total volume of 20 µl. Data for Chimera 9 (Nuc-MutS) is shown using 50 ng protein/reaction. Following incubation for 30 m at 40° C., SDS was added to a final concentration of 0.5% and incubated for an additional 30 min at 37° C. to disrupt protein-DNA complexes. To visualize digestion products, samples were subjected to electrophoresis on a 2.5% agarose gel, stained for several minutes in 2 µg/mL ethidium bromide and destained in water. As a blank, reaction buffer was added in place of the protein sample.

The results showed that Chimera 9 cleaves all mismatched DNA substrates but does not cleave the perfect match indicating that the DNA mutation binding protein (MutS) is recognizing and binding to the mismatches afterwhich the nuclease can cleave the DNA. Uncut or blank DNA samples for each substrate (no chimera added) show linear 50 mer. Mismatched DNA is cut by the nuclease of the chimera which is visualized by less intensity of the DNA band and a smearing of the DNA.

What is claimed is:

1. A recombinant chimeric protein comprising a DNA mutation binding protein and a nuclease.

2. The chimeric protein of claim 1 wherein said DNA mutation is selected from the group consisting of DNA sequence variability, single base pair mutations, uracil incorporated DNA, point mutations, DNA mismatches, DNA insertions, DNA deletions, DNA transversions, DNA transitions, frameshift mutations and damaged DNA.

3. The chimeric protein of claim 2 wherein said DNA mutation is a DNA mismatch.

4. The chimeric protein of claim 2 wherein said DNA mutation is a DNA insertion.

5. The chimeric protein of claim 1 wherein said nuclease nonspecifcally cuts DNA.

6. The chimeric protein of claim 1 wherein said nuclease cuts DNA at 7-oxoguanine residues or DNA at guanine/adenine residues.

7. The chimeric protein of claim 1 wherein said DNA mutation binding protein is selected from the group consisting of MutS homologue2, xeroderma pigmentosum complementation group A, xeroderma pigmentosum complementation group C, xeroderma pigmentosum complementation group E, *Thermus thermophiluis* Mut S, thymine DNA glycosylase, *Escherechia coli* Fpapy-DNA glycosylase, *Escherechia coli* endonuclease III, *Escherechia coli* endonuclease IV, T4 endonuclease, *Escherechia coli* uracil DNA glycosylase, *Escherechia coli* A/G-specific adenine DNA glycosylase, *Escherechia coli* Uvr A and *Escherechia coli* Uvr B.

8. The chimeric protein of claim 1 wherein said nuclease is selected from the group consisting of human excision repair cross-complementing rodent repair deficiency complementation group 4 protein, *Serratia marcescens* nuclease, *Escherechia coli* Fpapy-DNA glycosylase; *Escherechia coli* endonuclease III; *Escherechia coli* endonuclease IV; T4 endonuclease; *Escherechia coli* uracil DNA glycosylase; *Escherechia coli* A/G-specific adenine DNA glycosylase, *Escherechia coli* Uvr B nuclease and *Escherechla coil* Uvr C nuclease.

9. The chimeric protein of claim 1 further including a linker peptide.

10. The chimeric protein of claim 9 wherein said linker has the amino acid sequence depicted in SEQ ID NO:17.

11. The protein of claim 7 wherein xeroderma pigmentosum complementation group F has the amino acid sequence depicted in SEQ ID NO: 11.

12. The protein of claim 7 wherein xeroderma pigmentosum complementation group A has the sequence depicted in SEQ ID NO: 7.

13. The protein of claim 7 wherein MutS homologue 2 has the amino acid sequence depicted in SEQ ID NO:1 or SEQ ID NO:3.

14. The protein of claim 7 wherein *Thermus thermophilus* MutS has the amino acid sequence depicted in SEQ ID NO: 15.

15. The protein of claim 7 wherein xeroderma pigmentosum complementation group E has the amino acid sequence depicted in SEQ ID NO: 21.

16. The protein of claim 7 wherein xeroderma pigmentosum complementation group C has the amino acid sequence depicted in SEQ ID NO: 19.

17. The protein of claim 8 wherein human excision repair cross-complementing rodent repair deficiency complementation group 4 protein (XPF) has the amino acid sequence depicted in SEQ ID NO: 11 or SEQ ID NO: 13.

18. The protein of claim 8 wherein *Serratia marcescens* nuclease has the amino acid sequence depicted in SEQ ID NO: 5.

19. The protein of claim 8 wherein *Escherechia coli* Fpapy-DNA glycosylase has the amino acid sequence depicted in SEQ ID NO: 23.

20. The protein of claim 8 wherein *Escherechia coli* endonuclease III has the amino acid sequence depicted in SEQ ID NO: 25.

21. The protein of claim 15 wherein *Escherechia coli* endonuclease IV has the amino acid sequence depicted in SEQ ID NO: 31.

22. A recombinant chimeric protein having the formula A-L-B or B-L-A, wherein:

A is a peptide having DNA mutation binding activity;
L is a linker peptide; and
B is a peptide having nuclease activity.

23. The chimeric protein of claim 22 wherein said linker peptide comprises from 1–30 amino acids.

24. The chimeric protein of claim 23 wherein said linker peptide comprises from 6 to 10 amino acids.

25. The chimeric protein of claim 22 wherein said DNA mutation is selected from the group consisting of single base pair mutations, point mutations, DNA mismatches, DNA insertions, DNA deletions, DNA transversions, DNA transitions, frameshift mutations and damaged DNA.

26. The chimeric protein of claim 22 wherein said DNA mutation is a deaminated base.

27. The chimeric protein of claim 22 wherein said DNA mutation is uracil incorporated DNA.

28. The chimeric protein of claim 22 wherein A is a peptide selected from the group consisting of MutS homologue2, xeroderma pigmentosum complementation group A, xeroderma pigmentosum C, xeroderma pigmentosum complementation group E, *Thermus thermophilus* Mut S, thymine DNA glycosylase, *Escherechia coli* Fpapy-DNA glycosylase, *Escherechia coli* endonuclease III, *Escherechia coli* exonuclease III, *Escherechia coli* endonuclease IV, T4 endonuclease, *Escherechia coli* uracil DNA glycosylase, *Escherechia coli* A/G-specific adenine DNA glycosylase, *Escherechia coli* Uvr A and *Escherechia coli* Uvr B.

29. The chimeric protein of claim 22 wherein B is a peptide selected from the group consisting of the N-terminus of human excision repair cross-complementing rodent repair deficiency, *Serratia marcescens* nuclease, *Escherechia coli* Fpapy-DNA glycosylase; *Escherechia coli* endonuclease III; *Escherechia coli* endonuclease IV; T4 endonuclease; *Escherechia coli* uracil DNA glycosylase; *Escherechia coli* A/G-specific adenine DNA glycosylase, *Esherechia coli* Uvr B nuclease and *Esherechia coli* Uvr C nuclease.

30. An isolated and purified chimeric protein comprising a pair of proteins wherein said pair of proteins are selected from the group consisting of XPF and XPA, XPF and hMSH2, XPA and XPF, hMSH2 and XPF, Nuc and hMSH2, Nuc and XPA, MutS and XPF, XPF and MutS, Nuc and MutS, XPA-and XPF and Nuc and XPA, wherein XPF is human excision repair cross-complementing rodent repair deficiency complementation group 4 protein, XPA is xeroderma pigmentosum complementation group A protein, hMSH2 is human MutS homologue2 protein, Nuc is *Serratia marcescens* nuclease and MutS is *Thermus thermophilus* MutS.

31. The chimeric protein of claim 30 wherein said pair of proteins further includes a linker peptide.

32. The protein of claim 30 wherein XPF has the amino acid sequence depicted in SEQ ID NO: 13 or SEQ ID NO: 11.

33. The protein of claim 31 wherein the linker peptide has the amino acid sequence depicted in SEQ ID NO: 17.

34. The protein of claim 30 wherein hMSH2 has the amino acid sequence depicted in SEQ ID NO: 1or SEQ ID NO: 3.

35. The protein of claim 30 wherein Nuc has the amino acid sequence depicted in SEQ ID NO: 5.

36. The protein of claim 30 wherein MutS has the amino acid sequence depicted in SEQ ID NO: 15.

37. An isolated and purified nucleic acid encoding a chimeric polypeptide comprising a DNA mutation binding protein and a nuclease.

38. A nucleic acid construct comprising the nucleic acid of claim 37.

39. The nucleic acid construct of claim 38 wherein said nucliec acid is operably associated with an expression control sequence functional in a microbial cell.

40. The nucleic acid construct of claim 39 wherein said cell is a bacterial cell.

41. A recombinant bacterial cell comprising the nucleic acid construct of claim 38.

42. An isolated and purified nucleic acid encoding a chimeric protein having the formula A-L-B or B-L-A, wherein:

A is a peptide having DNA mutation binding activity;

L is a linker peptide; and

B is a peptide having nuclease activity.

43. The nucleic acid of claim 42 wherein A is a peptide selected from the group consisting of MutS homologue2, xeroderma pigmentosum complementation group A, xeroderma pigmentosum complementation group C, xeroderma pigmentosum complementation group E, *Thermus thermophilus* Mut S, thymine DNA glycosylase, *Escherechia coli* Fpapy-DNA glycosylase, *Escherechia coli* endonuclease III, *Escherechia coli* exonuclease III, *Escherechia coli* endonuclease IV, T4 endonuclease, *Escherechia coli* uracil DNA glycosylase, *Escherechia coli* A/G-specific adenine DNA glycosylase and *Escherechia coli* Uvr A DNA mutation binding protein and *Escherechia coli* Uvr B DNA mutation binding protein.

44. The nucleic acid of claim 42 wherein B is a peptide selected from the group consisting of human excision repair cross-complementing rodent repair deficiency complementation group 4, *Serratia marcescens* nuclease, *Escherechia coli* Fpapy-DNA glycosylase; *Escherechia coli* endonuclease III; *Escherechia coli* endonuclease IV; T4 endonuclease; *Escherechia coli* uracil DNA glycosylase *Escherechia coli* A/G-specific adenine DNA glycosylase, *Escherechia coli* Uvr B nuclease and *Escherechia coli* Uvr C nuclease.

45. The nucleic acid of claim 43 wherein MutS homolog 2 has the nucleotide sequence depicted in SEQ ID NO: 2 or SEQ ID NO: 4.

46. The nucleic acid of claim 43 wherein xeroderma pigmentosum complementation group A has the nucleotide sequence depicted in SEQ ID NO: 8 or SEQ ID NO: 10.

47. The nucleic acid of claim 43 wherein xeroderma pigmentosum complementation group A has the sequence depicted in SEQ ID NO: 8.

48. The nucleic acid of claim 43 wherein xeroderma pigmentosum complementation group C has the sequence SEQ ID NO: 20.

49. The nucleic acid of claim 43 wherein xeroderma pigmentosum complementation group E has the nucleotide sequence depicted in SEQ ID NO: 22.

50. The nucleic acid of claim 43 wherein *Thermus thermophilus* Mut S has the nucleotide sequence depicted in SEQ ID NO: 16.

51. The nucleic acid of claim 43 wherein thymine DNA glycosylase has the nucleotide sequence depicted in SEQ ID NO: 42.

52. The nucleic acid of claim 43 wherein *Escherechia coli* Fpapy-DNA glycosylase has the nucleotide sequence depicted in SEQ ID NO: 24.

53. The nucleic acid of claim 43 wherein *Escherechia coli* endonuclease III has the nucleotide sequence depicted in SEQ ID NO: 26.

54. The nucleic acid of claim 43 wherein *Escherechia coli* exonuclease III has the nucleotide sequence depicted in SEQ ID NO: 30.

55. The nucleic acid of claim 43 wherein *Escherechia coli* endonuclease IV has the nucleotide sequence depicted in SEQ ID NO: 32.

56. The nucleic acid of claim 43 wherein T4 endonuclease has the nucleotide sequence depicted in SEQ ID NO: 34.

57. The nucleic acid of claim 43 wherein *Escherechia coli* uracil DNA glycosylase has the nucleotide sequence depicted in SEQ ID NO: 36.

58. The nucleic acid of claim 43 wherein *Escherechia coli* A/G-specific adenine DNA glycosylase has the nucleotide sequence depicted in SEQ ID NO: 38.

59. The nucleic acid of claim 44 wherein *Serratia marcescens* nuclease has the nucleotide sequence depicted in SEQ ID NO: 6.

60. A method of detecting a DNA sequence variation in a polynucleotide, comprising:

a) obtaining said polynucleotide;

b) obtaining a chimeric protein wherein said chimeric protein has a DNA mutation binding region and nuclease region wherein said DNA mutation binding region recognizes mutated DNA;

c) forming a mixture of said polynucleotide and said chimeric protein;

d) forming a reacted sample by incubating said mixture under conditions wherein if said polynucleotide includes mutated DNA, said DNA mutation binding region binds to said mutated DNA and said nuclease cuts said mutated DNA; and e) analyzing said reacted sample to determine the extent of cleavage of said polynucleotide to detect said DNA mutation.

61. The method of claim 60 wherein said sequence variation is a DNA mutation.

62. The method of claim 61 wherein said DNA mutation is mismatched DNA.

63. The method of claim 61 wherein said DNA mutation is uracil incorporated DNA.

64. The method of claim 61 wherein said DNA mutation is selected from the group consisting of single base pair mutations, point mutations, DNA mismatches, DNA insertions, DNA deletions, DNA transversions, DNA transitions, frameshift mutations and damaged DNA.

* * * * *

SEQUENCE LISTING

```
<160> NUMBER OF SEQ ID NOS: 106

<210> SEQ ID NO 1
<211> LENGTH: 240
<212> TYPE: PRT
<213> ORGANISM: Homo sapiens

<400> SEQUENCE: 1

Ser Arg His Ala Cys Val Glu Val Gln Asp Glu Ile Ala Phe Ile Pro
 1               5                  10                  15

Asn Asp Val Tyr Phe Glu Lys Asp Lys Gln Met Phe His Ile Ile Thr
            20                  25                  30

Gly Pro Asn Met Gly Gly Lys Ser Thr Tyr Ile Arg Gln Thr Gly Val
        35                  40                  45

Ile Val Leu Met Ala Gln Ile Gly Cys Phe Val Pro Cys Glu Ser Ala
    50                  55                  60

Glu Val Ser Ile Val Asp Cys Ile Leu Ala Arg Val Gly Ala Gly Asp
65                  70                  75                  80

Ser Gln Leu Lys Gly Val Ser Thr Phe Met Ala Glu Met Leu Glu Thr
                85                  90                  95

Ala Ser Ile Leu Arg Ser Ala Thr Lys Asp Ser Leu Ile Ile Ile Asp
            100                 105                 110
```

```
Glu Leu Gly Arg Gly Thr Ser Thr Tyr Asp Gly Phe Gly Leu Ala Trp
            115                 120                 125

Ala Ile Ser Glu Tyr Ile Ala Thr Lys Ile Gly Ala Phe Cys Met Phe
        130                 135                 140

Ala Thr His Phe His Glu Leu Thr Ala Leu Ala Asn Gln Ile Pro Thr
145                 150                 155                 160

Val Asn Asn Leu His Val Thr Ala Leu Thr Thr Glu Thr Leu Thr
                165                 170                 175

Met Leu Tyr Gln Val Lys Lys Gly Val Cys Asp Gln Ser Phe Gly Ile
            180                 185                 190

His Val Ala Glu Leu Ala Asn Phe Pro Lys His Val Ile Glu Cys Ala
            195                 200                 205

Lys Gln Lys Ala Leu Glu Leu Glu Glu Phe Gln Tyr Ile Gly Glu Ser
        210                 215                 220

Gln Gly Tyr Asp Ile Met Glu Pro Ala Ala Lys Lys Cys Tyr Leu Glu
225                 230                 235                 240
```

<210> SEQ ID NO 2
<211> LENGTH: 723
<212> TYPE: DNA
<213> ORGANISM: Homo sapiens

<400> SEQUENCE: 2

```
tccaggcatg cttgtgttga agttcaagat gaaattgcat ttattcctaa tgacgtatac     60
tttgaaaaag ataaacagat gttccacatc attactggcc ccaatatggg aggtaaatca   120
acatatattc gacaaactgg ggtgatagta ctcatggccc aaattgggtg ttttgtgcca   180
tgtgagtcag cagaagtgtc cattgtggac tgcatcttag cccgagtagg ggctggtgac   240
agtcaattga aggagtctc  cacgttcatg gctgaaatgt tggaaactgc ttctatcctc   300
aggtctgcaa ccaaagattc attaataatc atagatgaat gggaagagg  aacttctacc   360
tacgatggat ttgggttagc atgggctata tcagaataca ttgcaacaaa gattggtgct   420
ttttgcatgt ttgcaacccca ttttcatgaa cttactgcct tggccaatca gataccaact   480
gttaataatc tacatgtcac agcactcacc actgaagaga ccttaactat gctttatcag   540
gtgaagaaag gtgtctgtga tcaaagtttt gggattcatg ttgcagagct tgctaatttc   600
cctaagcatg taatagagtg tgctaaacag aaagccctgg aacttgagga gtttcagtat   660
attggagaat cgcaaggata tgatatcatg gaaccagcag caaagaagtg ctatctggaa   720
aga                                                                  723
```

<210> SEQ ID NO 3
<211> LENGTH: 934
<212> TYPE: PRT
<213> ORGANISM: Homo sapiens

<400> SEQUENCE: 3

```
Met Ala Val Gln Pro Lys Glu Thr Leu Gln Leu Glu Ser Ala Ala Glu
1               5                   10                  15

Val Gly Phe Val Arg Phe Phe Gln Gly Met Pro Glu Lys Pro Thr Thr
            20                  25                  30

Thr Val Arg Leu Phe Asp Arg Gly Asp Phe Tyr Thr Ala His Gly Glu
        35                  40                  45

Asp Ala Leu Leu Ala Ala Arg Glu Val Phe Lys Thr Gln Gly Val Ile
    50                  55                  60
```

-continued

```
Lys Tyr Met Gly Pro Ala Gly Lys Asn Leu Gln Ser Val Val Leu
 65                  70                  75                  80

Ser Lys Met Asn Phe Glu Ser Phe Val Lys Asp Leu Leu Val Arg
                 85                  90                  95

Gln Tyr Arg Val Glu Val Tyr Lys Asn Arg Ala Gly Asn Lys Ala Ser
                100                 105                 110

Lys Glu Asn Asp Trp Tyr Leu Ala Tyr Lys Ala Ser Pro Gly Asn Leu
                115                 120                 125

Ser Gln Phe Glu Asp Ile Leu Phe Gly Asn Asn Asp Met Ser Ala Ser
        130                 135                 140

Ile Gly Val Val Gly Val Lys Met Ser Ala Val Asp Gly Gln Arg Gln
145                 150                 155                 160

Val Gly Val Gly Tyr Val Asp Ser Ile Gln Arg Lys Leu Gly Leu Cys
                165                 170                 175

Glu Phe Pro Asp Asn Asp Gln Phe Ser Asn Leu Glu Ala Leu Leu Ile
                180                 185                 190

Gln Ile Gly Pro Lys Glu Cys Val Leu Pro Gly Gly Glu Thr Ala Gly
        195                 200                 205

Asp Met Gly Lys Leu Arg Gln Ile Ile Gln Arg Gly Gly Ile Leu Ile
        210                 215                 220

Thr Glu Arg Lys Lys Ala Asp Phe Ser Thr Lys Asp Ile Tyr Gln Asp
225                 230                 235                 240

Leu Asn Arg Leu Leu Lys Gly Lys Lys Gly Glu Gln Met Asn Ser Ala
                245                 250                 255

Val Leu Pro Glu Met Glu Asn Gln Val Ala Val Ser Ser Leu Ser Ala
                260                 265                 270

Val Ile Lys Phe Leu Glu Leu Leu Ser Asp Asp Ser Asn Phe Gly Gln
        275                 280                 285

Phe Glu Leu Thr Thr Phe Asp Phe Ser Gln Tyr Met Lys Leu Asp Ile
        290                 295                 300

Ala Ala Val Arg Ala Leu Asn Leu Phe Gln Gly Ser Val Glu Asp Thr
305                 310                 315                 320

Thr Gly Ser Gln Ser Leu Ala Ala Leu Leu Asn Lys Cys Lys Thr Pro
                325                 330                 335

Gln Gly Gln Arg Leu Val Asn Gln Trp Ile Lys Gln Pro Leu Met Asp
                340                 345                 350

Lys Asn Arg Ile Glu Glu Arg Leu Asn Leu Val Glu Ala Phe Val Glu
                355                 360                 365

Asp Ala Glu Leu Arg Gln Thr Leu Gln Glu Asp Leu Leu Arg Arg Phe
        370                 375                 380

Pro Asp Leu Asn Arg Leu Ala Lys Lys Phe Gln Arg Gln Ala Ala Asn
385                 390                 395                 400

Leu Gln Asp Cys Tyr Arg Leu Tyr Gln Gly Ile Asn Gln Leu Pro Asn
                405                 410                 415

Val Ile Gln Ala Leu Glu Lys His Glu Gly Lys His Gln Lys Leu Leu
                420                 425                 430

Leu Ala Val Phe Val Thr Pro Leu Thr Asp Leu Arg Ser Asp Phe Ser
        435                 440                 445

Lys Phe Gln Glu Met Ile Glu Thr Thr Leu Asp Met Asp Gln Val Glu
        450                 455                 460

Asn His Glu Phe Leu Val Lys Pro Ser Phe Asp Pro Asn Leu Ser Glu
465                 470                 475                 480

Leu Arg Glu Ile Met Asn Asp Leu Glu Lys Lys Met Gln Ser Thr Leu
```

-continued

```
                485                 490                 495
Ile Ser Ala Ala Arg Asp Leu Gly Leu Asp Pro Gly Lys Gln Ile Lys
            500                 505                 510
Leu Asp Ser Ser Ala Gln Phe Gly Tyr Tyr Phe Arg Val Thr Cys Lys
        515                 520                 525
Glu Glu Lys Val Leu Arg Asn Asn Lys Asn Phe Ser Thr Val Asp Ile
    530                 535                 540
Gln Lys Asn Gly Val Lys Phe Thr Asn Ser Lys Leu Thr Ser Leu Asn
545                 550                 555                 560
Glu Glu Tyr Thr Lys Asn Lys Thr Glu Tyr Glu Ala Gln Asp Ala
                565                 570                 575
Ile Val Lys Glu Ile Val Asn Ile Ser Ser Gly Tyr Val Glu Pro Met
            580                 585                 590
Gln Thr Leu Asn Asp Val Leu Ala Gln Leu Asp Ala Val Val Ser Phe
        595                 600                 605
Ala His Val Ser Asn Gly Ala Pro Val Pro Tyr Val Arg Pro Ala Ile
    610                 615                 620
Leu Glu Lys Gly Gln Gly Arg Ile Ile Leu Lys Ala Ser Arg His Ala
625                 630                 635                 640
Cys Val Glu Val Gln Asp Glu Ile Ala Phe Ile Pro Asn Asp Val Tyr
                645                 650                 655
Phe Glu Lys Asp Lys Gln Met Phe His Ile Ile Thr Gly Pro Asn Met
            660                 665                 670
Gly Gly Lys Ser Thr Tyr Ile Arg Gln Thr Gly Val Ile Val Leu Met
        675                 680                 685
Ala Gln Ile Gly Cys Phe Val Pro Cys Glu Ser Ala Glu Val Ser Ile
    690                 695                 700
Val Asp Cys Ile Leu Ala Arg Val Gly Ala Gly Asp Ser Gln Leu Lys
705                 710                 715                 720
Gly Val Ser Thr Phe Met Ala Glu Met Leu Glu Thr Ala Ser Ile Leu
                725                 730                 735
Arg Ser Ala Thr Lys Asp Ser Leu Ile Ile Ile Asp Glu Leu Gly Arg
            740                 745                 750
Gly Thr Ser Thr Tyr Asp Gly Phe Gly Leu Ala Trp Ala Ile Ser Glu
        755                 760                 765
Tyr Ile Ala Thr Lys Ile Gly Ala Phe Cys Met Phe Ala Thr His Phe
    770                 775                 780
His Glu Leu Thr Ala Leu Ala Asn Gln Ile Pro Thr Val Asn Asn Leu
785                 790                 795                 800
His Val Thr Ala Leu Thr Thr Glu Glu Thr Leu Thr Met Leu Tyr Gln
                805                 810                 815
Val Lys Lys Gly Val Cys Asp Gln Ser Phe Gly Ile His Val Ala Glu
            820                 825                 830
Leu Ala Asn Phe Pro Lys His Val Ile Glu Cys Ala Lys Gln Lys Ala
        835                 840                 845
Leu Glu Leu Glu Glu Phe Gln Tyr Ile Gly Glu Ser Gln Gly Tyr Asp
    850                 855                 860
Ile Met Glu Pro Ala Ala Lys Lys Cys Tyr Leu Glu Arg Glu Gln Gly
865                 870                 875                 880
Glu Lys Ile Ile Gln Glu Phe Leu Ser Lys Val Lys Gln Met Pro Phe
                885                 890                 895
Thr Glu Met Ser Glu Glu Asn Ile Thr Ile Lys Leu Lys Gln Leu Lys
            900                 905                 910
```

Ala Glu Val Ile Ala Lys Asn Asn Ser Phe Val Asn Glu Ile Ile Ser
         915                 920                 925

Arg Ile Lys Val Thr Thr
    930

<210> SEQ ID NO 4
<211> LENGTH: 2805
<212> TYPE: DNA
<213> ORGANISM: Homo sapiens

<400> SEQUENCE: 4

| | | | | | |
|---|---|---|---|---|---|
| atggcggtgc | agccgaagga | gacgctgcag | ttggagagcg | cggccgaggt | cggcttcgtg      60 |
| cgcttctttc | agggcatgcc | ggagaagccg | accaccacag | tgcgccttt | cgaccggggc     120 |
| gacttctata | cggcgcacgg | cgaggacgcg | ctgctggccg | cccgggaggt | gttcaagacc     180 |
| caggggtga | tcaagtacat | ggggccggca | ggagcaaaga | atctgcagag | tgttgtgctt     240 |
| agtaaaatga | attttgaatc | ttttgtaaaa | gatcttcttc | tggttcgtca | gtatagagtt     300 |
| gaagtttata | agaatagagc | tggaaataag | gcatccaagg | agaatgattg | gtatttggca     360 |
| tataaggctt | ctcctggcaa | tctctctcag | tttgaagaca | ttctctttgg | taacaatgat     420 |
| atgtcagctt | ccattggtgt | tgtgggtgtt | aaaatgtccg | cagttgatgg | ccagagacag     480 |
| gttggagttg | ggtatgtgga | ttccatacag | aggaaactag | gactgtgtga | attccctgat     540 |
| aatgatcagt | tctccaatct | tgaggctctc | ctcatccaga | ttggaccaaa | ggaatgtgtt     600 |
| ttacccggag | agagactgc | tggagacatg | gggaaactga | gacagataat | tcaaagagga     660 |
| ggaattctga | tcacagaaag | aaaaaaagct | gacttttcca | caaagacat | ttatcaggac     720 |
| ctcaaccggt | tgttgaaagg | caaaaaggga | gagcagatga | atagtgctgt | attgccagaa     780 |
| atggagaatc | aggttgcagt | ttcatcactg | tctgcggtaa | tcaagttttt | agaactctta     840 |
| tcagatgatt | ccaactttgg | acagtttgaa | ctgactactt | ttgacttcag | ccagtatatg     900 |
| aaattggata | ttgcagcagt | cagagcccctt | aacctttttc | agggttctgt | tgaagatacc     960 |
| actggctctc | agtctctggc | tgccttgctg | aataagtgta | aacccctca | aggacaaaga    1020 |
| cttgttaacc | agtggattaa | gcagcctctc | atggataaga | acagaataga | ggagagattg    1080 |
| aatttagtgg | aagcttttgt | agaagatgca | gaattgaggc | agactttaca | agaagattta    1140 |
| cttcgtcgat | tcccagatct | taaccgactt | gccaagaagt | ttcaaagaca | gcagcaaac    1200 |
| ttacaagatt | gttaccgact | ctatcagggt | ataaatcaac | tacctaatgt | tatacaggct    1260 |
| ctggaaaaac | atgaaggaaa | acaccagaaa | ttattgttgg | cagttttgt | gactcctctt    1320 |
| actgatcttc | gttctgactt | ctccaagttt | caggaaatga | tagaaacaac | tttagatatg    1380 |
| gatcaggtgg | aaaaccatga | attccttgta | aaaccttcat | tgatcctaa | tctcagtgaa    1440 |
| ttaagagaaa | taatgaatga | cttggaaaag | aagatgcagt | caacattaat | aagtgcagcc    1500 |
| agagatcttg | gcttggaccc | tgcaaacag | attaaactgg | attccagtgc | acagtttgga    1560 |
| tattactttc | gtgtaaccctg | taaggaagaa | aaagtccttc | gtaacaataa | aactttagt    1620 |
| actgtagata | tccagaagaa | tggtgttaaa | tttaccaaca | gcaaattgac | ttcttaaat    1680 |
| gaagagtata | ccaaaaataa | aacagaatat | gaagaagccc | aggatgccat | tgttaaagaa    1740 |
| attgtcaata | tttcttcagg | ctatgtagaa | ccaatgcaga | cactcaatga | tgtgttagct    1800 |
| cagctagatg | ctgttgtcag | ctttgctcac | gtgtcaaatg | gagcacctgt | tccatatgta    1860 |
| cgaccagcca | ttttggagaa | aggacaagga | agaattatat | taaaagcatc | caggcatgct    1920 |

-continued

```
tgtgttgaag ttcaagatga aattgcattt attcctaatg acgtatactt tgaaaaagat    1980
aaacagatgt tccacatcat tactggcccc aatatgggag gtaaatcaac atatattcga    2040
caaactgggg tgatagtact catggcccaa attgggtgtt ttgtgccatg tgagtcagca    2100
gaagtgtcca ttgtggactg catcttagcc cgagtagggg ctggtgacag tcaattgaaa    2160
ggagtctcca cgttcatggc tgaaatgttg gaaactgctt ctatcctcag gtctgcaacc    2220
aaagattcat taataatcat agatgaattg ggaagaggaa cttctaccta cgatggattt    2280
gggttagcat gggctatatc agaatacatt gcaacaaaga ttggtgcttt ttgcatgttt    2340
gcaacccatt ttcatgaact tactgccttg gccaatcaga taccaactgt taataatcta    2400
catgtcacag cactccaccac tgaagagacc ttaactatgc tttatcaggt gaagaaaggt    2460
gtctgtgatc aaagttttgg gattcatgtt gcagagcttg ctaatttccc taagcatgta    2520
atagagtgtg ctaaacagaa agccctggaa cttgaggagt ttcagtatat tggagaatcg    2580
caaggatatg atatcatgga accagcagca agaagtgct atctggaaag agagcaaggt    2640
gaaaaaatta ttcaggagtt cctgtccaag gtgaaacaaa tgcccttta c tgaaatgtca    2700
gaagaaaaca tcacaataaa gttaaaacag ctaaaagctg aagtaatagc aaagaataat    2760
agctttgtaa atgaaatcat ttcacgaata aaagttacta cgtga                   2805
```

<210> SEQ ID NO 5
<211> LENGTH: 266
<212> TYPE: PRT
<213> ORGANISM: Serratia marcescens

<400> SEQUENCE: 5

```
Met Arg Phe Asn Asn Lys Met Leu Ala Leu Ala Ala Leu Leu Phe Ala
 1               5                  10                  15

Ala Gln Ala Ser Ala Asp Thr Leu Glu Ser Ile Asp Asn Cys Ala Val
            20                  25                  30

Gly Cys Pro Thr Gly Gly Ser Ser Asn Val Ser Ile Val Arg His Ala
        35                  40                  45

Tyr Thr Leu Asn Asn Asn Ser Thr Thr Lys Phe Ala Asn Trp Val Ala
    50                  55                  60

Tyr His Ile Thr Lys Asp Thr Pro Ala Ser Gly Lys Thr Arg Asn Trp
65                  70                  75                  80

Lys Thr Asp Pro Ala Leu Asn Pro Ala Asp Thr Leu Ala Pro Ala Asp
                85                  90                  95

Tyr Thr Gly Ala Asn Ala Ala Leu Lys Val Asp Arg Gly His Gln Ala
            100                 105                 110

Pro Leu Ala Ser Leu Ala Gly Val Ser Asp Trp Glu Ser Leu Asn Tyr
        115                 120                 125

Leu Ser Asn Ile Thr Pro Gln Lys Ser Asp Leu Asn Gln Gly Ala Trp
    130                 135                 140

Ala Arg Leu Glu Asp Gln Glu Arg Lys Leu Ile Asp Arg Ala Asp Ile
145                 150                 155                 160

Ser Ser Val Tyr Thr Val Thr Gly Pro Leu Tyr Glu Arg Asp Met Gly
                165                 170                 175

Lys Leu Pro Gly Thr Gln Lys Ala His Thr Ile Pro Ser Ala Tyr Trp
            180                 185                 190

Lys Val Ile Phe Ile Asn Asn Ser Pro Ala Val Asn His Tyr Ala Ala
        195                 200                 205

Phe Leu Phe Asp Gln Asn Thr Pro Lys Gly Ala Asp Phe Cys Gln Phe
    210                 215                 220
```

```
Arg Val Thr Val Asp Glu Ile Glu Lys Arg Thr Gly Leu Ile Ile Trp
225                 230                 235                 240

Ala Gly Leu Pro Asp Asp Val Gln Ala Ser Leu Lys Ser Lys Pro Gly
                245                 250                 255

Val Leu Pro Glu Leu Met Gly Cys Lys Asn
            260                 265
```

<210> SEQ ID NO 6
<211> LENGTH: 801
<212> TYPE: DNA
<213> ORGANISM: Serratia marcescens

<400> SEQUENCE: 6

```
atgcgcttta caacaagat gttggccttg ccgccctgc tgttcgccgc gcaggcgtcg      60
gccgacacgc tcgaatccat cgacaactgc gcggtcggct cccgaccgg cggcagcagc    120 aacgtgtcta tcgtgcgcca tgcttatacg ttgaacaaca cagcaccac caagttcgcc    180 aactgggtgg cctatcacat caccaaagac acgccggcca gcggcaagac gcgcaactgg    240
aaaaccgatc cggctctcaa tccggcggac actctggcgc ccgccgatta caccggtgcc    300
aacgccgcgc tgaaggtcga tcgcggtcat caggcgccgc tggcctcgct ggcgggcgtt    360
tccgactggg aatcgttgaa ctacctgtcc aacatcacgc gcaaaagtc cgatctgaac    420 cagggcgcct gggctcggct ggaagatcag gaacgcaagc tgatcgatcg cgccgatatc    480
tcctcggtct ataccgtgac cgggccgctg tatgagcgcg atatgggcaa actgccgggc    540
acccagaaag cgcacaccat ccccagcgcc tactggaagg taattttcat caacaacagc    600
ccggcggtga accactatgc cgccttcctg ttcgaccaga cacgccgaa gggcgccgat    660 ttctgccaat ccgcgtgac ggtggacgag atcgagaaac gcaccggcct gatcatctgg    720
gccggtctgc cggacgacgt gcaggcttcg ctgaagagca accgggcgt tctgccggag    780 ttgatgggct gcaaaaactg a                                              801
```

<210> SEQ ID NO 7
<211> LENGTH: 273
<212> TYPE: PRT
<213> ORGANISM: Homo sapiens

<400> SEQUENCE: 7

```
Met Ala Ala Ala Asp Gly Ala Leu Pro Glu Ala Ala Leu Glu Gln
1               5                  10                  15

Pro Ala Glu Leu Pro Ala Ser Val Arg Ala Ser Ile Glu Arg Lys Arg
                20                  25                  30

Gln Arg Ala Leu Met Leu Arg Gln Ala Arg Leu Ala Ala Arg Pro Tyr
            35                  40                  45

Ser Ala Thr Ala Ala Ala Thr Gly Gly Met Ala Asn Val Lys Ala
        50                  55                  60

Ala Pro Lys Ile Ile Asp Thr Gly Gly Phe Ile Leu Glu Glu
65                  70                  75                  80

Glu Glu Glu Glu Gln Lys Ile Gly Lys Val Val His Gln Pro Gly Pro
                85                  90                  95

Val Met Glu Phe Asp Tyr Val Ile Cys Glu Glu Cys Gly Lys Glu Phe
                100                 105                 110

Met Asp Ser Tyr Leu Met Asn His Phe Asp Leu Pro Thr Cys Asp Asn
            115                 120                 125

Cys Arg Asp Ala Asp Asp Lys His Lys Leu Ile Thr Lys Thr Glu Ala
```

```
                130              135                140
Lys Gln Glu Tyr Leu Leu Lys Asp Cys Asp Leu Glu Lys Arg Glu Pro
145                  150                155                160

Pro Leu Lys Phe Ile Val Lys Lys Asn Pro His His Ser Gln Trp Gly
                165                170                175

Asp Met Lys Leu Tyr Leu Lys Leu Gln Ile Val Lys Arg Ser Leu Glu
                180                185                190

Val Trp Gly Ser Gln Glu Ala Leu Glu Ala Lys Glu Val Arg Gln
            195                200                205

Glu Asn Arg Glu Lys Met Lys Gln Lys Lys Phe Asp Lys Lys Val Lys
    210                215                220

Glu Leu Arg Arg Ala Val Arg Ser Ser Val Trp Lys Arg Glu Thr Ile
225                230                235                240

Val His Gln His Glu Tyr Gly Pro Glu Glu Asn Leu Glu Asp Asp Met
                245                250                255

Tyr Arg Lys Thr Cys Thr Met Cys Gly His Glu Leu Thr Tyr Glu Lys
                260                265                270

Met
```

<210> SEQ ID NO 8
<211> LENGTH: 822
<212> TYPE: DNA
<213> ORGANISM: Homo sapiens

<400> SEQUENCE: 8

```
atggcggcgg ccgacggggc tttgccggag gcggcggctt tagagcaacc cgcggagctg     60
cctgcctcgg tgcgggcgag tatcgagcgg aagcggcagc gggcactgat gctgcgccag    120
gcccggctgg ctgcccggcc ctactcggcg acggcggctg cggctactgg aggcatggct    180
aatgtaaaag cagccccaaa gataattgac acaggaggag gcttcatttt agaagaggaa    240
gaagaagaag aacagaaaat tggaaaagtt gttcatcaac caggacctgt tatggaattt    300
gattatgtaa tatgcgaaga atgtgggaaa gaatttatgg attcttatct tatgaaccac    360
tttgatttgc caacttgtga taactgcaga gatgctgatg ataaacacaa gcttataacc    420
aaaacagagg caaaacaaga atatcttctg aaagactgtg atttagaaaa aagagagcca    480
cctcttaaat ttattgtgaa gaagaatcca catcattcac aatgggtgat atgaaactc    540
tacttaaagt tacagattgt gaagaggtct cttgaagttt ggggtagtca agaagcatta    600
gaagaagcaa aggaagtccg acaggaaaac cgagaaaaaa tgaaacagaa gaaatttgat    660
aaaaaagtaa agaattgcg gcgagcagta agaagcagcg tgtggaaaag ggagacgatt    720
gttcatcaac atgagtatgg accagaagaa aacctagaag atgacatgta ccgtaagact    780
tgtactatgt gtggccatga actgacatat gaaaaaatgt ga                        822
```

<210> SEQ ID NO 9
<211> LENGTH: 122
<212> TYPE: PRT
<213> ORGANISM: Homo sapiens

<400> SEQUENCE: 9

```
Met Glu Phe Asp Tyr Val Ile Cys Glu Glu Cys Gly Lys Glu Phe Met
  1                 5                 10                15

Asp Ser Tyr Leu Met Asn His Phe Asp Leu Pro Thr Cys Asp Asn Cys
                20                 25                30

Arg Asp Ala Asp Asp Lys His Lys Leu Ile Thr Lys Thr Glu Ala Lys
```

```
                     35                  40                  45
Gln Glu Tyr Leu Leu Lys Asp Cys Asp Leu Glu Lys Arg Glu Pro Pro
     50                  55                  60

Leu Lys Phe Ile Val Lys Lys Asn Pro His His Ser Gln Trp Gly Asp
 65                  70                  75                  80

Met Lys Leu Tyr Leu Lys Leu Gln Ile Val Lys Arg Ser Leu Glu Val
                 85                  90                  95

Trp Gly Ser Gln Glu Ala Leu Glu Glu Ala Lys Glu Val Arg Gln Glu
            100                 105                 110

Asn Arg Glu Lys Met Lys Gln Lys Phe
        115                 120

<210> SEQ ID NO 10
<211> LENGTH: 366
<212> TYPE: DNA
<213> ORGANISM: Homo sapiens

<400> SEQUENCE: 10
atggaatttg attatgtaat atgcgaagaa tgtgggaaag aatttatgga ttcttatctt      60
atgaaccact ttgatttgcc aacttgtgat aactgcagag atgctgatga taaacacaag     120
cttataacca aaacagaggc aaaacaagaa tatcttctga agactgtga tttagaaaaa      180 agagagccac tcttaaaatt tattgtgaag aagaatccac atcattcaca atgggtgat     240 atgaaactct acttaaagtt acagattgtg aagaggtctc ttgaagtttg ggtagtcaa      300 gaagcattag aagaagcaaa ggaagtccga caggaaaacc gagaaaaaat gaaacagaag     360
aaattt                                                                366

<210> SEQ ID NO 11
<211> LENGTH: 367
<212> TYPE: PRT
<213> ORGANISM: Homo sapiens

<400> SEQUENCE: 11

Met Ala Pro Leu Leu Glu Tyr Glu Arg Gln Leu Val Leu Glu Leu Leu
  1               5                  10                  15

Asp Thr Asp Gly Leu Val Val Cys Ala Arg Gly Leu Gly Ala Asp Arg
             20                  25                  30

Leu Leu Tyr His Phe Leu Gln Leu His Cys His Pro Ala Cys Leu Val
         35                  40                  45

Leu Val Leu Asn Thr Gln Pro Ala Glu Glu Glu Tyr Phe Ile Asn Gln
     50                  55                  60

Leu Lys Ile Glu Gly Val Glu His Leu Pro Arg Arg Val Thr Asn Glu
 65                  70                  75                  80

Ile Thr Ser Asn Ser Arg Tyr Glu Val Tyr Thr Gln Gly Gly Val Ile
                 85                  90                  95

Phe Ala Thr Ser Arg Ile Leu Val Val Asp Phe Leu Thr Asp Arg Ile
            100                 105                 110

Pro Ser Asp Leu Ile Thr Gly Ile Leu Val Tyr Arg Ala His Arg Ile
        115                 120                 125

Ile Glu Ser Cys Gln Glu Ala Phe Ile Leu Arg Leu Phe Arg Gln Lys
    130                 135                 140

Asn Lys Arg Gly Phe Ile Lys Ala Phe Thr Asp Asn Ala Val Ala Phe
145                 150                 155                 160

Asp Thr Gly Phe Cys His Val Glu Arg Val Met Arg Asn Leu Phe Val
                165                 170                 175
```

-continued

```
Arg Lys Leu Tyr Leu Trp Pro Arg Phe His Val Ala Val Asn Ser Phe
            180                 185                 190
Leu Glu Gln His Lys Pro Glu Val Val Glu Ile His Val Ser Met Thr
        195                 200                 205
Pro Thr Met Leu Ala Ile Gln Thr Ala Ile Leu Asp Ile Leu Asn Ala
    210                 215                 220
Cys Leu Lys Glu Leu Lys Cys His Asn Pro Ser Leu Glu Val Glu Asp
225                 230                 235                 240
Leu Ser Leu Glu Asn Ala Ile Gly Lys Pro Phe Asp Lys Thr Ile Arg
                245                 250                 255
His Tyr Leu Asp Pro Leu Trp His Gln Leu Gly Ala Lys Thr Lys Ser
            260                 265                 270
Leu Val Gln Asp Leu Lys Ile Leu Arg Thr Leu Leu Gln Tyr Leu Ser
        275                 280                 285
Gln Tyr Asp Cys Val Thr Phe Leu Asn Leu Leu Glu Ser Leu Arg Ala
    290                 295                 300
Thr Glu Lys Ala Phe Gly Gln Asn Ser Gly Trp Leu Phe Leu Asp Ser
305                 310                 315                 320
Ser Thr Ser Met Phe Ile Asn Ala Arg Ala Arg Val Tyr His Leu Pro
                325                 330                 335
Asp Ala Lys Met Ser Lys Lys Glu Lys Ile Ser Glu Lys Met Glu Ile
            340                 345                 350
Lys Glu Gly Glu Glu Thr Lys Lys Glu Leu Val Leu Glu Ser Asn
        355                 360                 365

<210> SEQ ID NO 12
<211> LENGTH: 1101
<212> TYPE: DNA
<213> ORGANISM: Homo sapiens

<400> SEQUENCE: 12
atggcgccgc tgctggagta cgagcgacag ctggtgctgg aactgctcga cactgacggg     60
ctagtagtgt gcgcccgcgg gctcggcgcg gaccggctcc tctaccactt tctccagctg    120
cactgccacc cagcctgcct ggtgctggtg ctcaacacgc agccggccga ggaggagtat    180
tttatcaatc agctgaagat agaaggagtt gaacacctcc ctcgccgtgt aacaaatgaa    240
atcacaagca acagtcgcta tgaagtttac acacaaggtg gtgttatatt tgcgacaagt    300
aggatacttg tggttgactt cttgactgat agaatacctt cagatttaat tactggcatc    360
ttggtgtata gagcccacag aataatcgag tcttgtcaag aagcattcat cttgcgcctc    420
tttcgccaga aaaacaaacg tggttttatt aaagctttca cagacaatgc tgttgccttt    480
gatactggtt tttgtcatgt ggaaagagtg atgagaaatc tttttgtgag gaaactgtat    540
ctgtggccaa ggttccatgt agcagtaaac tcattttag aacagcacaa acctgaagtt    600
gtagaaatcc atgtttctat gacacctacc atgcttgcta tacagactgc tatactggac    660
attttaaatg catgtctaaa ggaactaaaa tgccataacc catcgcttga agtggaagat    720
ttatctttag aaaatgctat tggaaaacct tttgacaaga caatccgcca ttatctggat    780
cctttgtggc accagcttgg agccaagact aaatccttag ttcaggattt gaagatatta    840
cgaactttgc tgcagtatct ctctcagtat gattgtgtca catttcttaa tcttctggaa    900
tctctgagag caacggaaaa agcttttggt cagaattcag gttggctgtt tcttgactcc    960
agcacctcga tgtttataaa tgctcgagca agggtttatc atcttccaga tgccaaaatg   1020
```

-continued

```
agtaaaaaag aaaaaatatc tgaaaaaatg gaaattaaag aagggggaaga aacaaaaaag    1080 gaactggtcc tagaaagcaa c                                               1101
```

<210> SEQ ID NO 13
<211> LENGTH: 906
<212> TYPE: PRT
<213> ORGANISM: Homo sapiens

<400> SEQUENCE: 13

| | | | | | | | | | | | | | | |
|---|---|---|---|---|---|---|---|---|---|---|---|---|---|---|
| Met | Ala | Pro | Leu | Leu | Glu | Tyr | Glu | Arg | Gln | Leu | Val | Leu | Glu | Leu | Leu |
| 1 | | | | 5 | | | | | 10 | | | | | 15 | |

| Asp | Thr | Asp | Gly | Leu | Val | Val | Cys | Ala | Arg | Gly | Leu | Gly | Ala | Asp | Arg |
|---|---|---|---|---|---|---|---|---|---|---|---|---|---|---|---|
| | | | 20 | | | | | 25 | | | | | 30 | | |

| Leu | Leu | Tyr | His | Phe | Leu | Gln | Leu | His | Cys | His | Pro | Ala | Cys | Leu | Val |
|---|---|---|---|---|---|---|---|---|---|---|---|---|---|---|---|
| | | 35 | | | | | 40 | | | | | 45 | | | |

| Leu | Val | Leu | Asn | Thr | Gln | Pro | Ala | Glu | Glu | Tyr | Phe | Ile | Asn | Gln |
|---|---|---|---|---|---|---|---|---|---|---|---|---|---|---|
| | 50 | | | | | 55 | | | | | 60 | | | |

| Leu | Lys | Ile | Glu | Gly | Val | Glu | His | Leu | Pro | Arg | Arg | Val | Thr | Asn | Glu |
|---|---|---|---|---|---|---|---|---|---|---|---|---|---|---|---|
| 65 | | | | | 70 | | | | | 75 | | | | | 80 |

| Ile | Thr | Ser | Asn | Ser | Arg | Tyr | Glu | Val | Tyr | Thr | Gln | Gly | Gly | Val | Ile |
|---|---|---|---|---|---|---|---|---|---|---|---|---|---|---|---|
| | | | | 85 | | | | | 90 | | | | | 95 | |

| Phe | Ala | Thr | Ser | Arg | Ile | Leu | Val | Val | Asp | Phe | Leu | Thr | Asp | Arg | Ile |
|---|---|---|---|---|---|---|---|---|---|---|---|---|---|---|---|
| | | | 100 | | | | | 105 | | | | | 110 | | |

| Pro | Ser | Asp | Leu | Ile | Thr | Gly | Ile | Leu | Val | Tyr | Arg | Ala | His | Arg | Ile |
|---|---|---|---|---|---|---|---|---|---|---|---|---|---|---|---|
| | | 115 | | | | | 120 | | | | | 125 | | | |

| Ile | Glu | Ser | Cys | Gln | Glu | Ala | Phe | Ile | Leu | Arg | Leu | Phe | Arg | Gln | Lys |
|---|---|---|---|---|---|---|---|---|---|---|---|---|---|---|---|
| | 130 | | | | | 135 | | | | | 140 | | | | |

| Asn | Lys | Arg | Gly | Phe | Ile | Lys | Ala | Phe | Thr | Asp | Asn | Ala | Val | Ala | Phe |
|---|---|---|---|---|---|---|---|---|---|---|---|---|---|---|---|
| 145 | | | | | 150 | | | | | 155 | | | | | 160 |

| Asp | Thr | Gly | Phe | Cys | His | Val | Glu | Arg | Val | Met | Arg | Asn | Leu | Phe | Val |
|---|---|---|---|---|---|---|---|---|---|---|---|---|---|---|---|
| | | | | 165 | | | | | 170 | | | | | 175 | |

| Arg | Lys | Leu | Tyr | Leu | Trp | Pro | Arg | Phe | His | Val | Ala | Val | Asn | Ser | Phe |
|---|---|---|---|---|---|---|---|---|---|---|---|---|---|---|---|
| | | | 180 | | | | | 185 | | | | | 190 | | |

| Leu | Glu | Gln | His | Lys | Pro | Glu | Val | Val | Glu | Ile | His | Val | Ser | Met | Thr |
|---|---|---|---|---|---|---|---|---|---|---|---|---|---|---|---|
| | | 195 | | | | | 200 | | | | | 205 | | | |

| Pro | Thr | Met | Leu | Ala | Ile | Gln | Thr | Ala | Ile | Leu | Asp | Ile | Leu | Asn | Ala |
|---|---|---|---|---|---|---|---|---|---|---|---|---|---|---|---|
| | 210 | | | | | 215 | | | | | 220 | | | | |

| Cys | Leu | Lys | Glu | Leu | Lys | Cys | His | Asn | Pro | Ser | Leu | Glu | Val | Glu | Asp |
|---|---|---|---|---|---|---|---|---|---|---|---|---|---|---|---|
| 225 | | | | | 230 | | | | | 235 | | | | | 240 |

| Leu | Ser | Leu | Glu | Asn | Ala | Ile | Gly | Lys | Pro | Phe | Asp | Lys | Thr | Ile | Arg |
|---|---|---|---|---|---|---|---|---|---|---|---|---|---|---|---|
| | | | | 245 | | | | | 250 | | | | | 255 | |

| His | Tyr | Leu | Asp | Pro | Leu | Trp | His | Gln | Leu | Gly | Ala | Lys | Thr | Lys | Ser |
|---|---|---|---|---|---|---|---|---|---|---|---|---|---|---|---|
| | | | 260 | | | | | 265 | | | | | 270 | | |

| Leu | Val | Gln | Asp | Leu | Lys | Ile | Leu | Arg | Thr | Leu | Leu | Gln | Tyr | Leu | Ser |
|---|---|---|---|---|---|---|---|---|---|---|---|---|---|---|---|
| | | 275 | | | | | 280 | | | | | 285 | | | |

| Gln | Tyr | Asp | Cys | Val | Thr | Phe | Leu | Asn | Leu | Leu | Glu | Ser | Leu | Arg | Ala |
|---|---|---|---|---|---|---|---|---|---|---|---|---|---|---|---|
| | 290 | | | | | 295 | | | | | 300 | | | | |

| Thr | Glu | Lys | Ala | Phe | Gly | Gln | Asn | Ser | Gly | Trp | Leu | Phe | Leu | Asp | Ser |
|---|---|---|---|---|---|---|---|---|---|---|---|---|---|---|---|
| 305 | | | | | 310 | | | | | 315 | | | | | 320 |

| Ser | Thr | Ser | Met | Phe | Ile | Asn | Ala | Arg | Ala | Arg | Val | Tyr | His | Leu | Pro |
|---|---|---|---|---|---|---|---|---|---|---|---|---|---|---|---|
| | | | | 325 | | | | | 330 | | | | | 335 | |

| Asp | Ala | Lys | Met | Ser | Lys | Lys | Glu | Lys | Ile | Ser | Glu | Lys | Met | Glu | Ile |
|---|---|---|---|---|---|---|---|---|---|---|---|---|---|---|---|
| | | | 340 | | | | | 345 | | | | | 350 | | |

| Lys | Glu | Gly | Glu | Glu | Thr | Lys | Lys | Glu | Leu | Val | Leu | Glu | Ser | Asn | Pro |

-continued

```
              355                 360                 365
Lys Trp Glu Ala Leu Thr Glu Val Leu Lys Glu Ile Glu Ala Glu Asn
    370                 375                 380
Lys Glu Ser Glu Ala Leu Gly Gly Pro Gly Gln Val Leu Ile Cys Ala
385                 390                 395                 400
Ser Asp Asp Arg Thr Cys Ser Gln Leu Arg Asp Tyr Ile Thr Leu Gly
                405                 410                 415
Ala Glu Ala Phe Leu Leu Arg Leu Tyr Arg Lys Thr Phe Glu Lys Asp
                420                 425                 430
Ser Lys Ala Glu Glu Val Trp Met Lys Phe Arg Lys Glu Asp Ser Ser
            435                 440                 445
Lys Arg Ile Arg Lys Ser His Lys Arg Pro Lys Asp Pro Gln Asn Lys
    450                 455                 460
Glu Arg Ala Ser Thr Lys Glu Arg Thr Leu Lys Lys Lys Arg Lys
465                 470                 475                 480
Leu Thr Leu Thr Gln Met Val Gly Lys Pro Glu Leu Glu Glu Glu
                485                 490                 495
Gly Asp Val Glu Glu Gly Tyr Arg Arg Glu Ile Ser Ser Ser Pro Glu
                500                 505                 510
Ser Cys Pro Glu Glu Ile Lys His Glu Glu Phe Asp Val Asn Leu Ser
            515                 520                 525
Ser Asp Ala Ala Phe Gly Ile Leu Lys Glu Pro Leu Thr Ile Ile His
        530                 535                 540
Pro Leu Leu Gly Cys Ser Asp Pro Tyr Ala Leu Thr Arg Val Leu His
545                 550                 555                 560
Glu Val Glu Pro Arg Tyr Val Val Leu Tyr Asp Ala Glu Leu Thr Phe
                565                 570                 575
Val Arg Gln Leu Glu Ile Tyr Arg Ala Ser Arg Pro Gly Lys Pro Leu
            580                 585                 590
Arg Val Tyr Phe Leu Ile Tyr Gly Gly Ser Thr Glu Glu Gln Arg Tyr
        595                 600                 605
Leu Thr Ala Leu Arg Lys Glu Lys Glu Ala Phe Glu Lys Leu Ile Arg
    610                 615                 620
Glu Lys Ala Ser Met Val Val Pro Glu Glu Arg Glu Gly Arg Asp Glu
625                 630                 635                 640
Thr Asn Leu Asp Leu Val Arg Gly Thr Ala Ser Ala Asp Val Ser Thr
                645                 650                 655
Asp Thr Arg Lys Ala Gly Gly Gln Glu Gln Asn Gly Thr Gln Gln Ser
            660                 665                 670
Ile Val Val Asp Met Arg Glu Phe Arg Ser Glu Leu Pro Ser Leu Ile
        675                 680                 685
His Arg Arg Gly Ile Asp Ile Glu Pro Val Thr Leu Glu Val Gly Asp
    690                 695                 700
Tyr Ile Leu Thr Pro Glu Met Cys Val Glu Arg Lys Ser Ile Ser Asp
705                 710                 715                 720
Leu Ile Gly Ser Leu Asn Asn Gly Arg Leu Tyr Ser Gln Cys Ile Ser
                725                 730                 735
Met Ser Arg Tyr Tyr Lys Arg Pro Val Leu Leu Ile Glu Phe Asp Pro
            740                 745                 750
Ser Lys Pro Phe Ser Leu Thr Ser Arg Gly Ala Leu Phe Gln Glu Ile
        755                 760                 765
Ser Ser Asn Asp Ile Ser Ser Lys Leu Thr Leu Leu Thr Leu His Phe
    770                 775                 780
```

```
Pro Arg Leu Arg Ile Leu Trp Cys Pro Ser Pro His Ala Thr Ala Glu
785                 790                 795                 800

Leu Phe Glu Glu Leu Lys Gln Ser Lys Pro Gln Pro Asp Ala Ala Thr
                805                 810                 815

Ala Leu Ala Ile Thr Ala Asp Ser Glu Thr Leu Pro Glu Ser Glu Lys
            820                 825                 830

Tyr Asn Pro Gly Pro Gln Asp Phe Leu Leu Lys Met Pro Gly Val Asn
        835                 840                 845

Ala Lys Asn Cys Arg Ser Leu Met His His Val Lys Asn Ile Ala Glu
    850                 855                 860

Leu Ala Ala Leu Ser Gln Asp Glu Leu Thr Ser Ile Leu Gly Asn Ala
865                 870                 875                 880

Ala Asn Ala Lys Gln Leu Tyr Asp Phe Ile His Thr Ser Phe Ala Glu
                885                 890                 895

Val Val Ser Lys Gly Lys Gly Lys Lys Glx
                900                 905

<210> SEQ ID NO 14
<211> LENGTH: 2718
<212> TYPE: DNA
<213> ORGANISM: Homo sapiens

<400> SEQUENCE: 14
atggcgccgc tgctggagta cgagcgacag ctggtgctgg aactgctcga cactgacggg      60
ctagtagtgt gcgcccgcgg gctcggcgcg gaccggctcc tctaccactt tctccagctg     120
cactgccacc cagcctgcct ggtgctggtg ctcaacacgc agccggccga ggaggagtat     180
tttatcaatc agctgaagat agaaggagtt gaacacctcc ctcgccgtgt aacaaatgaa     240
atcacaagca acagtcgcta tgaagtttac acacaaggtg gtgttatatt tgcgacaagt     300
aggatacttg tggttgactt cttgactgat agaatacctt cagatttaat tactggcatc     360
ttggtgtata gagcccacag aataatcgag tcttgtcaag aagcattcat cttgcgcctc     420
tttcgccaga aaaacaaacg tggttttatt aaagctttca cagacaatgc tgttgccttt     480
gatactggtt tttgtcatgt ggaaagagtg atgagaaatc tttttgtgag gaaactgtat     540
ctgtggccaa ggttccatgt agcagtaaac tcattttag aacagcacaa acctgaagtt      600
gtagaaatcc atgtttctat gacacctacc atgcttgcta tacagactgc tatactggac     660
attttaaatg catgtctaaa ggaactaaaa tgccataacc atcgcttga agtggaagat      720 ttatctttag aaaatgctat tggaaaacct tttgacaaga caatccgcca ttatctggat     780
cctttgtggc accagcttgg agccaagact aaatccttag ttcaggattt gaagatatta     840
cgaactttgc tgcagtatct ctctcagtat gattgtgtca catttcttaa tcttctggaa     900
tctctgagag caacggaaaa agcttttggt cagaattcag gttggctgtt tcttgactcc     960
agcacctcga tgtttataaa tgctcgagca agggtttatc atcttccaga tgccaaaatg    1020
agtaaaaaag aaaaaatatc tgaaaaaatg gaattaaag aagggaaga acaaaaaag       1080 gaactggtcc tagaaagcaa cccaaagtgg gaggcactga ctgaagtatt aaaagaaatt    1140
gaggcagaaa ataaggagag tgaagctctt ggtggtccag tcaagtact gatttgtgca     1200 agtgatgacc gaacatgttc ccagctgaga gactatatca ctcttggagc ggaggccttc    1260
ttattgaggc tctacaggaa aacctttgag aaggatagca agctgaaga agtctggatg     1320 aaatttagga aggaagacag ttcaaagaga attaggaaat ctcacaaaag acctaaagac    1380
```

-continued

```
cccaaaaca aagaacgggc ttctaccaaa gaaagaaccc tcaaaaagaa aaacggaag    1440 ttgaccttaa ctcaaatggt aggaaaacct gaagaactgg aagaggaagg agatgtcgag    1500
gaaggatatc gtcgagaaat aagcagtagc ccagaaagct gcccggaaga aattaagcat    1560
gaagaatttg atgtaaattt gtcatcggat gctgctttcg gaatcctgaa agaaccctc    1620 actatcatcc atccgcttct gggttgcagc gacccctatg ctctgacaag ggtactacat    1680
gaagtggagc caagatacgt ggttctttat gacgcagagc taacctttgt tcggcagctt    1740
gaaatttaca gggcgagtag gcctgggaaa cctctgaggg tttactttct tatatacgga    1800
ggttcaactg aggaacaacg ctatctcact gctttgcgga agaaaagga agcttttgaa    1860 aaactcataa gggaaaaagc aagcatggtt gtccctgaag aaagagaagg cagagatgaa    1920
acaaacttag acctagtaag aggcacagca tctgcagatg tttccactga cactcggaaa    1980
gccggtggcc aggaacagaa tggtacacag caaagcatag ttgtggatat gcgtgaattt    2040
cgaagtgagc ttccatctct gatccatcgt cggggcattg acattgaacc cgtgacttta    2100
gaggttggag attacatcct cactccagaa atgtgcgtgg agcgcaagag tatcagtgat    2160
ttaatcggct ctttaaataa cggccgcctc tacagccagt gcatctccat gtcccgctac    2220
tacaagcgtc ccgtgcttct gattgagttt gaccctagca agcctttctc tctcacttcc    2280
cgaggtgcct tgtttcagga gatctccagc aatgacatta gttccaaact cactcttctt    2340
acacttcact tccccagact acggattctc tggtgcccct ctcctcatgc aacggcggag    2400
ttgtttgagg agctgaaaca aagcaagcca cagcctgatg cggcgacagc actggccatt    2460
acagcagatt ctgaaaccct tcccgagtca gagaagtata atcctggtcc ccaagacttc    2520
ttgttaaaaa tgccaggggt gaatgccaaa aactgccgct ccttgatgca ccacgttaag    2580
aacatcgcag aattagcagc cctgtcacaa gacgagctca cgagtattct ggggaatgct    2640
gcaaatgcca aacagcttta tgatttcatt cacacctctt ttgcagaagt cgtatcaaaa    2700
ggaaaaggga aaaagtga                                                 2718
```

<210> SEQ ID NO 15
<211> LENGTH: 819
<212> TYPE: PRT
<213> ORGANISM: Thermus thermophilus

<400> SEQUENCE: 15

```
Met Gly Gly Tyr Gly Gly Val Lys Met Glu Gly Met Leu Lys Gly Glu
 1               5                  10                  15

Gly Pro Gly Pro Leu Pro Pro Leu Leu Gln Gln Tyr Val Glu Leu Arg
            20                  25                  30

Asp Arg Tyr Pro Asp Tyr Leu Leu Leu Phe Gln Val Gly Asp Phe Tyr
        35                  40                  45

Glu Cys Phe Gly Glu Asp Ala Glu Arg Leu Ala Arg Ala Leu Gly Leu
    50                  55                  60

Val Leu Thr His Lys Thr Ser Lys Asp Phe Thr Thr Pro Met Ala Gly
65                  70                  75                  80

Ile Pro Ile Arg Ala Phe Asp Ala Tyr Ala Glu Arg Leu Leu Lys Met
                85                  90                  95

Gly Phe Arg Leu Ala Val Ala Asp Gln Val Glu Pro Ala Glu Glu Ala
            100                 105                 110

Glu Gly Leu Val Arg Arg Glu Val Thr Gln Leu Leu Thr Pro Gly Thr
        115                 120                 125

Leu Thr Gln Glu Ala Leu Leu Pro Arg Glu Ala Asn Tyr Leu Ala Ala
```

```
                130                 135                 140
Ile Ala Thr Gly Asp Gly Trp Gly Leu Ala Phe Leu Asp Val Ser Thr
145                 150                 155                 160
Gly Glu Phe Lys Gly Thr Leu Leu Lys Ser Lys Ser Ala Leu Tyr Asp
                165                 170                 175
Glu Leu Phe Arg His Arg Pro Ala Glu Val Leu Leu Ala Pro Glu Leu
            180                 185                 190
Arg Glu Asn Glu Ala Phe Val Ala Glu Phe Arg Lys Arg Phe Pro Val
            195                 200                 205
Met Leu Ser Glu Ala Pro Phe Glu Pro Gln Gly Glu Gly Pro Leu Ala
            210                 215                 220
Leu Arg Arg Ala Gln Gly Ala Leu Leu Ala Tyr Ala Arg Ala Thr Gln
225                 230                 235                 240
Gly Gly Ala Leu Ser Val Arg Pro Phe Arg Leu Tyr Asp Pro Gly Ala
                245                 250                 255
Phe Val Arg Leu Pro Glu Ala Ser Leu Lys Ala Leu Glu Val Phe Glu
            260                 265                 270
Pro Leu Arg Gly Gln Asp Thr Leu Phe Gly Val Leu Asp Glu Thr Arg
            275                 280                 285
Thr Ala Pro Gly Arg Arg Leu Leu Gln Ala Trp Leu Arg His Pro Leu
            290                 295                 300
Leu Glu Arg Gly Pro Leu Glu Ala Arg Leu Asp Arg Val Glu Arg Phe
305                 310                 315                 320
Val Arg Glu Gly Ala Leu Arg Glu Gly Val Arg Arg Leu Leu Phe Arg
                325                 330                 335
Leu Ala Asp Leu Glu Arg Leu Ala Thr Arg Leu Glu Leu Ser Arg Ala
            340                 345                 350
Ser Pro Arg Asp Leu Ala Ala Leu Arg Arg Ser Leu Glu Ile Leu Pro
            355                 360                 365
Glu Leu Lys Gly Leu Leu Gly Glu Glu Val Gly Leu Pro Asp Leu Ser
            370                 375                 380
Gly Leu Leu Glu Glu Leu Arg Ala Ala Leu Val Glu Asp Pro Pro Leu
385                 390                 395                 400
Lys Val Ser Glu Gly Gly Leu Ile Arg Glu Gly Tyr Asp Pro Asp Leu
                405                 410                 415
Asp Ala Leu Arg Arg Ala His Ala Glu Gly Val Ala Tyr Phe Leu Asp
            420                 425                 430
Leu Glu Ala Arg Glu Lys Glu Arg Thr Gly Ile Pro Thr Leu Lys Val
            435                 440                 445
Gly Tyr Asn Ala Val Phe Gly Tyr Tyr Leu Glu Val Thr Arg Pro Tyr
            450                 455                 460
Tyr Glu Lys Val Pro Gln Glu Tyr Arg Pro Val Gln Thr Leu Lys Asp
465                 470                 475                 480
Arg Gln Arg Tyr Thr Leu Pro Glu Met Lys Glu Arg Glu Arg Glu Leu
                485                 490                 495
Tyr Arg Leu Glu Ala Leu Ile Lys Arg Glu Glu Glu Val Phe Leu
            500                 505                 510
Ala Leu Arg Glu Arg Ala Arg Lys Glu Ala Glu Ala Leu Arg Glu Ala
            515                 520                 525
Ala Arg Ile Leu Ala Glu Leu Asp Val Tyr Ala Ala Leu Ala Glu Val
            530                 535                 540
Ala Val Arg His Gly Tyr Thr Arg Pro Arg Phe Gly Glu Arg Leu Arg
545                 550                 555                 560
```

Ile Arg Ala Gly Arg His Pro Val Val Glu Arg Thr Ala Phe Val
                565                 570                 575

Pro Asn Asp Leu Glu Met Ala His Glu Leu Val Leu Thr Gly Pro
            580                 585                 590

Asn Met Ala Gly Lys Ser Thr Phe Leu Arg Gln Thr Ala Leu Ile Ala
        595                 600                 605

Leu Leu Ala Gln Ile Gly Ser Phe Val Pro Ala Glu Glu Ala Glu Leu
    610                 615                 620

Pro Leu Phe Asp Gly Ile Tyr Thr Arg Ile Gly Ala Ser Asp Asp Leu
625                 630                 635                 640

Ala Gly Gly Lys Ser Thr Phe Met Val Glu Met Glu Glu Val Ala Leu
                645                 650                 655

Val Leu Lys Glu Ala Thr Glu Arg Ser Leu Val Leu Leu Asp Glu Val
            660                 665                 670

Gly Arg Gly Thr Ser Ser Leu Asp Gly Val Ala Ile Ala Thr Ala Leu
        675                 680                 685

Ala Glu Ala Leu His Glu Arg Arg Cys Tyr Thr Leu Phe Ala Thr His
    690                 695                 700

Tyr Phe Glu Leu Thr Ala Leu Ala Leu Pro Arg Leu Lys Asn Leu His
705                 710                 715                 720

Val Ala Ala Lys Glu Glu Gly Gly Leu Val Phe Tyr His Gln Val
                725                 730                 735

Leu Pro Gly Pro Ala Ser Lys Ser Tyr Gly Val Glu Val Ala Glu Met
            740                 745                 750

Ala Gly Leu Pro Lys Glu Val Val Glu Arg Ala Arg Ala Leu Leu Ser
        755                 760                 765

Ala Met Ala Arg Arg Glu Gly Ala Leu Glu Glu Val Leu Glu Arg
    770                 775                 780

Leu Leu Ala Leu Asp Pro Asp Arg Leu Thr Pro Leu Glu Ala Leu Arg
785                 790                 795                 800

Phe Leu His Glu Leu Lys Ala Leu Ala Leu Gly Leu Pro Leu Gly Ser
                805                 810                 815

Met Lys Gly

<210> SEQ ID NO 16
<211> LENGTH: 3283
<212> TYPE: DNA
<213> ORGANISM: Thermus thermophilus

<400> SEQUENCE: 16

```
tctagaaggt ccttaaggcg cacccacgg aaggtgacgt tccccacccc acccgtttc      60
caggggttgc ccgaggtgcg gggctggaag agggaacgcc cgttgccgga gcactggagg   120
accatggtca cctcgtgctg gggaagctcg aggagctcct tggcctcaaa ggtgaagggt   180
ttgtccacca gtcccccac ctccaccttc cacccgtcca ggctggcccc ctccacggtg   240
ttgtagccgg ggaggtccac gttgttgcgg atgtagagga tctccttagg ggtgcgctcg   300
ggctggctga ccaagaggtc ataaggagtt ccaaaacga tggggcgttg ggagagaacc   360
aagagcttgg ggttttttccc cttcaccaac tggtcggccg tggggggcttg ctgggcgaag   420
cctcggcttc ccgcggccaa aagcgctgcc cctaggccca tgagcttcag gcgggttcgc   480
cggctgacgc tttccatacc ttatccctcc ctccaagggt ccgggggggac gtttgtcccc   540
actttccggt tgcccctaat ctaggtggca aacaacaccc atgtcaagtg ggggttaggg   600
```

-continued

| | | |
|---|---|---|
| ggtttttagc cccgtttaa ggggctagga gaaagcgcta atggggggt atggcggagt | 660 |
| taagatggaa ggcatgctca agggcgaagg cccaggtcca cttccccctc ttctgcagca | 720 |
| gtacgtggag ctccgcgacc gctacccgga ctacctcctc ctcttccagg tggggggactt | 780 |
| ctacgagtgc ttcggggagg acgccgagcg cctcgcccgc gcgcttggcc tcgtcctcac | 840 |
| ccacaagacc agcaaggact tcaccacccc catggcgggg atccccataa gggcctttga | 900 |
| cgcctacgcc gaaaggcttc ttaagatggg cttccgcctg gcggtggccg accaggtgga | 960 |
| gcctgccgag gaggcggaag gcctggtgcg tcgggaggtg acccagctcc tcaccccggg | 1020 |
| gaccctcacc caggaggccc tcctcccccg ggaggccaac tacctggccg ccatcgccac | 1080 |
| cggggacggg tggggtctgg cctttctgga cgtctccacg ggggagttca aggggaccct | 1140 |
| cctcaagagc aaaagtgccc tgtacgacga gcttttccgc caccggcccg ccgaggtcct | 1200 |
| tttggccccg gagctacggg agaacgaggc cttcgtggcc gagttccgga agcgctttcc | 1260 |
| cgtgatgctc tccgaggccc cctttgagcc ccaggggggag ggtcctttgg ccctgaggcg | 1320 |
| ggcccagggg gcgctccttg cctacgcccg ggccacccag ggggggcct tgagcgtgcg | 1380 |
| ccctttccgc ctctacgacc ccggggcctt cgtgcgccta ccgaggcga gcctgaaggc | 1440 |
| cctcgaggtc tttgaaccct tgcggggcca ggacaccctc tttggcgttc tggacgagac | 1500 |
| gcgaaccgcc cccggaagaa ggctcctcca ggcctggctc cgccacccc ttctggaaag | 1560 |
| gggggcccttg gaggcgaggc ttgaccgggt ggagcgcttc gtgcgggagg gggccctacg | 1620 |
| cgaggggggtg aggcgcctcc tcttccgcct cgccgacctg gagcgcctgg ccacgaggct | 1680 |
| ggagctttcc cggcaagcc cagggacct tgccgccta aggcggagcc tggagatcct | 1740 |
| ccccgagctt aagggcctttc tggggagga ggtgggggctt cccgacctct ccggccttttt | 1800 |
| ggaggagctt agggcggctt tggtggagga cccgcccctc aaggtctccg agggggggct | 1860 |
| catccgggag gggtacgacc cggacctgga cgccttgagg cgggcccacg ccgagggggt | 1920 |
| ggcctacttc ctggacctcg aggcccggga aaggagagg acgggcatcc ccaccctcaa | 1980 |
| ggtggggtac aacgccgtct tcggctacta cctggaggtg acccgcccct actacgagaa | 2040 |
| ggtgccccag gagtaccgcc ccgtccagac cctcaaggac cggcagcgct acaccctgcc | 2100 |
| ggagatgaag gaaaggggagc gggagctcta ccgcctcgag gccctgatca aaggcgcgga | 2160 |
| ggaggagtc ttccttgccc ttagggagcg ggcgaggaag gaggcggagg ccctaaggga | 2220 |
| ggcggcgagg atcctcgccg agcttgacgt ctacgccgcc ctcgccgagg tggcggtgcg | 2280 |
| ccacggctac acccggcccc gcttcgggga aaggcttcgg atcagggcgg ggcgccaccc | 2340 |
| ggtggtggag cgccgcaccg ccttcgtccc caacgacctg gagatggccc acgagctcgt | 2400 |
| cctcgtcacc gggcccaaca tggcggggaa gtccaccttc ctccgccaga ccgccctcat | 2460 |
| cgccctcctc gcccagatcg ggagcttcgt gcccgccgag gaggcggagc ttccctcttt | 2520 |
| tgacgggatc tacacgagga tcggggcctc ggacgacctc gccgggggga agagcacctt | 2580 |
| catggtggag atgaggagg tggccctggt gctcaaggag gccaccgaac gtagcctcgt | 2640 |
| cctcctggac gaggtgggcc ggggcacgag cagcctggac ggggtggcca tcgccaccgc | 2700 |
| cctcgccgag gccctgcacg agcggcggtg ctacaccctc ttcgccaccc actactttga | 2760 |
| gctcaccgcc ctcgcccttc cccggctcaa gaacctgcac gtggccgcca aggaggagga | 2820 |
| gggggggctc gtcttctacc accaggtcct ccccgggccc gcctccaaga gctacgggt | 2880 |
| ggaggtggcg gagatggcgg gcctgcccaa ggaggtggtg gagcgggccc cgcccctcct | 2940 |
| cagcgccatg gccgcgaggc gggagggcgc cctggaggag gtcttggagc gcctcctcgc | 3000 |

```
cttagacccc gaccgcctca ccccctcga ggccctgagg ttcctccacg agctcaaggc    3060
cttggccctg ggcctcccc tgggtagcat gaagggtga tccgcccct ccctccggag    3120 cttaggggcc tcctcgcccg gggcgaggtg ctccttacgg tgaaggacgc cgtgcgggag    3180
cttctggaaa acgccctgga cgctggggcc aggagggtgc gggtggagct tggggcggg    3240 gggcttaagc ggcttgtggt ggaggacgac ggggagggga tcc                    3283
```

<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence:Linker

<400> SEQUENCE: 17

```
Gly Ser Gly Pro Ser Pro Gly Ser
  1               5
```

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence:Linker

<400> SEQUENCE: 18

```
ggtagtggtc ctagtcctgg tagt                                           24
```

<210> SEQ ID NO 19
<211> LENGTH: 823
<212> TYPE: PRT
<213> ORGANISM: Homo sapiens

<400> SEQUENCE: 19

```
Met Asn Glu Asp Ser Asn Glu Glu Glu Ser Glu Asn Asp Trp
  1               5                  10                  15

Glu Glu Val Glu Glu Leu Ser Glu Pro Val Leu Gly Asp Val Arg Glu
                 20                  25                  30

Ser Thr Ala Phe Ser Arg Ser Leu Leu Pro Val Lys Pro Val Glu Ile
             35                  40                  45

Glu Ile Glu Thr Pro Glu Gln Ala Lys Thr Arg Glu Arg Ser Glu Lys
         50                  55                  60

Ile Lys Leu Glu Phe Glu Thr Tyr Leu Arg Arg Ala Met Lys Arg Phe
 65                  70                  75                  80

Asn Lys Gly Val His Glu Asp Thr His Lys Val His Leu Leu Cys Leu
                 85                  90                  95

Leu Ala Asn Gly Phe Tyr Arg Asn Asn Ile Cys Ser Gln Pro Asp Leu
            100                 105                 110

His Ala Ile Gly Leu Ser Ile Ile Pro Ala Arg Phe Thr Arg Val Leu
            115                 120                 125

Pro Arg Asp Val Asp Thr Tyr Tyr Leu Ser Asn Val Lys Trp Phe
        130                 135                 140

Ile Gly Thr Phe Thr Val Asn Ala Glu Leu Ser Ala Ser Glu Gln Asp
145                 150                 155                 160

Asn Leu Gln Thr Thr Leu Glu Arg Arg Phe Ala Ile Tyr Ser Ala Arg
                165                 170                 175

Asp Asp Glu Glu Leu Val His Ile Phe Leu Leu Ile Leu Arg Ala Leu
            180                 185                 190
```

-continued

```
Gln Leu Leu Thr Arg Leu Val Leu Ser Leu Gln Pro Ile Pro Leu Lys
        195                 200                 205

Ser Ala Thr Ala Lys Gly Lys Lys Pro Ser Lys Glu Arg Leu Thr Ala
210                 215                 220

Asp Pro Gly Gly Ser Ser Glu Thr Ser Ser Gln Val Leu Glu Asn His
225                 230                 235                 240

Thr Lys Pro Lys Thr Ser Lys Gly Thr Lys Gln Glu Thr Phe Ala
                    245                 250                 255

Lys Gly Thr Cys Arg Pro Ser Ala Lys Gly Arg Asn Lys Gly Gly
                260                 265                 270

Arg Lys Lys Arg Ser Lys Pro Ser Ser Glu Glu Asp Glu Gly Pro
        275                 280                 285

Gly Asp Lys Gln Glu Lys Ala Thr Gln Arg Arg Pro His Gly Arg Glu
290                 295                 300

Arg Arg Val Ala Ser Arg Val Ser Tyr Lys Glu Ser Gly Ser Asp
305                 310                 315                 320

Glu Ala Gly Ser Gly Ser Asp Phe Glu Leu Ser Ser Gly Glu Ala Ser
                325                 330                 335

Asp Pro Ser Asp Glu Asp Ser Glu Pro Gly Pro Lys Gln Arg Lys
                340                 345                 350

Ala Pro Ala Pro Gln Arg Thr Lys Ala Gly Ser Lys Ser Ala Ser Arg
        355                 360                 365

Thr His Arg Gly Ser His Arg Lys Asp Pro Ser Leu Pro Ala Ala Ser
        370                 375                 380

Ser Ser Ser Ser Ser Ser Lys Arg Gly Lys Lys Met Cys Ser Asp Gly
385                 390                 395                 400

Glu Lys Ala Glu Lys Arg Ser Ile Ala Gly Ile Asp Gln Trp Leu Glu
                405                 410                 415

Val Phe Cys Glu Gln Glu Glu Lys Trp Val Cys Val Asp Cys Val His
                420                 425                 430

Gly Val Val Gly Gln Pro Leu Thr Cys Tyr Lys Tyr Ala Thr Lys Pro
        435                 440                 445

Met Thr Tyr Val Val Gly Ile Asp Ser Asp Gly Trp Val Arg Asp Val
        450                 455                 460

Thr Gln Arg Tyr Asp Pro Val Trp Met Thr Val Thr Arg Lys Cys Arg
465                 470                 475                 480

Val Asp Ala Glu Trp Trp Ala Glu Thr Leu Arg Pro Tyr Gln Ser Pro
                485                 490                 495

Phe Met Asp Arg Glu Lys Lys Glu Asp Leu Glu Phe Gln Ala Lys His
                500                 505                 510

Met Asp Gln Pro Leu Pro Thr Ala Ile Gly Leu Tyr Lys Asn His Pro
        515                 520                 525

Leu Tyr Ala Leu Lys Arg His Leu Leu Lys Tyr Glu Ala Ile Tyr Pro
530                 535                 540

Glu Thr Ala Ala Ile Leu Gly Tyr Cys Arg Gly Glu Ala Val Tyr Ser
545                 550                 555                 560

Arg Asp Cys Val His Thr Leu His Ser Arg Asp Thr Trp Leu Lys Lys
                565                 570                 575

Ala Arg Val Val Arg Leu Gly Glu Val Pro Tyr Lys Met Val Lys Gly
                580                 585                 590

Phe Ser Asn Arg Ala Arg Lys Ala Arg Leu Ala Glu Pro Gln Leu Arg
                595                 600                 605
```

| | | | | | | | | | | | | |
|---|---|---|---|---|---|---|---|---|---|---|---|---|
|Glu|Glu|Asn|Asp|Leu|Gly|Leu|Phe|Gly|Tyr|Trp|Gln|Thr|Glu|Tyr|
| |610| | | | |615| | | | |620| | | |

Gln Pro Pro Val Ala Val Asp Gly Lys Val Pro Arg Asn Glu Phe Gly
625                 630                 635                 640

Asn Val Tyr Leu Phe Leu Pro Ser Met Met Pro Ile Gly Cys Val Gln
            645                 650                 655

Leu Asn Leu Pro Asn Leu His Arg Val Ala Arg Lys Leu Asp Ile Asp
        660                 665                 670

Cys Val Gln Ala Ile Thr Gly Phe Asp Phe His Gly Gly Tyr Ser His
    675                 680                 685

Pro Val Thr Asp Gly Tyr Ile Val Cys Glu Glu Phe Lys Asp Val Leu
    690                 695                 700

Leu Thr Ala Trp Glu Asn Glu Gln Ala Val Ile Glu Arg Lys Glu Lys
705                 710                 715                 720

Glu Lys Lys Glu Lys Arg Ala Leu Gly Asn Trp Lys Leu Leu Ala Lys
                725                 730                 735

Gly Leu Leu Ile Arg Glu Arg Leu Lys Arg Arg Tyr Gly Pro Lys Ser
            740                 745                 750

Glu Ala Ala Pro His Thr Asp Ala Gly Gly Leu Ser Ser Asp
    755                 760                 765

Glu Glu Glu Gly Thr Ser Ser Gln Ala Glu Ala Ala Arg Ile Leu Ala
    770                 775                 780

Ala Ser Trp Pro Gln Asn Arg Glu Asp Glu Lys Gln Lys Leu Lys
785                 790                 795                 800

Gly Gly Pro Lys Lys Thr Lys Arg Glu Lys Lys Ala Ala Ala Ser His
                805                 810                 815

Leu Phe Pro Phe Glu Lys Leu
            820

<210> SEQ ID NO 20
<211> LENGTH: 3455
<212> TYPE: DNA
<213> ORGANISM: Homo sapiens

<400> SEQUENCE: 20
gaaagaggaa aagaggctgc ggtcatcctg ggggttcagc agatggtcca gcaaaaaaga      60
aagtggccaa ggtgactgtt aaatctgaaa acctcaaggt tataaaggat gaagccctca     120
gcgatgggga tgacctcagg gactttccaa gtgacctcaa gaaggcacac catctgaaga     180 gagggggctac catgaatgaa gacagcaatg aagaagagga agaaagtgaa aatgattggg     240
aagaggttga agaacttagt gagcctgtgc tgggtgacgt gagagaaagt acagccttct     300
ctcgatctct tctgcctgtg aagccagtgg agatagagat tgaaacgcca gagcaggcga     360
agacaagaga aagaagtgaa aagataaaac tggagtttga acatatcttt cggagggcga     420
tgaaacgttt caataaaggg gtccatgagg acacacacaa ggttcacctt ctctgcctgc     480
tagcaaatgg cttctatcga aataacatct gcagccagcc agatctgcat gctattggcc     540
tgtccatcat cccagcccgc tttaccagag tgctgcctcg agatgtggac acctactacc     600
tctcaaacct ggtgaagtgg ttcattggaa catttacagt taatgcagaa ctttcagcca     660
gtgaacaaga taacctgcag actacattgg aaaggagatt tgctatttac tctgctcgag     720
atgatgagga attggtccat atattcttac tgattctccg ggctctgcag ctcttgaccc     780
ggctggtatt gtctctacag ccaattcctc tgaagtcagc aacagcaaag ggaaagaaac     840
cttccaagga aagattgact gcggatccag gaggctcctc agaaacttcc agccaagttc     900

-continued

```
tagaaaacca caccaaacca aagaccagca aaggaaccaa acaagaggaa acctttgcta      960
agggcacctg caggccaagt gccaaaggga agaggaacaa gggaggcaga aagaaacgga     1020
gcaagccctc ctccagcgag aagatgaggg cccaggagac aagcaggag aaggcaaccc      1080 agcgacgtcc gcatggccgg gagcggcggg tggcctccag ggtgtcttat aaagaggaga     1140
gtgggagtga tgaggctggc agcggctctg attttgagct ctccagtgga gaagcctctg     1200
atccctctga tgaggattcc gaacctggcc ctccaaagca gaggaaagcc cccgctcctc     1260
agaggacaaa ggctgggtcc aagagtgcct ccaggaccca tcgtgggagc catcgtaagg     1320
acccaagctt gccagcggca tcctcaagct cttcaagcag taaaagaggc aagaaaatgt     1380
gcagcgatgg tgaaaggca gaaaaaagaa gcatagctgg tatagaccag tggctagagg      1440
tgttctgtga gcaggaggaa aagtgggtat gtgtagactg tgtgcacggt gtggtgggcc     1500
agcctctgac ctgttacaag tacgccacca agcccatgac ctatgtggtg ggcattgaca     1560
gtgacggctg ggtccgagat gtcacacaga ggtacgaccc agtctggatg acagtgaccc     1620
gcaagtgccg ggttgatgct gagtggtggg ccgagacctt gagaccatac cagagcccat     1680
ttatggacag ggagaagaaa gaagacttgg agtttcaggc aaaacacatg gaccagcctt     1740
tgcccactgc cattggctta tataagaacc accctctgta tgccctgaag cggcatctcc     1800
tgaaatatga ggccatctat cccgagacag ctgccatcct tgggtattgt cgtggagaag     1860
cggtctactc cagggattgt gtgcacactc tgcattccag agacacgtgg ctgaagaaag     1920
caagagtggt gaggcttgga gaagtaccct acaagatggt gaaaggcttt tctaaccgtg     1980
ctcggaaagc ccgacttgct gagccccagc tgcgggaaga aaatgacctg ggcctgtttg     2040
gctactggca gacagaggag tatcagcccc cagtggccgt ggacgggaag gtgccccgga     2100
acgagtttgg gaatgtgtac ctcttcctgc ccagcatgat gcctattggc tgtgtccagc     2160
tgaacctgcc caatctacac cgcgtggccc gcaagctgga catcgactgt gtccaggcca     2220
tcactggctt tgatttccat ggcggctact cccatcccgt gactgatgga tacatcgtct     2280
gcgaggaatt caaagacgtg ctcctgactg cctgggaaaa tgagcaggca gtcattgaaa     2340
ggaaggagaa gggagaaaaag gagaagcggg ctctagggaa ctggaagttg ctggccaaag     2400
gtctgctcat caggagagg ctgaagcgtc gctacgggcc caagagtgag gcagcagctc      2460
cccacacaga tgcaggaggt ggactctctt ctgatgaaga ggaggggacc agctctcaag     2520
cagaagcggc caggatactg gctgcctcct ggcctcaaaa ccgagaagat gaagaaaagc     2580
agaagctgaa gggtgggccc aagaagacca aagggaaaa gaaagcagca gcttcccacc      2640
tgttcccatt tgagaagctg tgagctgagc gcccactaga ggggcaccca ccagttgctg     2700
ctgccccact acaggcccca cacctgccct gggcatgccc agcccctggt ggtgggggct     2760
tctctgctga gaaggcaaac tgaggcagca tgcacggagc cggggtcagg ggagacgagg     2820
ccaagctgag gaggtgctgc aggtcccgtc tggctccagc ccttgtcaga ttcacccagg     2880
gtgaagcctt caaagctttt tgctaccaaa gcccactcac cctttgagct acagaacact     2940
ttgctaggag atactcttct gcctcctaga cctgttcttt ccatctttag aaacatcagt     3000
ttttgtatga aagccaccgg gagatttctg gatggtggtg catccgtgaa tgcgctgatc     3060
gtttcttcca gttagagtct tcatctgtcc gacaagttca ctcgcctcgg ttgcggacct     3120
aggaccattt ctctgcaggc cacttacctt ccctgagtc aggcttacta atgctgccct      3180
cactgcctct ttgcagtagg ggagagagca gagaagtaca ggtcatctgc tgggatctag     3240
```

-continued

```
ttttccaagt aacattttgt ggtgacagaa gcctaaaaaa agctaaaatc aggaaagaaa    3300
aggaaaaata cgaattgaaa attaaggaaa tgttagtaaa atagatcagt gttaaactag    3360
attgtattca ttactagata aaatgtataa agctctctgt actaaggaga aatgactttt    3420 ataacattt gagaaaataa taaagcattt atcta                                3455
```

<210> SEQ ID NO 21
<211> LENGTH: 1140
<212> TYPE: PRT
<213> ORGANISM: Homo sapiens

<400> SEQUENCE: 21

```
Met Ser Tyr Asn Tyr Val Val Thr Ala Gln Lys Pro Thr Ala Val Asn
  1               5                  10                  15

Gly Cys Val Thr Gly His Phe Thr Ser Ala Glu Asp Leu Asn Leu Leu
                 20                  25                  30

Ile Ala Lys Asn Thr Arg Leu Glu Ile Tyr Val Val Thr Ala Glu Gly
             35                  40                  45

Leu Arg Pro Val Lys Glu Val Gly Met Tyr Gly Lys Ile Ala Val Met
 50                  55                  60

Glu Leu Phe Arg Pro Lys Gly Glu Ser Lys Asp Leu Leu Phe Ile Leu
 65                  70                  75                  80

Thr Ala Lys Tyr Asn Ala Cys Ile Leu Glu Tyr Lys Gln Ser Gly Glu
                 85                  90                  95

Ser Ile Asp Ile Ile Thr Arg Ala His Gly Asn Val Gln Asp Arg Ile
            100                 105                 110

Gly Arg Pro Ser Glu Thr Gly Ile Ile Gly Ile Ile Asp Pro Glu Cys
        115                 120                 125

Arg Met Ile Gly Leu Arg Leu Tyr Asp Gly Leu Phe Lys Val Ile Pro
130                 135                 140

Leu Asp Arg Asp Asn Lys Glu Leu Lys Ala Phe Asn Ile Arg Leu Glu
145                 150                 155                 160

Glu Leu His Val Ile Asp Val Lys Phe Leu Tyr Gly Cys Gln Ala Pro
                165                 170                 175

Thr Ile Cys Phe Val Tyr Gln Asp Pro Gln Gly Arg His Val Lys Thr
            180                 185                 190

Tyr Glu Val Ser Leu Arg Glu Lys Glu Phe Asn Lys Gly Pro Trp Lys
        195                 200                 205

Gln Glu Asn Val Glu Ala Glu Ala Ser Met Val Ile Ala Val Pro Glu
    210                 215                 220

Pro Phe Gly Gly Ala Ile Ile Ile Gly Gln Glu Ser Ile Thr Tyr His
225                 230                 235                 240

Asn Gly Asp Lys Tyr Leu Ala Ile Ala Pro Pro Ile Ile Lys Gln Ser
                245                 250                 255

Thr Ile Val Cys His Asn Arg Val Asp Pro Asn Gly Ser Arg Tyr Leu
            260                 265                 270

Leu Gly Asp Met Glu Gly Arg Leu Phe Met Leu Leu Leu Glu Lys Glu
        275                 280                 285

Glu Gln Met Asp Gly Thr Val Thr Leu Lys Asp Leu Arg Val Glu Leu
    290                 295                 300

Leu Gly Glu Thr Ser Ile Ala Glu Cys Leu Thr Tyr Leu Asp Asn Gly
305                 310                 315                 320

Val Val Phe Val Gly Ser Arg Leu Gly Asp Ser Gln Leu Val Lys Leu
                325                 330                 335
```

-continued

```
Asn Val Asp Ser Asn Glu Gln Gly Ser Tyr Val Val Ala Met Glu Thr
            340                 345                 350

Phe Thr Asn Leu Gly Pro Ile Val Asp Met Cys Val Val Asp Leu Glu
            355                 360                 365

Arg Gln Gly Gln Gly Gln Leu Val Thr Cys Ser Gly Ala Phe Lys Glu
            370                 375                 380

Gly Ser Leu Arg Ile Ile Arg Asn Gly Ile Gly Ile His Glu His Ala
385                 390                 395                 400

Ser Ile Asp Leu Pro Gly Ile Lys Gly Leu Trp Pro Leu Arg Ser Asp
            405                 410                 415

Pro Asn Arg Glu Thr Tyr Asp Thr Leu Val Leu Ser Phe Val Gly Gln
            420                 425                 430

Thr Arg Val Leu Met Leu Asn Gly Glu Val Glu Thr Glu Leu
            435                 440                 445

Met Gly Phe Val Asp Asp Gln Gln Thr Phe Phe Cys Gly Asn Val Ala
            450                 455                 460

His Gln Gln Leu Ile Gln Ile Thr Ser Ala Ser Val Arg Leu Val Ser
465                 470                 475                 480

Gln Glu Pro Lys Ala Leu Val Ser Glu Trp Lys Glu Pro Gln Ala Lys
            485                 490                 495

Asn Ile Ser Val Ala Ser Cys Asn Ser Ser Gln Val Val Ala Val
            500                 505                 510

Gly Arg Ala Leu Tyr Tyr Leu Gln Ile His Pro Gln Glu Leu Arg Gln
            515                 520                 525

Ile Ser His Thr Glu Met Glu His Glu Val Ala Cys Leu Asp Ile Thr
            530                 535                 540

Pro Leu Gly Asp Ser Asn Gly Leu Ser Pro Leu Cys Ala Ile Gly Leu
545                 550                 555                 560

Trp Thr Asp Ile Ser Ala Arg Ile Leu Lys Leu Pro Ser Phe Glu Leu
            565                 570                 575

Leu His Lys Glu Met Leu Gly Gly Glu Ile Ile Pro Arg Ser Ile Leu
            580                 585                 590

Met Thr Thr Phe Glu Ser Ser His Tyr Leu Leu Cys Ala Leu Gly Asp
            595                 600                 605

Gly Ala Leu Phe Tyr Phe Gly Leu Asn Ile Glu Thr Gly Leu Leu Ser
            610                 615                 620

Asp Arg Lys Lys Val Thr Leu Gly Thr Gln Pro Thr Val Leu Arg Thr
625                 630                 635                 640

Phe Arg Ser Leu Ser Thr Thr Asn Val Phe Ala Cys Ser Asp Arg Pro
            645                 650                 655

Thr Val Ile Tyr Ser Ser Asn His Lys Leu Val Phe Ser Asn Val Asn
            660                 665                 670

Leu Lys Glu Val Asn Tyr Met Cys Pro Leu Asn Ser Asp Gly Tyr Pro
            675                 680                 685

Asp Ser Leu Ala Leu Ala Asn Asn Ser Thr Leu Thr Ile Gly Thr Ile
            690                 695                 700

Asp Glu Ile Gln Lys Leu His Ile Arg Thr Val Pro Leu Tyr Glu Ser
705                 710                 715                 720

Pro Arg Lys Ile Cys Tyr Gln Glu Val Ser Gln Cys Phe Gly Val Leu
            725                 730                 735

Ser Ser Arg Ile Glu Val Gln Asp Thr Ser Gly Gly Thr Thr Ala Leu
            740                 745                 750

Arg Pro Ser Ala Ser Thr Gln Ala Leu Ser Ser Ser Val Ser Ser Ser
```

```
                755                 760                 765
Lys Leu Phe Ser Ser Thr Ala Pro His Glu Thr Ser Phe Gly Glu
    770                 775                 780

Glu Val Glu Val His Asn Leu Leu Ile Ile Asp Gln His Thr Phe Glu
785                 790                 795                 800

Val Leu His Ala His Gln Phe Leu Gln Asn Glu Tyr Ala Leu Ser Leu
                805                 810                 815

Val Ser Cys Lys Leu Gly Lys Asp Pro Asn Thr Tyr Phe Ile Val Gly
            820                 825                 830

Thr Ala Met Val Tyr Pro Glu Ala Glu Pro Lys Gln Gly Arg Ile
            835                 840                 845

Val Val Phe Gln Tyr Ser Asp Gly Lys Leu Gln Thr Val Ala Glu Lys
    850                 855                 860

Glu Val Lys Gly Ala Val Tyr Ser Met Val Glu Phe Asn Gly Lys Leu
865                 870                 875                 880

Leu Ala Ser Ile Asn Ser Thr Val Arg Leu Tyr Glu Trp Thr Thr Glu
                885                 890                 895

Lys Asp Val Arg Thr Glu Cys Asn His Tyr Asn Asn Ile Met Ala Leu
            900                 905                 910

Tyr Leu Lys Thr Lys Gly Asp Phe Ile Leu Val Gly Asp Leu Met Arg
        915                 920                 925

Ser Val Leu Leu Ala Tyr Lys Pro Met Glu Gly Asn Phe Glu Glu
    930                 935                 940

Ile Ala Arg Asp Phe Asn Pro Asn Trp Met Ser Ala Val Glu Ile Leu
945                 950                 955                 960

Asp Asp Asp Asn Phe Leu Gly Ala Glu Asn Ala Phe Asn Leu Phe Val
                965                 970                 975

Cys Gln Lys Asp Ser Ala Ala Thr Thr Asp Glu Glu Arg Gln His Leu
            980                 985                 990

Gln Glu Val Gly Leu Phe His Leu Gly Glu Phe Val Asn Val Phe Cys
        995                 1000                1005

His Gly Ser Leu Val Met Gln Asn Leu Gly Glu Thr Ser Thr Pro Thr
    1010                1015                1020

Gln Gly Ser Val Leu Phe Gly Thr Val Asn Gly Met Ile Gly Leu Val
1025                1030                1035                1040

Thr Ser Leu Ser Glu Ser Trp Tyr Asn Leu Leu Asp Met Gln Asn
                1045                1050                1055

Arg Leu Asn Lys Val Ile Lys Ser Val Gly Lys Ile Glu His Ser Phe
            1060                1065                1070

Trp Arg Ser Phe His Thr Glu Arg Lys Thr Glu Pro Ala Thr Gly Phe
        1075                1080                1085

Ile Asp Gly Asp Leu Ile Glu Ser Phe Leu Asp Ile Ser Arg Pro Lys
    1090                1095                1100

Met Gln Glu Val Val Ala Asn Leu Gln Tyr Asp Asp Gly Ser Gly Met
1105                1110                1115                1120

Lys Arg Glu Ala Thr Ala Asp Asp Leu Ile Lys Val Val Glu Glu Leu
                1125                1130                1135

Thr Arg Ile His
            1140

<210> SEQ ID NO 22
<211> LENGTH: 4221
<212> TYPE: DNA
<213> ORGANISM: Homo sapiens
```

<400> SEQUENCE: 22

```
cagcggcagt ggagttcgct gcgcgctgtt gggggccacc tgtcttttcg cttgtgtccc      60
tctttctagt gtcgcgctcg agtcccgacg ggccgctcca agcctcgaca tgtcgtacaa     120
ctacgtggta acggcccaga agcccaccgc cgtgaacggc tgcgtgaccg gacactttac     180
ttcggccgaa gacttaaacc tgttgattgc caaaaacacg agattagaga tctatgtggt     240
caccgccgag gggcttcggc ccgtcaaaga ggtgggcatg tatgggaaga ttgcggtcat     300
ggagcttttc aggcccaagg gggagagcaa ggacctgctg tttatcttga cagcgaagta     360
caatgcctgc atcctggagt ataaacagag tggcgagagc attgacatca ttacgcgagc     420
ccatggcaat gtccaggacc gcattggccg cccctcagag accggcatta ttggcatcat     480
tgaccctgag tgccggatga ttggcctgcg tctctatgat ggccttttca aggttattcc     540
actagatcgc gataataaag aactcaaggc cttcaacatc cgcctggagg agctgcatgt     600
cattgatgtc aagttcctat atggttgcca agcacctact atttgctttg tctaccagga     660
ccctcagggg cggcacgtaa aaacctatga ggtgtctctc cgagaaaagg aattcaataa     720
gggcccttgg aaacaggaaa atgtcgaagc tgaagcttcc atggtgatcg cagtcccaga     780
gcccttgggg ggggccatca tcattggaca ggagtcaatc acctatcaca atggtgacaa     840
atacctggct attgccctc ctatcatcaa gcaaagcacg attgtgtgcc acaatcgagt     900
ggaccctaat ggctcaagat acctgctggg agacatggaa ggccggctct tcatgctgct     960
tttggagaag gaggaacaga tggatggcac cgtcactctc aaggatctcc gtgtagaact    1020
ccttggagag acctctattg ctgagtgctt gacataccttt gataatggtg ttgtgtttgt    1080
cgggtctcgc ctgggtgact cccagcttgt gaagctcaac gttgacagta atgaacaagg    1140
ctccatatgta gtggccatgg aaaccttac caacttagga cccattgtcg atatgtgcgt    1200
ggtggacctg gagaggcagg ggcaggggca gctggtcact tgctctgggg ctttcaagga    1260
aggttctttg cggatcatcc ggaatggaat tggaatccac gagcatgcca gcattgactt    1320
accaggcatc aaaggattat ggccactgcg gtctgaccct aatcgtgaga cttatgacac    1380
tttggtgctc tcttttgtgg gccagacaag agttctcatg ttaaatggag aggaggtaga    1440
agaaaccgaa ctgatgggtt tcgtggatga tcagcagact ttcttctgtg gcaacgtggc    1500
tcatcagcag cttatccaga tcacttcagc atcggtgagg ttggtctctc aagaacccaa    1560
agctctggtc agtgaatgga aggagcctca ggccaagaac atcagtgtgg cctcctgcaa    1620
tagcagccag gtggtggtgg ctgtaggcag ggccctctac tatctgcaga tccatcctca    1680
ggagctccgg cagatcagcc acacagagat ggaacatgaa gtggcttgct tggacatcac    1740
cccattagga gacagcaatg gactgtcccc tctttgtgcc attggcctct ggacggacat    1800
ctcggctcgt atcttgaagt tgccctcttt tgaactactg cacaaggaga tgctgggtgg    1860
agagatcatt cctcgctcca tcctgatgac cacctttgag agtagccatt acctcctttg    1920
tgccttggga gatggagcgc ttttctactt tgggctcaac attgagacag tctgttgag    1980
cgaccgtaag aaggtgactt tgggcaccca gcccaccgta ttgaggactt ttcgttctct    2040
ttctaccacc aacgtctttg cttgttctga ccgccccact gtcatctata gcagcaacca    2100
caaattggtc ttctcaaatg tcaacctcaa ggaagtgaac tacatgtgtc cctcaattc     2160
agatggctat cctgacagcc tggcgctggc caacaatagc ccctcacca ttggcaccat    2220
cgatgagatc cagaagctgc acattcgcac agttccctc tatgagtctc caaggaagat    2280
```

-continued

```
ctgctaccag gaagtgtccc agtgtttcgg ggtcctctcc agccgcattg aagtccaaga    2340
cacgagtggg ggcacgacag ccttgaggcc cagcgctagc acccaggctc tgtccagcag    2400
tgtaagctcc agcaagctgt tctccagcag cactgctcct catgagacct cctttggaga    2460
agaggtggag gtgcataacc tacttatcat tgaccaacac acctttgaag tgcttcatgc    2520
ccaccagttt ctgcagaatg aatatgccct cagtctggtt tcctgcaagc tgggcaaaga    2580
ccccaacact tacttcattg tgggcacagc aatggtgtat cctgaagagg cagagcccaa    2640
gcagggtcgc attgtggtct ttcagtattc ggatggaaaa ctacagactg tggctgaaaa    2700
ggaagtgaaa ggggccgtgt actctatggt ggaatttaac gggaagctgt tagccagcat    2760
caatagcacg gtgcggctct atgagtggac aacagaaag gacgtgcgca ctgagtgcaa    2820
ccactacaac aacatcatgg ccctctacct gaagaccaag ggcgacttca tcctggtggg    2880
cgaccttatg cgctcagtgc tgctgcttgc ctacaagccc atggaaggaa actttgaaga    2940
gattgctcga gactttaatc ccaactggat gagtgctgtg gaaatcttgg atgatgacaa    3000
ttttctgggg gctgaaaatg cctttaactt gtttgtgtgt caaaaggata gcgctgccac    3060
cactgacgag gagcggcagc acctccagga ggttggtctt ttccacctgg gcgagtttgt    3120
caatgtcttt tgccacggct ctctggtaat gcagaatctg ggtgagactt ccaccccccac   3180 acaaggctcg gtgctcttcg gcacggtcaa cggcatgata gggctggtga cctcactgtc    3240
agagagctgg tacaacctcc tgctggacat gcagaatcga ctcaataaag tcatcaaaag    3300
tgtggggaag atcgagcact ccttctggag atcctttcac accgagcgga agacagaacc    3360
agccacaggt ttcatcgacg gtgacttgat tgagagtttc ctggatatta gccgcccaa     3420 gatgcaggag gtggtggcaa acctacagta tgacgatggc agcggtatga agcgagaggc    3480
cactgcagac gacctcatca aggttgtgga ggagctaact cggatccatt agccaagggc    3540
aggggccccc tttgctgacc ctccccaaag gctttgccct gctgccctcc cctcctctc    3600 caccatcgtc ttcttggcca tgggaggcct ttccctaagc cagctgcccc cagagccaca    3660
gttcccctat gtggaagtgg ggcgggcttc atagagactt gggaatgagc tgaaggtgaa    3720
acattttctc cctggatttt taccagtctc acatgattcc agccatcacc ttagaccacc    3780
aagccttgat tggtgttgcc agttgtcctc cttccgggga aggattttgc agttcttgg     3840 ctgaaaggaa gctgtgcgtg tgtgtgtgtg tatgtgtgtg tgtgtatgtg tatctcacac    3900
tcatgcattg tcctcttttt atttagattg gcagtgtagg gagttgtggg tagtggggaa    3960
gagggttagg agggtttcat tgtctgtgaa gtgagacctt ccttttactt ttcttctatt    4020
gcctctgaga gcatcaggcc tagaggcctg actgccaagc catgggtagc ctgggtgtaa    4080
aacctggaga tggtggatga tccccacgcc acagcccttt tgtctctgca aactgccttc    4140
ttcggaaaga agaaggtggg aggatgtgaa ttgttagttt ctgagttta ccaaataaag      4200 tagaatataa gaagaaaaaa a                                               4221
```

<210> SEQ ID NO 23
<211> LENGTH: 269
<212> TYPE: PRT
<213> ORGANISM: Escherichia coli

<400> SEQUENCE: 23

```
Met Pro Glu Leu Pro Glu Val Glu Thr Ser Arg Arg Gly Ile Glu Pro
  1               5                  10                  15

His Leu Val Gly Ala Thr Ile Leu His Ala Val Val Arg Asn Gly Arg
             20                  25                  30
```

```
Leu Arg Trp Pro Val Ser Glu Glu Ile Tyr Arg Leu Ser Asp Gln Pro
        35                  40                  45
Val Leu Ser Val Gln Arg Arg Ala Lys Tyr Leu Leu Leu Glu Leu Pro
    50                  55                  60
Glu Gly Trp Ile Ile Ile His Leu Gly Met Ser Gly Ser Leu Arg Ile
65                  70                  75                  80
Leu Pro Glu Glu Leu Pro Pro Glu Lys His Asp His Val Asp Leu Val
                85                  90                  95
Met Ser Asn Gly Lys Val Leu Arg Tyr Thr Asp Pro Arg Arg Phe Gly
            100                 105                 110
Ala Trp Leu Trp Thr Lys Glu Leu Glu Gly His Asn Val Leu Thr His
        115                 120                 125
Leu Gly Pro Glu Pro Leu Ser Asp Asp Phe Asn Gly Glu Tyr Leu His
    130                 135                 140
Gln Lys Cys Ala Lys Lys Thr Ala Ile Lys Pro Trp Leu Met Asp
145                 150                 155                 160
Asn Lys Leu Val Val Gly Val Gly Asn Ile Tyr Ala Ser Glu Ser Leu
                165                 170                 175
Phe Ala Ala Gly Ile His Pro Asp Arg Leu Ala Ser Ser Leu Ser Leu
            180                 185                 190
Ala Glu Cys Glu Leu Leu Ala Arg Val Ile Lys Ala Val Leu Leu Arg
        195                 200                 205
Ser Ile Glu Gln Gly Gly Thr Thr Leu Lys Asp Phe Leu Gln Ser Asp
    210                 215                 220
Gly Lys Pro Gly Tyr Phe Ala Gln Glu Leu Gln Val Tyr Gly Arg Lys
225                 230                 235                 240
Gly Glu Pro Cys Arg Val Cys Gly Thr Pro Ile Val Ala Thr Lys His
                245                 250                 255
Ala Gln Arg Ala Thr Phe Tyr Cys Arg Gln Cys Gln Lys
            260                 265

<210> SEQ ID NO 24
<211> LENGTH: 1093
<212> TYPE: DNA
<213> ORGANISM: Escherichia coli

<400> SEQUENCE: 24
gatctacaaa gaagcgaaaa tcaaataatt ctcgctttga tgtaacaaaa aaacctcgct      60
ccggcggggt ttttgttatc tgcttgcccc catattgact gcatctgttc attcctggag    120
atgctatgcc tgaattaccc gaagttgaaa ccagccgccg cggcatagaa ccgcatctcg    180
ttggtgcaac cattcttcat gcagtggtgc gcaacggacg cttgcgctgg ccggtttcag    240
aagagatcta ccgtttaagc gaccaaccag tgcttagcgt gcagcggcgg gctaaatatc    300
tgctgctgga gctgcctgag ggctggatta tcattcattt agggatgtct ggcagcctgc    360
gcatccttcc agaagaactt cccctgaaa agcatgacca tgtggatttg gtgatgagca    420
acggcaaagt gctgcgctac accgatccgc gccgctttgg tgcctggctg tggaccaaag    480
agctggaagg gcataatgtg ctgacccatc ttggaccgga gccgcttagc gacgatttca    540
atggtgagta tctgcatcag aagtgcgcga agaaaaaaac ggcgattaaa ccgtggctga    600
tggataacaa gctggtggta ggggtaggga atatctatgc cagcgaatca ctgtttgcgg    660
cggggatcca tccggatcgg ctggcgtcat cactgtcgct ggcagagtgt gaattgttag    720
ctcgggtgat taaagcggtg ttgctgcgtt cgattgagca gggtggtaca acgctgaaag    780
```

```
attttctgca aagtgatggt aaaccgggct atttcgctca ggaattgcag gtttacgggc      840
gaaaaggtga gccgtgtcgg gtgtgcggta cgccgattgt ggcgactaaa catgcgcagc      900
gggcaacgtt ttattgtcgg cagtgccaga agtaattcat gcgcgccgga tggcatacca      960
tccggcataa acgctacgct aacttcgcca tcagcgcctg atggacattc tccggcagga     1020
aatgggtgac atcgccctga tggcgcgcca cctctttcac caacgatgaa gagataaacg     1080
accactcttt cga                                                        1093
```

<210> SEQ ID NO 25
<211> LENGTH: 211
<212> TYPE: PRT
<213> ORGANISM: Escherichia coli

<400> SEQUENCE: 25

```
Met Asn Lys Ala Lys Arg Leu Glu Ile Leu Thr Arg Leu Arg Glu Asn
 1               5                  10                  15

Asn Pro His Pro Thr Thr Glu Leu Asn Phe Ser Ser Pro Phe Glu Leu
            20                  25                  30

Leu Ile Ala Val Leu Leu Ser Ala Gln Ala Thr Asp Val Ser Val Asn
        35                  40                  45

Lys Ala Thr Ala Lys Leu Tyr Pro Val Ala Asn Thr Pro Ala Ala Met
    50                  55                  60

Leu Glu Leu Gly Val Glu Gly Val Lys Thr Tyr Ile Lys Thr Ile Gly
65                  70                  75                  80

Leu Tyr Asn Ser Lys Ala Glu Asn Ile Ile Lys Thr Cys Arg Ile Leu
                85                  90                  95

Leu Glu Gln His Asn Gly Glu Val Pro Glu Asp Arg Ala Ala Leu Glu
            100                 105                 110

Ala Leu Pro Gly Val Gly Arg Lys Thr Ala Asn Val Val Leu Asn Thr
        115                 120                 125

Ala Phe Gly Trp Pro Thr Ile Ala Val Asp Thr His Ile Phe Arg Val
    130                 135                 140

Cys Asn Arg Thr Gln Phe Ala Pro Gly Lys Asn Val Glu Gln Val Glu
145                 150                 155                 160

Glu Lys Leu Leu Lys Val Val Pro Ala Glu Phe Lys Val Asp Cys His
                165                 170                 175

His Trp Leu Ile Leu His Gly Arg Tyr Thr Cys Ile Ala Arg Lys Pro
            180                 185                 190

Arg Cys Gly Ser Cys Ile Ile Glu Asp Leu Cys Glu Tyr Lys Glu Lys
        195                 200                 205

Val Asp Ile
    210
```

<210> SEQ ID NO 26
<211> LENGTH: 780
<212> TYPE: DNA
<213> ORGANISM: Escherichia coli

<400> SEQUENCE: 26

```
acctgattga tgaaagaatg aaaaagcgcc gtgctgaagc agctgcagaa cgtgcattgc       60
caacggtgaa acagggaatg tctgatgaat aaagcaaaac gcctggagat cctcactcgc      120
ctgcgtgaga acaatcctca tcccaccacc gagcttaatt tcagttcgcc ttttgaattg      180
ctgattgccg tactgctttc cgctcaggcg accgatgtca gtgttaataa ggcgacggcg      240
```

-continued

```
aaactctacc cggtggcgaa tacgcctgca gcgatgcttg aactgggcgt tgaagggtg      300
aaaacctata tcaaaacgat tgggctttat aacagcaaag cagaaaatat catcaaaacc     360
tgccgtatct tgctggagca gcataatggc gaggttccgg aagatcgtgc tgcgcttgaa     420
gccctgcccg gcgtaggtcg taaaacagcc aacgtcgtat taaacactgc attcggctgg    480
ccgactattg ctgtcgacac gcacattttc cgcgtttgta atcgtactca atttgccccg    540
gggaaaaacg tcgaacaggt agaagaaaag ctactgaaag tggttccagc agagtttaaa    600
gtcgactgcc accattggtt gatcctgcac gggcgttata cctgcattgc ccgcaagccc    660
cgctgtggct cttgtattat tgaagatctt tgtgaataca agagaaagt tgacatctga    720
agaaaagggg taacaccgat taccccattg ataacctttc tttatcctct tttaaaacat    780
```

<210> SEQ ID NO 27
<211> LENGTH: 263
<212> TYPE: PRT
<213> ORGANISM: Escherichia coli

<400> SEQUENCE: 27

```
Met Pro Glu Gly Pro Glu Ile Arg Arg Ala Ala Asp Asn Leu Glu Ala
 1               5                  10                  15
Ala Ile Lys Gly Lys Pro Leu Thr Asp Val Trp Phe Ala Phe Pro Gln
             20                  25                  30
Leu Lys Pro Tyr Gln Ser Gln Leu Ile Gly Gln His Val Thr His Val
         35                  40                  45
Glu Thr Arg Gly Lys Ala Leu Leu Thr His Phe Ser Asn Asp Leu Thr
     50                  55                  60
Leu Tyr Ser His Asn Gln Leu Tyr Gly Val Trp Arg Val Val Asp Thr
 65                  70                  75                  80
Gly Glu Glu Pro Gln Thr Thr Arg Val Leu Arg Val Lys Leu Gln Thr
                 85                  90                  95
Ala Asp Lys Thr Ile Leu Leu Tyr Ser Ala Ser Asp Ile Glu Met Leu
            100                 105                 110
Thr Pro Glu Gln Leu Thr Thr His Pro Phe Leu Gln Arg Val Gly Pro
        115                 120                 125
Asp Val Leu Asp Pro Asn Leu Thr Pro Glu Val Val Lys Glu Arg Leu
    130                 135                 140
Leu Ser Pro Arg Phe Arg Asn Arg Gln Phe Ala Gly Leu Leu Leu Asp
145                 150                 155                 160
Gln Ala Phe Leu Ala Gly Leu Gly Asn Tyr Leu Arg Val Glu Ile Leu
                165                 170                 175
Trp Gln Val Gly Leu Thr Gly Asn His Lys Ala Lys Asp Leu Asn Ala
            180                 185                 190
Ala Gln Leu Asp Ala Leu Ala His Ala Leu Leu Glu Ile Pro Arg Phe
        195                 200                 205
Ser Tyr Ala Thr Arg Gly Gln Val Asp Glu Asn Lys His His Gly Ala
    210                 215                 220
Leu Phe Arg Phe Lys Val Phe His Arg Asp Gly Glu Pro Cys Glu Arg
225                 230                 235                 240
Cys Gly Ser Ile Ile Glu Lys Thr Thr Leu Ser Ser Arg Pro Phe Tyr
                245                 250                 255
Trp Cys Pro Gly Cys Gln His
            260
```

<210> SEQ ID NO 28

<211> LENGTH: 1030
<212> TYPE: DNA
<213> ORGANISM: Escherichia coli

<400> SEQUENCE: 28

```
gcctgcatgg cgacggcgag cacgcactgg cgttcgcccg ccgactacgc tctgcatttg    60
ccgaaaaggg gattgttgtc gcagcataac cccgattaat aaagaatgaa aaaggatat   120
caccatgcct gaaggcccgg agatccgccg tgcagcggat aacctggagg cggcgatcaa   180
aggcaaacca ctaactgatg tctggtttgc cttcccgcag ttaaaacctt atcaatcaca   240
acttatcggt caacacgtta cccatgtgga aacgcgtggt aaggcgttgt taactcattt   300
ttccaacgac ttaacgctct acagccataa tcagctttac ggcgtctggc gcgtggttga   360
taccggcgaa gagccgcaga ccacgcgagt attgcgggta aaactgcaaa cggctgacaa   420
aaccattctg ctttatagcg cctcggatat tgagatgttg accccggaac aactgaccac   480
gcatccgttt ttacaacgcg ttggtcccga tgtgctggat ccgaatctga cgccggaggt   540
ggtgaaagaa cgattattgt cgccgcgctt tcgtaaccgt cagtttgctg gattactgct   600
cgatcaggcg tttctggctg gcttggcaa ttatttgcgg gtggagatcc tctggcaggt   660
tgggttgact ggaaatcata aagcgaaaga tctcaatgcg gcgcaactgg atgcactcgc   720
acacgcgtta ctggagattc ctcgattttc ctacgctacg cggggggcagg tggatgagaa   780
taagcatcat ggggcgctgt ttcgctttaa ggttttcat cgagatggcg aaccgtgcga   840
acgttgtggc agcatcattg agaaaaccac gctgtcatct cgcccgtttt actggtgccc   900
tggctgccag cactaggccg accgcttcgg cgcataggtt gaaataaacc gcgcaatggc   960
aggccctgtc agcaaaatac tgaacaggcg tagggtttgc atcgccataa tgagcgccag  1020
acctgcaggc                                                        1030
```

<210> SEQ ID NO 29
<211> LENGTH: 268
<212> TYPE: PRT
<213> ORGANISM: Escherichia coli

<400> SEQUENCE: 29

```
Met Lys Phe Val Ser Phe Asn Ile Asn Gly Leu Arg Ala Arg Pro His
 1               5                  10                  15

Gln Leu Glu Ala Ile Val Glu Lys His Gln Pro Asp Val Ile Gly Leu
            20                  25                  30

Gln Glu Thr Lys Val His Asp Asp Met Phe Pro Leu Glu Glu Val Ala
        35                  40                  45

Lys Leu Gly Tyr Asn Val Phe Tyr His Gly Gln Lys Gly His Tyr Gly
    50                  55                  60

Val Ala Leu Leu Thr Lys Glu Thr Pro Ile Ala Val Arg Arg Gly Phe
65                  70                  75                  80

Pro Gly Asp Asp Glu Glu Ala Gln Arg Arg Ile Ile Met Ala Glu Ile
                85                  90                  95

Pro Ser Leu Leu Gly Asn Val Thr Val Ile Asn Gly Tyr Phe Pro Gln
            100                 105                 110

Gly Glu Ser Arg Asp His Pro Ile Lys Phe Pro Ala Lys Ala Gln Phe
        115                 120                 125

Tyr Gln Asn Leu Gln Asn Tyr Leu Glu Thr Glu Leu Lys Arg Asp Asn
    130                 135                 140

Pro Val Leu Ile Met Gly Asp Met Asn Ile Ser Pro Thr Asp Leu Asp
145                 150                 155                 160
```

Ile Gly Ile Gly Glu Glu Asn Arg Lys Arg Trp Leu Arg Thr Gly Lys
            165                 170                 175

Cys Ser Phe Leu Pro Glu Glu Arg Glu Trp Met Asp Arg Leu Met Ser
            180                 185                 190

Trp Gly Leu Val Asp Thr Phe Arg His Ala Asn Pro Gln Thr Ala Asp
            195                 200                 205

Arg Phe Ser Trp Phe Asp Tyr Arg Ser Lys Gly Phe Asp Asp Asn Arg
        210                 215                 220

Gly Leu Arg Ile Asp Leu Leu Ala Ser Gln Pro Leu Ala Glu Cys
225                 230                 235                 240

Cys Val Glu Thr Gly Ile Asp Tyr Glu Ile Arg Ser Met Glu Lys Pro
            245                 250                 255

Ser Asp His Ala Pro Val Trp Ala Thr Phe Arg Arg
            260                 265

<210> SEQ ID NO 30
<211> LENGTH: 1246
<212> TYPE: DNA
<213> ORGANISM: Escherichia coli

<400> SEQUENCE: 30

```
gatcattgac gaaatttact ggaaattact gcgccattct gacgcagcgc gcaccaaaag      60
cgggcatttt ttgcgccatc gttgacatca ttaacaacca tcgatcaaat cacttaacaa     120
caggcggtaa gcaacgcgaa attctgctac catccacgca ctctttatct gaataaatgg     180
cagcgactat gaaatttgtc tcttttaata tcaacggcct gcgcgccaga cctcaccagc     240
ttgaagccat cgtcgaaaag caccaaccgg atgtgattgg cctgcaggag acaaaagttc     300
atgacgatat gtttccgctc gaagagtgg cgaagctcgg ctacaacgtg ttttatcacg      360
ggcagaaagg ccattatggc gtggcgctgc tgaccaaaga gacgccgatt gccgtgcgtc     420
gcggctttcc cggtgacgac gaagaggcgc agcggcggat tattatggcg gaaatcccct     480
cactgctggg taatgtcacc gtgatcaacg gttacttccc gcagggtgaa agccgcgacc     540
atccgataaa attcccggca aaagcgcagt ttatcagaa tctgcaaaac tacctggaaa      600
ccgaactcaa acgtgataat ccggtactga ttatgggcga tatgaatatc agccctacag     660
atctggatat cggcattggc gaagaaaacc gtaagcgctg gctgcgtacc ggtaaatgct     720
ctttcctgcc ggaagagcgc gaatggatgg acaggctgat gagctggggg ttggtcgata     780
ccttccgcca tgcgaatccg caaacagcag atcgtttctc atggtttgat taccgctcaa     840
aaggttttga cgataaccgt ggtctgcgca tcgacctgct gctcgccagc caaccgctgg     900
cagaatgttg cgtagaaacc ggcatcgact atgaaatccg cagcatggaa aaaccgtccg     960
atcacgcccc cgtctgggcg accttccgcc gctaatttag cagctctcct ggctcaaact    1020
gggtcaggag aattaaccttt gagaaaaatc aacaaactgt cagtaatgat tgttgcctg    1080
ccgtcctttg ttataccgtc tctgcgtttt tagttgtctg accacttctc tattatcaag    1140
tttgatatag gaaactccac gatgaacgct gagcgtaaat ttcttttttgc ctgtcttatt    1200
tttgcgctgg tcatttacgc tatccacgct ttcggttttat tcgatc                  1246
```

<210> SEQ ID NO 31
<211> LENGTH: 285
<212> TYPE: PRT
<213> ORGANISM: Escherichia coli

<400> SEQUENCE: 31

```
Met Lys Tyr Ile Gly Ala His Val Ser Arg Ala Gly Leu Ala Asn
  1               5                  10                  15

Ala Ala Ile Arg Ala Ala Glu Ile Asp Ala Thr Ala Phe Ala Leu Phe
             20                  25                  30

Thr Lys Asn Gln Arg Gln Trp Arg Ala Ala Pro Leu Thr Thr Gln Thr
         35                  40                  45

Ile Asp Glu Phe Lys Ala Ala Cys Glu Lys Tyr His Tyr Thr Ser Ala
     50                  55                  60

Gln Ile Leu Pro His Asp Ser Tyr Leu Ile Asn Leu Gly His Pro Val
 65                  70                  75                  80

Thr Glu Ala Leu Glu Lys Ser Arg Asp Ala Phe Ile Asp Glu Met Gln
                 85                  90                  95

Arg Cys Glu Gln Leu Gly Leu Ser Leu Leu Asn Phe His Pro Gly Ser
             100                 105                 110

His Leu Met Gln Ile Ser Glu Asp Cys Leu Ala Arg Ile Ala Glu
             115                 120                 125

Ser Ile Asn Ile Ala Leu Asp Lys Thr Gln Gly Val Thr Ala Val Ile
         130                 135                 140

Glu Asn Thr Ala Gly Gln Gly Ser Asn Leu Gly Phe Lys Phe Glu His
145                 150                 155                 160

Leu Ala Ala Ile Ile Asp Gly Val Glu Asp Lys Ser Arg Val Gly Val
                 165                 170                 175

Cys Ile Asp Thr Cys His Ala Phe Ala Ala Gly Tyr Asp Leu Arg Thr
             180                 185                 190

Pro Ala Glu Cys Glu Lys Thr Phe Ala Asp Phe Ala Arg Thr Val Gly
         195                 200                 205

Phe Lys Tyr Leu Arg Gly Met His Leu Asn Asp Ala Lys Ser Thr Phe
210                 215                 220

Gly Ser Arg Val Asp Arg His His Ser Leu Gly Glu Gly Asn Ile Gly
225                 230                 235                 240

His Asp Ala Phe Arg Trp Ile Met Gln Asp Asp Arg Phe Asp Gly Ile
             245                 250                 255

Pro Leu Ile Leu Glu Thr Ile Asn Pro Asp Ile Trp Ala Glu Glu Ile
             260                 265                 270

Ala Trp Leu Lys Ala Gln Gln Thr Glu Lys Ala Val Ala
             275                 280                 285

<210> SEQ ID NO 32
<211> LENGTH: 1020
<212> TYPE: DNA
<213> ORGANISM: Escherichia coli

<400> SEQUENCE: 32
catcgcataa accactacat cttgctctgt taaccgctat cattaccgtt ttcctccagc      60
gggtttaaca ggagtcctcg catgaaatac attggagcgc acgttagtcg tgctggcggt     120
ctggcaaatg ccgcaattcg cgccgccgaa atcgacgcaa ccgcgtttgc cttgttcacc     180
aaaaaccaac gtcagtggcg tgccgcaccg ctcacgacgc aaaccatcga tgaattcaaa     240
gccgcctgtg aaaaatatca ctacacatcg gcgcaaattc ttccccacga cagttatctg     300
attaacctcg gacatccggt cactgaagct ctggaaaaat cgcgcgatgc ctttatagat     360
gaaatgcagc gttgcgaaca gctggggctt tctttgctca acttccaccc tggcagccat     420
ctgatgcaga tttcagaaga ggattgcctt gcgcgtattg ccgaatccat caacattgcg     480
```

```
ctggataaaa ctcaaggtgt gacagcggtg atagaaaaca ccgccggtca gggcagtaac      540
ttagggttta aattcgaaca tctcgcggcg attatcgacg gcgtggaaga taaatcccgc      600
gtcggcgtct gcattgatac ctgccatgct ttcgctgccg ggtatgattt gcgtactcca      660
gccgaatgcg agaaaacatt cgcggatttt gcccgtactg tcggctttaa gtatctgcgc      720
gggatgcacc ttaacgatgc gaaaagcacc tttggcagcc gcgttgaccg ccatcatagc      780
ctcggtgaag gcaatatcgg tcatgatgcg ttccgctgga tcatgcagga cgaccgtttc      840
gacggcattc cgctgatcct cgaaaccatc aacccggata tctgggcaga agagatcgcc      900
tggctgaaag cgcaacaaac tgaaaagcg gtagcctgaa gatgaataac cgggaaaagg       960
agatccttgc aattttacgg cgtaacccgc tgattcagca gaacgaaatt gcggacatgc     1020
```

<210> SEQ ID NO 33
<211> LENGTH: 138
<212> TYPE: PRT
<213> ORGANISM: Artificial Sequence
<220> FEATURE:
<223> OTHER INFORMATION: Description of Artificial Sequence:Synthetic
      gene

<400> SEQUENCE: 33

```
Met Thr Arg Ile Asn Leu Thr Leu Val Ser Glu Leu Ala Asp Gln His
  1               5                  10                  15

Leu Met Ala Glu Tyr Arg Glu Leu Pro Arg Val Phe Gly Ala Val Arg
                 20                  25                  30

Lys His Val Ala Asn Gly Lys Arg Val Arg Asp Phe Lys Ile Ser Pro
             35                  40                  45

Thr Phe Ile Leu Gly Ala Gly His Val Thr Phe Phe Tyr Asp Lys Leu
         50                  55                  60

Glu Phe Leu Arg Lys Arg Gln Ile Glu Leu Ile Ala Glu Cys Leu Lys
     65                  70                  75                  80

Arg Gly Phe Asn Ile Lys Asp Thr Thr Val Gln Asp Ile Ser Asp Ile
                     85                  90                  95

Pro Gln Glu Phe Arg Gly Asp Tyr Ile Pro His Glu Ala Ser Ile Ala
                100                 105                 110

Ile Ser Gln Ala Arg Leu Asp Glu Lys Ile Ala Gln Arg Pro Thr Trp
            115                 120                 125

Tyr Lys Tyr Tyr Gly Lys Ala Ile Tyr Ala
        130                 135
```

<210> SEQ ID NO 34
<211> LENGTH: 424
<212> TYPE: DNA
<213> ORGANISM: Artificial Sequence
<220> FEATURE:
<223> OTHER INFORMATION: Description of Artificial Sequence:Synthetic
      gene
<400> SEQUENCE: 34

```
cgatatgacg cgtatcaacc ttactttagt atccgagtta gctgaccaac acttaatggc       60
tgaataccgt gaattgccgc gtgttttgg tgcagttcgt aagcacgtag caaacggtaa      120
acgtgttcgt gacttcaaaa tcagtcctac ttttatcctt ggcgcaggtc atgttacatt      180
cttctacgat aagctcgagt tcttacgcaa gcgtcaaatt gagcttatag ctgaatgttt      240
gaaacgtggc ttcaatatca aggatactac agtccaggac atcagtgaca ttcctcaaga      300
attccgtggt gattatattc cccatgaagc ttcattgct atatcacaag ctcgtttaga       360
tgaaaaaatt gcacaacgtc ctacttggta caaatactac ggtaaggcga tttatgcatg      420
```

```
atag                                                                    424
```

<210> SEQ ID NO 35
<211> LENGTH: 229
<212> TYPE: PRT
<213> ORGANISM: Escherichia coli

<400> SEQUENCE: 35

```
Met Ala Asn Glu Leu Thr Trp His Asp Val Leu Ala Glu Glu Lys Gln
  1               5                  10                  15

Gln Pro Tyr Phe Leu Asn Thr Leu Gln Thr Val Ala Ser Glu Arg Gln
                 20                  25                  30

Ser Gly Val Thr Ile Tyr Pro Pro Gln Lys Asp Val Phe Asn Ala Phe
             35                  40                  45

Arg Phe Thr Glu Leu Gly Asp Val Lys Val Val Ile Leu Gly Gln Asp
         50                  55                  60

Pro Tyr His Gly Pro Gly Gln Ala His Gly Leu Ala Phe Ser Val Arg
 65                  70                  75                  80

Pro Gly Ile Ala Ile Pro Pro Ser Leu Leu Asn Met Tyr Lys Glu Leu
                 85                  90                  95

Glu Asn Thr Ile Pro Gly Phe Thr Arg Pro Asn His Gly Tyr Leu Glu
                100                 105                 110

Ser Trp Ala Arg Gln Gly Val Leu Leu Leu Asn Thr Val Leu Thr Val
            115                 120                 125

Arg Ala Gly Gln Ala His Ser His Ala Ser Leu Gly Trp Glu Thr Phe
        130                 135                 140

Thr Asp Lys Val Ile Ser Leu Ile Asn Gln His Arg Glu Gly Val Val
145                 150                 155                 160

Phe Leu Leu Trp Gly Ser His Ala Gln Lys Lys Gly Ala Ile Ile Asp
                165                 170                 175

Lys Gln Arg His His Val Leu Lys Ala Pro His Pro Ser Pro Leu Ser
            180                 185                 190

Ala His Arg Gly Phe Phe Gly Cys Asn His Phe Val Leu Ala Asn Gln
        195                 200                 205

Trp Leu Glu Gln Arg Gly Glu Thr Pro Ile Asp Trp Met Pro Val Leu
210                 215                 220

Pro Ala Glu Ser Glu
225
```

<210> SEQ ID NO 36
<211> LENGTH: 1532
<212> TYPE: DNA
<213> ORGANISM: Escherichia coli

<400> SEQUENCE: 36

```
gttaacgttc aggtgttgac caccttcaac gcgaacttct ggtttcactt ctactggaac    60
ttcacggtat tcaatgtcac ccagtttgct tactgcaacc acttcatctt ctgcataacc   120
tgcttttgca acgatgcaac gcgcttcgcc ttttcgctg tccagcagcc agaaagagtt    180
cagcagatcg tcgttagcgg ctttagtaat ctggatacct gtaatcatgt gatgcctccc   240
cggcaaaatt atttgatttg ttcagcctgt cgcggccaat tggtaaaacc attgttgctt   300
gagtgtatat atactcctca aacacccttg aatctttgat ttaaatcaat aaaaaccaca   360
catcaagtat ggtcgcaaat ggattttatt gttttacatc aacttatgcg ggtgtgaaat   420 ttaccaatt tacattttttt tgcactcgtt taagtctaaa aaatgagcat gatttttgttc  480
```

-continued

```
tgtagaaaga agcagttaag ctaggcggat tgaagattcg caggagagcg agatggctaa      540
cgaattaacc tggcatgacg tgctggctga agagaagcag caaccctatt ttcttaatac      600
ccttcagacc gtcgccagcg agcggcagtc cggcgtcact atctacccac acaaaaaga       660 tgtctttaac gcgttccgct ttacagagtt gggtgacgtt aaagtggtga ttctcggcca      720
ggatccttat cacggaccgg gacaggcgca tggtctggca ttttccgttc gtcccggcat      780
tgccattcct ccgtcattat tgaatatgta taaagagctg gaaaatacta ttccgggctt      840
cacccgccct aatcatggtt atcttgaaag ctgggcgcgt cagggcgttc tgctactcaa      900
tactgtgttg acggtacgcg caggtcaggc gcattcccac gccagcctcg gctgggaaac      960
cttcaccgat aaagtgatca gcctgattaa ccagcatcgc gaaggcgtgg tgttttttgtt    1020 gtggggatcg catgcgcaaa agaaagggc gattatagat aagcaacgcc atcatgtact     1080
gaaagcaccg catccgtcgc cgctttcggc gcatcgtgga ttctttggct gcaaccattt     1140
tgtgctggca aatcagtggc tggaacaacg tggcgagacg ccgattgact ggatgccagt     1200
attaccggca gagagtgagt aaatttgcgg ggaaatgccg gatggcagag ttgccacccg     1260
gctgatttat caggctttat tctgacgcca ccattcacca agcaaaacgc cggttgcgac     1320
agagatattc agcccggcaa cgttgcccgt accgtcaatc ttcacgcgca gatcgttcgg     1380
atcgcgtgcg gcatccggta acccttcata ttcctgaccc agcaccagta ccattttcgc     1440
tggcagacta gttttgaaca gcggtttacc ctgctcgctg aagtggtca ctacggtgta     1500 acctgctgac ggaaatcatc cagcacgtta ac                                   1532
```

<210> SEQ ID NO 37
<211> LENGTH: 350
<212> TYPE: PRT
<213> ORGANISM: Escherichia coli

<400> SEQUENCE: 37

```
Met Gln Ala Ser Gln Phe Ser Ala Gln Val Leu Asp Trp Tyr Asp Lys
  1               5                  10                  15

Tyr Gly Arg Lys Thr Leu Pro Trp Gln Ile Asp Lys Thr Pro Tyr Lys
                 20                  25                  30

Val Trp Leu Ser Glu Val Met Leu Gln Gln Thr Gln Val Ala Thr Val
             35                  40                  45

Ile Pro Tyr Phe Glu Arg Phe Met Ala Arg Phe Pro Thr Val Thr Asp
         50                  55                  60

Leu Ala Asn Ala Pro Leu Asp Glu Val Leu His Leu Trp Thr Gly Leu
 65                  70                  75                  80

Gly Tyr Tyr Ala Arg Ala Arg Asn Leu His Lys Ala Ala Gln Gln Val
                 85                  90                  95

Ala Thr Leu His Gly Gly Lys Phe Pro Glu Thr Phe Glu Glu Val Ala
            100                 105                 110

Ala Leu Pro Gly Val Gly Arg Ser Thr Ala Gly Ala Ile Leu Ser Leu
        115                 120                 125

Ser Leu Gly Lys His Phe Pro Ile Leu Asp Gly Asn Val Lys Arg Val
    130                 135                 140

Leu Ala Arg Cys Tyr Ala Val Ser Gly Trp Pro Gly Lys Lys Glu Val
145                 150                 155                 160

Glu Asn Lys Leu Trp Ser Leu Ser Glu Gln Val Thr Pro Ala Val Gly
                165                 170                 175

Val Glu Arg Phe Asn Gln Ala Met Met Asp Leu Gly Ala Met Ile Cys
```

```
                180                  185                  190
Thr Arg Ser Lys Pro Lys Cys Ser Leu Cys Pro Leu Gln Asn Gly Cys
            195                  200                  205

Ile Ala Ala Ala Asn Asn Ser Trp Ala Leu Tyr Pro Gly Lys Lys Pro
    210                  215                  220

Lys Gln Thr Leu Pro Glu Arg Thr Gly Tyr Phe Leu Leu Leu Gln His
225                  230                  235                  240

Glu Asp Glu Val Leu Leu Ala Gln Arg Pro Pro Ser Gly Leu Trp Gly
                245                  250                  255

Gly Leu Tyr Cys Phe Pro Gln Phe Ala Asp Glu Ser Leu Arg Gln
            260                  265                  270

Trp Leu Ala Gln Arg Gln Ile Ala Ala Asp Asn Leu Thr Gln Leu Thr
        275                  280                  285

Ala Phe Arg His Thr Phe Ser His Phe His Leu Asp Ile Val Pro Met
        290                  295                  300

Trp Leu Pro Val Ser Ser Phe Thr Gly Cys Met Asp Glu Gly Asn Ala
305                  310                  315                  320

Leu Trp Tyr Asn Leu Ala Gln Pro Pro Ser Val Gly Leu Ala Ala Pro
                325                  330                  335

Val Glu Arg Leu Leu Gln Gln Leu Arg Thr Gly Ala Pro Val
            340                  345                  350
```

<210> SEQ ID NO 38
<211> LENGTH: 2293
<212> TYPE: DNA
<213> ORGANISM: Escherichia coli

<400> SEQUENCE: 38

```
agcttgcatg cagatcagac cttcccaggc cagataaccg ctgccgtcaa aggccagttt      60
gttcggttcg ataacctcgt taataaaatc atcaacggtt ttatcaatct gttcttccga     120
tgtaccttcc gggaatcgcc atgccaccga aaatcctaat tcctggaatt cgtcgatgtg     180
cattttttta cgcagacgac ggctacggtt ctttgccatt atttcaccct ctcgaacatt     240
aagtcccata ctccgtgacc aagacgatga ccacgttgtt caaatttcgt caccggacgt     300
gatgccggac gcggtacgta atcattgctc tctgacaggt ttttataacc gtcaatagaa     360
gacatcactt caagcatatg ttccgcataa ggttcccagt cggtcgccat atggaatacg     420
cccccagct gcagtttgct ttttaccagt tcggcaaacg gcacctgaac gatacggcgt     480
ttattatggc gcgctttgtg ccacgggtca gggaaaaaga gctgcaccat gcgcaatgaa     540
ttgtcaggaa tcattttatg cagcacttca accgcatcgt gacacatcac gcgcaggttg     600
cttaaacctt cttcatgcgc agaagccagg cacgcaccaa cgcccggtga atgcacttca     660
atgccgagga gtcctgctc agggcgatct ttagccattg ccaccagcga cgcccccatg     720
ccaaaaccaa tctcaagcgt caccggcgct tcacggccaa aaagcgcggg gaaatccagc     780
atatcttcgc tgaactcaac gcccatcacc ggccagtagt tttccagcgc atgttcctgg     840
cctttggtca gtcggcccct ggcggcgcac aaaactacgg atacggcgca gtgggcggcc     900
gttttcatca aattccggtg aaatgacgtc gtttttcata aaggtttagt cgcttgtgaa     960
agtgttctga aaacgggcat tatccaaagt tagttgccgg atgcaagcat gataaggccg    1020
tgctgcgga aagttccggt ttacaccctg ccgtcgctgt gctgcaatct gcccccaac    1080
aacagtgaat tcggtgacca tgcaagcgtc gcaattttca gccaggttc tggactggta    1140
cgataaatac gggcgaaaaa ctctgccctg gcaaattgac aagacgccct acaaagtatg    1200
```

```
gctctcagaa gtgatgttgc aacaaactca ggttgcgacc gttatcccct attttgaacg    1260
ctttatggcg cgcttcccga cggtgaccga tctcgccaat gcgccgctcg acgaagttct    1320
ccacttgtgg accgggcttg gctattacgc ccgcgcgcg aatctgcata aagcggcaca    1380
acaagtggcg accttacacg gcggtaaatt cccggaaacc tttgaggaag ttgcagcact    1440 gccggcgtc gggcgttcca ccgcaggcgc gattctctcg ctttctctgg gtaagcactt    1500
tccgattctc gacggtaacg tcaaacgcgt gctggcgcgc tgctatgctg taagcggctg    1560
gcctgggaaa aagaggtcg agaataaatt atggagtttg agcgagcagg tgacgcccgc    1620
ggttggcgtg aacggtttta atcaggcgat gatggatttg ggtgcgatga tttgtacgcg    1680
ctcgaaaccg aaatgttcgc tctgtccgct acaaaacgga tgtattgccg ccgccaacaa    1740
tagctgggcg ctttatccgg gcaaaaaacc gaaacagacg ctgccggagc gcaccggcta    1800 cttttttgcta ttacagcacg aagatgaagt attgctggcg cagcgtccgc cgagcggatt    1860
gtggggcggt ttatactgtt tcccgcagtt tgccgacgaa gaaagtttgc ggcagtggct    1920
ggcgcaacgg cagattgctg ccgataacct gacgcaactg accgcgtttc ggcataccctt    1980 cagccatttc cacttagata ttgtgcctat gtggcttccc gtgtcgtcat tcaccggctg    2040
catggatgaa ggcaatgcgc tctggtataa cttagcgcaa ccgccgtcag ttggcctagc    2100
ggctcccgtg gagcgtttgt tacagcagtt acgcactggc gcgccggttt agcgcgtgag    2160
tcgataaaga ggatgattta tgagcagaac gatttttttgt actttcctgc aacgtgaagc    2220
agaaggtcag gattttcagc tgtaccccgg cgagctggga aaacgcatct ataacgagat    2280
cctctacgcg acg                                                       2293
```

<210> SEQ ID NO 39
<211> LENGTH: 138
<212> TYPE: PRT
<213> ORGANISM: Artificial Sequence
<220> FEATURE:
<223> OTHER INFORMATION: Description of Artificial Sequence:Synthetic
      gene

<400> SEQUENCE: 39

```
Met Thr Arg Ile Asn Leu Thr Leu Val Ser Glu Leu Ala Asp Gln His
  1               5                  10                  15

Leu Met Ala Glu Tyr Arg Glu Leu Pro Arg Val Phe Gly Ala Val Arg
             20                  25                  30

Lys His Val Ala Asn Gly Lys Arg Val Arg Asp Phe Lys Ile Ser Pro
         35                  40                  45

Thr Phe Ile Leu Gly Ala Gly His Val Thr Phe Tyr Asp Lys Leu
     50                  55                  60

Glu Phe Leu Arg Lys Arg Gln Ile Glu Leu Ile Ala Glu Cys Leu Lys
 65                  70                  75                  80

Arg Gly Phe Asn Ile Lys Asp Thr Thr Val Gln Asp Ile Ser Asp Ile
                 85                  90                  95

Pro Gln Glu Phe Arg Gly Asp Tyr Ile Pro His Glu Ala Ser Ile Ala
            100                 105                 110

Ile Ser Gln Ala Arg Leu Asp Glu Lys Ile Ala Gln Arg Pro Thr Trp
        115                 120                 125

Tyr Lys Tyr Tyr Gly Lys Ala Ile Tyr Ala
    130                 135
```

<210> SEQ ID NO 40

-continued

```
<211> LENGTH: 424
<212> TYPE: DNA
<213> ORGANISM: Artificial Sequence
<220> FEATURE:
<223> OTHER INFORMATION: Description of Artificial Sequence:Synthetic
      gene

<400> SEQUENCE: 40
cgatatgacg cgtatcaacc ttactttagt atccgagtta gctgaccaac acttaatggc      60
tgaataccgt gaattgccgc gtgttttggg tgcagttcgt aagcacgtag caaacggtaa     120
acgtgttcgt gacttcaaaa tcagtcctac ttttatcctt ggcgcaggtc atgttacatt     180
cttctacgat aagctcgagt tcttacgcaa gcgtcaaatt gagcttatag ctgaatgttt     240
gaaacgtggc ttcaatatca aggatactac agtccaggac atcagtgaca ttcctcaaga     300
attccgtggt gattatattc cccatgaagc ttctattgct atatcacaag ctcgtttaga     360
tgaaaaaatt gcacaacgtc ctacttggta caaatactac ggtaaggcga tttatgcatg     420
atag                                                                  424

<210> SEQ ID NO 41
<211> LENGTH: 410
<212> TYPE: PRT
<213> ORGANISM: Homo sapiens

<400> SEQUENCE: 41
```

Met Glu Ala Glu Asn Ala Gly Ser Tyr Ser Leu Gln Gln Ala Gln Ala
 1               5                  10                  15

Phe Tyr Thr Phe Pro Phe Gln Gln Leu Met Ala Glu Ala Pro Asn Met
                20                  25                  30

Ala Val Val Asn Glu Gln Gln Met Pro Glu Glu Val Pro Ala Pro Ala
            35                  40                  45

Pro Ala Gln Glu Pro Val Gln Glu Ala Pro Lys Gly Arg Lys Arg Lys
        50                  55                  60

Pro Arg Thr Thr Glu Pro Lys Gln Pro Val Glu Pro Lys Lys Pro Val
65                  70                  75                  80

Glu Ser Lys Lys Ser Gly Lys Ser Ala Lys Pro Lys Glu Lys Gln Glu
                85                  90                  95

Lys Ile Thr Asp Thr Phe Lys Val Lys Arg Lys Val Asp Arg Phe Asn
            100                 105                 110

Gly Val Ser Glu Ala Glu Leu Leu Thr Lys Thr Leu Pro Asp Ile Leu
        115                 120                 125

Thr Phe Asn Leu Asp Ile Val Ile Gly Ile Asn Pro Gly Leu Met
    130                 135                 140

Ala Ala Tyr Lys Gly His His Tyr Pro Gly Pro Gly Asn His Phe Trp
145                 150                 155                 160

Lys Cys Leu Phe Met Ser Gly Leu Ser Glu Val Gln Leu Asn His Met
                165                 170                 175

Asp Asp His Thr Leu Pro Gly Leu Tyr Gly Ile Gly Phe Thr Asn Met
            180                 185                 190

Val Glu Arg Thr Thr Pro Gly Ser Lys Asp Leu Ser Ser Lys Glu Phe
        195                 200                 205

Arg Glu Gly Gly Arg Ile Leu Val Gln Lys Leu Gln Lys Tyr Gln Pro
    210                 215                 220

Arg Ile Ala Val Phe Asn Gly Lys Cys Ile Tyr Glu Ile Phe Ser Lys
225                 230                 235                 240

Glu Val Phe Gly Val Lys Val Lys Asn Leu Glu Phe Gly Leu Gln Pro

```
                  245                 250                 255
His Lys Ile Pro Asp Thr Glu Thr Leu Cys Tyr Val Met Pro Ser Ser
            260                 265                 270
Ser Ala Arg Cys Ala Gln Phe Pro Arg Ala Gln Asp Lys Val His Tyr
        275                 280                 285
Tyr Ile Lys Leu Lys Asp Leu Arg Asp Gln Leu Lys Gly Ile Glu Arg
    290                 295                 300
Asn Met Asp Val Gln Glu Val Gln Tyr Thr Phe Asp Leu Gln Leu Ala
305                 310                 315                 320
Gln Glu Asp Ala Lys Lys Met Ala Val Lys Glu Lys Tyr Asp Pro
                325                 330                 335
Gly Tyr Glu Ala Ala Tyr Gly Gly Ala Tyr Gly Glu Asn Pro Cys Ser
            340                 345                 350
Ser Glu Pro Cys Gly Phe Ser Ser Asn Gly Leu Ile Glu Ser Val Glu
        355                 360                 365
Leu Arg Gly Glu Ser Ala Phe Ser Gly Ile Pro Asn Gly Gln Trp Met
    370                 375                 380
Thr Gln Ser Phe Thr Asp Gln Ile Pro Ser Phe Ser Asn His Cys Gly
385                 390                 395                 400
Thr Gln Glu Gln Glu Glu Glu Ser His Ala
                405                 410
```

<210> SEQ ID NO 42
<211> LENGTH: 3410
<212> TYPE: DNA
<213> ORGANISM: Homo sapiens

<400> SEQUENCE: 42

```
gcaccaggcg cccagtggag ccgtttggga gaattgcctg cgccacgcag cggggccgga      60
caggcggtaa ggatctgatt aggctttcga acttgagttt gactgatgtc ttctgtgtgg     120
tgtccgctaa atcccacagc ataggatc agtcgcattg gttataaggt ttgcttctgg      180
ctgggtgcgg tggctcatgc ctgtaatcca acattgggag gccaaggcag gcggaccacc     240
tgaagtcggg agcttgagtc cagccactgt ctgggtactg ccagccatcg ggcccaggtc     300
tctggggttg tcttaccgca gtgagtacca cgcggtacta cagagaccgg ctgcccgtgt     360
gcccggcagg tggagccgcc gcatcagcgg cctcgggaa tggaagcgga gaacgcgggc      420
agctattccc ttcagcaagc tcaagctttt tatacgtttc catttcaaca actgatggct     480
gaagctccta atatggcagt tgtgaatgaa cagcaaatgc agaagaagt tccagcccca      540
gctcctgctc aggaaccagt gcaagaggct ccaaaaggaa gaaaagaaa acccagaaca      600
acagaaccaa acaaccagt ggaacccaaa aaacctgttg agtcaaaaaa atctggcaag      660
tctgcaaaac caaagaaaa acaagaaaaa attacagaca catttaaagt aaaaagaaaa      720
gtagaccgtt ttaatggtgt tcagaagct gaacttctga ccaagactct ccccgatatt      780
ttgaccttca atctggacat tgtcattatt ggcataaacc cgggactaat ggctgcttac      840
aaagggcatc attaccctgg acctggaaac cattttttgga agtgtttgtt tatgtcaggg     900
ctcagtgagg tccagctgaa ccatatggat gatcacactc taccagggaa gtatggtatt     960
ggatttacca acatggtgga aaggaccacg cccggcagca agatctctc cagtaaagaa     1020
tttcgtgaag aggacgtat tctagtacag aaattacaga aatatcagcc acgaatagca     1080
gtgtttaatg gaaaatgtat ttatgaaatt tttagtaaag aagttttgg agtaaaggtt     1140
aagaacttgg aatttgggct tcagccccat aagattccag acacagaaac tctctgctat     1200
```

```
gttatgccat catccagtgc aagatgtgct cagtttcctc gagcccaaga caaagttcat    1260
tactacataa aactgaagga cttaagagat cagttgaaag gcattgaacg aaatatggac    1320
gttcaagagg tgcaatatac atttgaccta cagcttgccc aagaggatgc aaagaagatg    1380
gctgttaagg aagaaaaata tgatccaggt tatgaggcag catatggtgg tgcttacgga    1440
gaaaatccat gcagcagtga accttgtggc ttctcttcaa atgggctaat tgagagcgtg    1500
gagttaagag gagaatcagc tttcagtggc attcctaatg ggcagtggat gacccagtca    1560
tttacagacc aaattccttc ctttagtaat cactgtggaa cacaagaaca ggaagaagaa    1620
agccatgctt aagaatggtg cttctcagct ctgcttaaat gctgcagttt taatgcagtt    1680
gtcaacaagt agaacctcag tttgctaact gaagtgtttt attagtattt tactctagtg    1740
gtgtaattgt aatgtagaac agttgtgtgg tagtgtgaac cgtatgaacc taagtagttt    1800
ggaagaaaaa gtagggtttt tgtatactag cttttgtatt tgaattaatt atcattccag    1860 cttttttatat actatatttc atttatgaag aaattgattt tcttttggga gtcactttta    1920
atctgtaatt ttaaaataca agtctgaata tttatagttg attcttaact gtgcataaac    1980
ctagatatac cattatccct tttataccta agaagggcat gctaataatt accactgtca    2040
aagaggcaaa ggtgttgatt tttgtatata agttaagcct cagtggagtc tcatttgtta    2100
gtttttagtg gtaactaagg gtaaactcag ggttccctga gctatatgca cactcagacc    2160
tctttgcttt accagtggtg tttgtgagtt gctcagtagt aaaaactggc ccttacctga    2220
cagagccctg gctttgacct gctcagccct gtgtgttaat cctctagtag ccaattaact    2280
actctggggt ggcaggttcc agagaatcga gtagaccttt tgccactcat ctgtgtttta    2340
cttgagacat gtaaatatga tagggaagga actgaatttc tccattcata tttataacca    2400
ttctagtttt atcttccttg gctttaagag tgtgccatgg aaagtgataa gaatgaact     2460 tctaggctaa gcaaaaagat gctggagata tttgatactc tcatttaaac tggtgcttta    2520
tgtacatgag atgtactaaa ataagtaata tagaattttt cttgctaggt aaatccagta    2580
agccaataat tttaaagatt cttatctgc atcattgctg tttgttacta taaattaaat     2640
gaacctcatg gaaaggttga ggtgtatacc tttgtgattt tctaatgagt tttccatggt    2700
gctacaaata atccagacta ccaggtctgg tagatattaa agctgggtac taagaaatgt    2760
tatttgcatc ctctcagtta ctcctgaata ttctgatttc atacgtaccc agggagcatg    2820
ctgttttgtc aatcaatata aaatatttat gaggtctccc ccacccccag gaggttatat    2880
gattgctctt ctctttataa taagagaaac aaattcttat tgtgaatctt aacatgcttt    2940
ttagctgtgg ctatgatgga ttttattttt tcctaggtca agctgtgtaa aagtcattta    3000
tgttatttaa atgatgtact gtactgctgt ttacatggac gttttgtgcg ggtgctttga    3060
agtgccttgc atcagggatt aggagcaatt aaattatttt ttcacgggac tgtgtaaagc    3120
atgtaactag gtattgcttt ggtatataac tattgtagct ttacaagaga ttgttttatt    3180
tgaatgggga aaatacccctt taaattatga cggacatcca ctagagatgg gtttgaggat    3240
tttccaagcg tgtaataatg atgttttttcc taacatgaca gatgagtagt aaatgttgat    3300
atatcctata catgacagtg tgagacttttt tcattaaata atattgaaag atttttaaaat  3360 tcatttgaaa gtctgatggc ttttacaata aaagatatta agaattgtta             3410
```

<210> SEQ ID NO 43
<211> LENGTH: 24
<212> TYPE: DNA

```
<213> ORGANISM: Artificial Sequence
<220> FEATURE:
<223> OTHER INFORMATION: Description of Artificial Sequence:PCR Primer

<400> SEQUENCE: 43
ctccatatgg cgccgctgct ggag                                              24

<210> SEQ ID NO 44
<211> LENGTH: 42
<212> TYPE: DNA
<213> ORGANISM: Artificial Sequence
<220> FEATURE:
<223> OTHER INFORMATION: Description of Artificial Sequence:PCR Primer

<400> SEQUENCE: 44
actaccagga ctaggaccac taccgttgct ttctaggacc ag                          42

<210> SEQ ID NO 45
<211> LENGTH: 42
<212> TYPE: DNA
<213> ORGANISM: Artificial Sequence
<220> FEATURE:
<223> OTHER INFORMATION: Description of Artificial Sequence:PCR Primer

<400> SEQUENCE: 45
ggtagtggtc ctagtcctgg tagtatggcg ccgctgctgg ag                          42

<210> SEQ ID NO 46
<211> LENGTH: 30
<212> TYPE: DNA
<213> ORGANISM: Artificial Sequence
<220> FEATURE:
<223> OTHER INFORMATION: Description of Artificial Sequence:PCR Primer

<400> SEQUENCE: 46
ctcgagctct cagttgcttt ctaggaccag                                        30

<210> SEQ ID NO 47
<211> LENGTH: 31
<212> TYPE: DNA
<213> ORGANISM: Artificial Sequence
<220> FEATURE:
<223> OTHER INFORMATION: Description of Artificial Sequence:PCR Primer

<400> SEQUENCE: 47
ctccatatgg aatttgatta tgtaatatgc g                                      31

<210> SEQ ID NO 48
<211> LENGTH: 52
<212> TYPE: DNA
<213> ORGANISM: Artificial Sequence
<220> FEATURE:
<223> OTHER INFORMATION: Description of Artificial Sequence:PCR Primer

<400> SEQUENCE: 48
actaccagga ctaggaccac taccaaattt cttctgtttc atttttctc gg                52

<210> SEQ ID NO 49
<211> LENGTH: 49
<212> TYPE: DNA
<213> ORGANISM: Artificial Sequence
<220> FEATURE:
<223> OTHER INFORMATION: Description of Artificial Sequence:PCR Primer

<400> SEQUENCE: 49
ggtagtggtc ctagtcctgg tagtatggaa tttgattatg taatatgcg                   49
```

```
<210> SEQ ID NO 50
<211> LENGTH: 40
<212> TYPE: DNA
<213> ORGANISM: Artificial Sequence
<220> FEATURE:
<223> OTHER INFORMATION: Description of Artificial Sequence:PCR Primer

<400> SEQUENCE: 50
ctcgagctct caaaatttct tctgtttcat ttttctcgg                              40

<210> SEQ ID NO 51
<211> LENGTH: 28
<212> TYPE: DNA
<213> ORGANISM: Artificial Sequence
<220> FEATURE:
<223> OTHER INFORMATION: Description of Artificial Sequence:PCR Primer

<400> SEQUENCE: 51
ctccatatgt ccaggcatgc ttgtgttg                                          28

<210> SEQ ID NO 52
<211> LENGTH: 43
<212> TYPE: DNA
<213> ORGANISM: Artificial Sequence
<220> FEATURE:
<223> OTHER INFORMATION: Description of Artificial Sequence:PCR Primer

<400> SEQUENCE: 52
actaccagga ctaggaccac tacctctttc cagatagcac ttc                         43

<210> SEQ ID NO 53
<211> LENGTH: 43
<212> TYPE: DNA
<213> ORGANISM: Artificial Sequence
<220> FEATURE:
<223> OTHER INFORMATION: Description of Artificial Sequence:PCR Primer

<400> SEQUENCE: 53
ggtagtggtc ctagtcctgg tagttccagg catgcttgtg ttg                         43

<210> SEQ ID NO 54
<211> LENGTH: 31
<212> TYPE: DNA
<213> ORGANISM: Artificial Sequence
<220> FEATURE:
<223> OTHER INFORMATION: Description of Artificial Sequence:PCR Primer

<400> SEQUENCE: 54
ctcgagctct catctttcca gatagcactt c                                      31

<210> SEQ ID NO 55
<211> LENGTH: 41
<212> TYPE: DNA
<213> ORGANISM: Artificial Sequence
<220> FEATURE:
<223> OTHER INFORMATION: Description of Artificial Sequence:PCR Primer

<400> SEQUENCE: 55
ctcccatggg ctttaacaac aagatgttgg ccttggccgc c                           41

<210> SEQ ID NO 56
<211> LENGTH: 48
<212> TYPE: DNA
<213> ORGANISM: Artificial Sequence
<220> FEATURE:
```

-continued

<223> OTHER INFORMATION: Description of Artificial Sequence:PCR Primer

<400> SEQUENCE: 56
actaccagga ctaggaccac taccgttttt gcagcccatc aactccgg         48

<210> SEQ ID NO 57
<211> LENGTH: 18
<212> TYPE: DNA
<213> ORGANISM: Artificial Sequence
<220> FEATURE:
<223> OTHER INFORMATION: Description of Artificial Sequence:PCR Primer

<400> SEQUENCE: 57
ctccatatgg cgccgctg         18

<210> SEQ ID NO 58
<211> LENGTH: 19
<212> TYPE: DNA
<213> ORGANISM: Artificial Sequence
<220> FEATURE:
<223> OTHER INFORMATION: Description of Artificial Sequence:PCR Primer

<400> SEQUENCE: 58
ctcgagctct caaaatttc         19

<210> SEQ ID NO 59
<211> LENGTH: 18
<212> TYPE: DNA
<213> ORGANISM: Artificial Sequence
<220> FEATURE:
<223> OTHER INFORMATION: Description of Artificial Sequence:PCR Primer

<400> SEQUENCE: 59
ctccatatgg cgccgctg         18

<210> SEQ ID NO 60
<211> LENGTH: 18
<212> TYPE: DNA
<213> ORGANISM: Artificial Sequence
<220> FEATURE:
<223> OTHER INFORMATION: Description of Artificial Sequence:PCR Primer

<400> SEQUENCE: 60
ctcgagctct catctttc         18

<210> SEQ ID NO 61
<211> LENGTH: 18
<212> TYPE: DNA
<213> ORGANISM: Artificial Sequence
<220> FEATURE:
<223> OTHER INFORMATION: Description of Artificial Sequence:PCR Primer

<400> SEQUENCE: 61
ctccatatgg aatttgat         18

<210> SEQ ID NO 62
<211> LENGTH: 18
<212> TYPE: DNA
<213> ORGANISM: Artificial Sequence
<220> FEATURE:
<223> OTHER INFORMATION: Description of Artificial Sequence:PCR Primer

<400> SEQUENCE: 62
ctcgagctct cagttgct         18

```
<210> SEQ ID NO 63
<211> LENGTH: 18
<212> TYPE: DNA
<213> ORGANISM: Artificial Sequence
<220> FEATURE:
<223> OTHER INFORMATION: Description of Artificial Sequence:PCR Primer

<400> SEQUENCE: 63
ctccatatgt ccaggcat                                                  18

<210> SEQ ID NO 64
<211> LENGTH: 18
<212> TYPE: DNA
<213> ORGANISM: Artificial Sequence
<220> FEATURE:
<223> OTHER INFORMATION: Description of Artificial Sequence:PCR Primer

<400> SEQUENCE: 64
ctcgagctct cagttgct                                                  18

<210> SEQ ID NO 65
<211> LENGTH: 18
<212> TYPE: DNA
<213> ORGANISM: Artificial Sequence
<220> FEATURE:
<223> OTHER INFORMATION: Description of Artificial Sequence:PCR Primer

<400> SEQUENCE: 65
ctcccatggg ctttaaca                                                  18

<210> SEQ ID NO 66
<211> LENGTH: 18
<212> TYPE: DNA
<213> ORGANISM: Artificial Sequence
<220> FEATURE:
<223> OTHER INFORMATION: Description of Artificial Sequence:PCR Primer

<400> SEQUENCE: 66
ctcgagctct catctttc                                                  18

<210> SEQ ID NO 67
<211> LENGTH: 18
<212> TYPE: DNA
<213> ORGANISM: Artificial Sequence
<220> FEATURE:
<223> OTHER INFORMATION: Description of Artificial Sequence:PCR Primer

<400> SEQUENCE: 67
ctcccatggg ctttaaca                                                  18

<210> SEQ ID NO 68
<211> LENGTH: 19
<212> TYPE: DNA
<213> ORGANISM: Artificial Sequence
<220> FEATURE:
<223> OTHER INFORMATION: Description of Artificial Sequence:PCR Primer

<400> SEQUENCE: 68
ctcgagctct caaaatttc                                                 19

<210> SEQ ID NO 69
<211> LENGTH: 30
<212> TYPE: DNA
<213> ORGANISM: Artificial Sequence
<220> FEATURE:
<223> OTHER INFORMATION: Description of Artificial Sequence:PCR Primer
```

<400> SEQUENCE: 69
ctccatatgg gggggtatgg cggagttaag                                30

<210> SEQ ID NO 70
<211> LENGTH: 48
<212> TYPE: DNA
<213> ORGANISM: Artificial Sequence
<220> FEATURE:
<223> OTHER INFORMATION: Description of Artificial Sequence:PCR Primer

<400> SEQUENCE: 70
actaccagga ctaggaccac tacccccctt catgctaccc aggggag              48

<210> SEQ ID NO 71
<211> LENGTH: 48
<212> TYPE: DNA
<213> ORGANISM: Artificial Sequence
<220> FEATURE:
<223> OTHER INFORMATION: Description of Artificial Sequence:PCR Primer

<400> SEQUENCE: 71
ggtagtggtc ctagtcctgg tagtatgggg gggtatggcg gagttaag             48

<210> SEQ ID NO 72
<211> LENGTH: 33
<212> TYPE: DNA
<213> ORGANISM: Artificial Sequence
<220> FEATURE:
<223> OTHER INFORMATION: Description of Artificial Sequence:PCR Primer

<400> SEQUENCE: 72
ctcgtcgact caccccttca tgctacccag ggg                             33

<210> SEQ ID NO 73
<211> LENGTH: 42
<212> TYPE: DNA
<213> ORGANISM: Artificial Sequence
<220> FEATURE:
<223> OTHER INFORMATION: Description of Artificial Sequence:PCR Primer

<400> SEQUENCE: 73
ctccatatgc gctttaacaa caagatgttg gccttggccg cc                   42

<210> SEQ ID NO 74
<211> LENGTH: 48
<212> TYPE: DNA
<213> ORGANISM: Artificial Sequence
<220> FEATURE:
<223> OTHER INFORMATION: Description of Artificial Sequence:PCR Primer

<400> SEQUENCE: 74
actaccagga ctaggaccac taccgttttt gcagcccatc aactccgg             48

<210> SEQ ID NO 75
<211> LENGTH: 24
<212> TYPE: DNA
<213> ORGANISM: Artificial Sequence
<220> FEATURE:
<223> OTHER INFORMATION: Description of Artificial Sequence:PCR Primer

<400> SEQUENCE: 75
ctccatatgg cgccgctgct ggag                                       24

<210> SEQ ID NO 76
<211> LENGTH: 42

```
<212> TYPE: DNA
<213> ORGANISM: Artificial Sequence
<220> FEATURE:
<223> OTHER INFORMATION: Description of Artificial Sequence:PCR Primer

<400> SEQUENCE: 76
ggtagtggtc ctagtcctgg tagtgttgct ttctaggacc ag                           42

<210> SEQ ID NO 77
<211> LENGTH: 42
<212> TYPE: DNA
<213> ORGANISM: Artificial Sequence
<220> FEATURE:
<223> OTHER INFORMATION: Description of Artificial Sequence:PCR Primer

<400> SEQUENCE: 77
actaccagga ctaggaccac taccatggcg ccgctgctgg ag                           42

<210> SEQ ID NO 78
<211> LENGTH: 30
<212> TYPE: DNA
<213> ORGANISM: Artificial Sequence
<220> FEATURE:
<223> OTHER INFORMATION: Description of Artificial Sequence:PCR Primer

<400> SEQUENCE: 78
ctcgtcgact cagttgcttt ctaggaccag                                         30

<210> SEQ ID NO 79
<211> LENGTH: 30
<212> TYPE: DNA
<213> ORGANISM: Artificial Sequence
<220> FEATURE:
<223> OTHER INFORMATION: Description of Artificial Sequence:PCR Primer

<400> SEQUENCE: 79
ctccatatgg gggggtatgg cggagttaag                                         30

<210> SEQ ID NO 80
<211> LENGTH: 34
<212> TYPE: DNA
<213> ORGANISM: Artificial Sequence
<220> FEATURE:
<223> OTHER INFORMATION: Description of Artificial Sequence:PCR Primer

<400> SEQUENCE: 80
ctcgtcgact cagttgcttt ctaggaccag ttcc                                    34

<210> SEQ ID NO 81
<211> LENGTH: 27
<212> TYPE: DNA
<213> ORGANISM: Artificial Sequence
<220> FEATURE:
<223> OTHER INFORMATION: Description of Artificial Sequence:PCR Primer

<400> SEQUENCE: 81
ctccatatgg cgccgctgct ggagtac                                            27

<210> SEQ ID NO 82
<211> LENGTH: 33
<212> TYPE: DNA
<213> ORGANISM: Artificial Sequence
<220> FEATURE:
<223> OTHER INFORMATION: Description of Artificial Sequence:PCR Primer

<400> SEQUENCE: 82
```
ctcgtcgact caccccttca tgctacccag ggg                             33

<210> SEQ ID NO 83
<211> LENGTH: 43
<212> TYPE: DNA
<213> ORGANISM: Artificial Sequence
<220> FEATURE:
<223> OTHER INFORMATION: Description of Artificial Sequence:PCR Primer

<400> SEQUENCE: 83
ctccatatgc gctttaacaa caagatgttg gccttggccg ccc                  43

<210> SEQ ID NO 84
<211> LENGTH: 33
<212> TYPE: DNA
<213> ORGANISM: Artificial Sequence
<220> FEATURE:
<223> OTHER INFORMATION: Description of Artificial Sequence:PCR Primer

<400> SEQUENCE: 84
ctcgtcgact caccccttca tgctacccag ggg                             33

<210> SEQ ID NO 85
<211> LENGTH: 22
<212> TYPE: DNA
<213> ORGANISM: Artificial Sequence
<220> FEATURE:
<223> OTHER INFORMATION: Description of Artificial Sequence:PCR Primer

<400> SEQUENCE: 85
ctccatatgg cggcggccga cg                                         22

<210> SEQ ID NO 86
<211> LENGTH: 48
<212> TYPE: DNA
<213> ORGANISM: Artificial Sequence
<220> FEATURE:
<223> OTHER INFORMATION: Description of Artificial Sequence:PCR Primer

<400> SEQUENCE: 86
actaccagga ctaggaccac taccgttcat ggccacacat agtacaag             48

<210> SEQ ID NO 87
<211> LENGTH: 40
<212> TYPE: DNA
<213> ORGANISM: Artificial Sequence
<220> FEATURE:
<223> OTHER INFORMATION: Description of Artificial Sequence:PCR Primer

<400> SEQUENCE: 87
ggtagtggtc ctagtcctgg tagtatggcg gcggccgacg                      40

<210> SEQ ID NO 88
<211> LENGTH: 36
<212> TYPE: DNA
<213> ORGANISM: Artificial Sequence
<220> FEATURE:
<223> OTHER INFORMATION: Description of Artificial Sequence:PCR Primer

<400> SEQUENCE: 88
ctcgagctct cagttcatgg ccacacatag tacaag                          36

<210> SEQ ID NO 89
<211> LENGTH: 42
<212> TYPE: DNA
<213> ORGANISM: Artificial Sequence

```
<220> FEATURE:
<223> OTHER INFORMATION: Description of Artificial Sequence:PCR Primer

<400> SEQUENCE: 89
ctccatatgc gctttaacaa caagatgttg gccttggccg cc                              42

<210> SEQ ID NO 90
<211> LENGTH: 48
<212> TYPE: DNA
<213> ORGANISM: Artificial Sequence
<220> FEATURE:
<223> OTHER INFORMATION: Description of Artificial Sequence:PCR Primer

<400> SEQUENCE: 90
actaccagga ctaggaccac taccgttttt gcagcccatc aactccgg                        48

<210> SEQ ID NO 91
<211> LENGTH: 24
<212> TYPE: DNA
<213> ORGANISM: Artificial Sequence
<220> FEATURE:
<223> OTHER INFORMATION: Description of Artificial Sequence:PCR Primer

<400> SEQUENCE: 91
ctccatatgg cgccgctgct ggag                                                  24

<210> SEQ ID NO 92
<211> LENGTH: 42
<212> TYPE: DNA
<213> ORGANISM: Artificial Sequence
<220> FEATURE:
<223> OTHER INFORMATION: Description of Artificial Sequence:PCR Primer

<400> SEQUENCE: 92
ggtagtggtc ctagtcctgg tagtgttgct ttctaggacc ag                              42

<210> SEQ ID NO 93
<211> LENGTH: 42
<212> TYPE: DNA
<213> ORGANISM: Artificial Sequence
<220> FEATURE:
<223> OTHER INFORMATION: Description of Artificial Sequence:PCR Primer

<400> SEQUENCE: 93
actaccagga ctaggaccac taccatggcg ccgctgctgg ag                              42

<210> SEQ ID NO 94
<211> LENGTH: 30
<212> TYPE: DNA
<213> ORGANISM: Artificial Sequence
<220> FEATURE:
<223> OTHER INFORMATION: Description of Artificial Sequence:PCR Primer

<400> SEQUENCE: 94
ctcgagctct cagttgcttt ctaggaccag                                            30

<210> SEQ ID NO 95
<211> LENGTH: 22
<212> TYPE: DNA
<213> ORGANISM: Artificial Sequence
<220> FEATURE:
<223> OTHER INFORMATION: Description of Artificial Sequence:PCR Primer

<400> SEQUENCE: 95
ctccatatgg cggcggccga cg                                                    22
```

-continued

```
<210> SEQ ID NO 96
<211> LENGTH: 34
<212> TYPE: DNA
<213> ORGANISM: Artificial Sequence
<220> FEATURE:
<223> OTHER INFORMATION: Description of Artificial Sequence:PCR Primer

<400> SEQUENCE: 96
ctcgagctct cagttgcttt ctaggaccag ttcc                                    34

<210> SEQ ID NO 97
<211> LENGTH: 27
<212> TYPE: DNA
<213> ORGANISM: Artificial Sequence
<220> FEATURE:
<223> OTHER INFORMATION: Description of Artificial Sequence:PCR Primer

<400> SEQUENCE: 97
ctccatatgg cgccgctgct ggagtac                                            27

<210> SEQ ID NO 98
<211> LENGTH: 36
<212> TYPE: DNA
<213> ORGANISM: Artificial Sequence
<220> FEATURE:
<223> OTHER INFORMATION: Description of Artificial Sequence:PCR Primer

<400> SEQUENCE: 98
ctcgagctct cagttcatgg ccacacatag tacaag                                  36

<210> SEQ ID NO 99
<211> LENGTH: 30
<212> TYPE: DNA
<213> ORGANISM: Artificial Sequence
<220> FEATURE:
<223> OTHER INFORMATION: Description of Artificial Sequence:PCR Primer

<400> SEQUENCE: 99
ctccatatgc gctttaacaa caagatgttg                                         30

<210> SEQ ID NO 100
<211> LENGTH: 36
<212> TYPE: DNA
<213> ORGANISM: Artificial Sequence
<220> FEATURE:
<223> OTHER INFORMATION: Description of Artificial Sequence:PCR Primer

<400> SEQUENCE: 100
ctcgagctct cagttcatgg ccacacatag tacaag                                  36

<210> SEQ ID NO 101
<211> LENGTH: 940
<212> TYPE: PRT
<213> ORGANISM: Escherichia coli

<400> SEQUENCE: 101

Met Asp Lys Ile Glu Val Arg Gly Ala Arg Thr His Asn Leu Lys Asn
 1               5                  10                  15

Ile Asn Leu Val Ile Pro Arg Asp Lys Leu Ile Val Val Thr Gly Leu
            20                  25                  30

Ser Gly Ser Gly Lys Ser Ser Leu Ala Phe Asp Thr Leu Tyr Ala Glu
        35                  40                  45

Gly Gln Arg Arg Tyr Val Glu Ser Leu Ser Ala Tyr Ala Arg Gln Phe
    50                  55                  60
```

```
Leu Ser Leu Met Glu Lys Pro Asp Val Asp His Ile Glu Gly Leu Ser
 65                  70                  75                  80

Pro Ala Ile Ser Ile Glu Gln Lys Ser Thr Ser His Asn Pro Arg Ser
                 85                  90                  95

Thr Val Gly Thr Ile Thr Glu Ile His Asp Tyr Leu Arg Leu Leu Phe
            100                 105                 110

Ala Arg Val Gly Glu Pro Arg Cys Pro Asp His Asp Val Pro Leu Ala
        115                 120                 125

Ala Gln Thr Val Ser Gln Met Val Asp Asn Val Leu Ser Gln Pro Glu
    130                 135                 140

Gly Lys Arg Leu Met Leu Leu Ala Pro Ile Ile Lys Glu Arg Lys Gly
145                 150                 155                 160

Glu His Thr Lys Thr Leu Glu Asn Leu Ala Ser Gln Gly Tyr Ile Arg
                165                 170                 175

Ala Arg Ile Asp Gly Glu Val Cys Asp Leu Ser Asp Pro Pro Lys Leu
            180                 185                 190

Glu Leu Gln Lys Lys His Thr Ile Glu Val Val Asp Arg Phe Lys
        195                 200                 205

Val Arg Asp Asp Leu Thr Gln Arg Leu Ala Glu Ser Phe Glu Thr Ala
210                 215                 220

Leu Glu Leu Ser Gly Gly Thr Ala Val Val Ala Asp Met Asp Asp Pro
225                 230                 235                 240

Lys Ala Glu Glu Leu Leu Phe Ser Ala Asn Phe Ala Cys Pro Ile Cys
                245                 250                 255

Gly Tyr Ser Met Arg Glu Leu Glu Pro Arg Leu Phe Ser Phe Asn Asn
            260                 265                 270

Pro Ala Gly Ala Cys Pro Thr Cys Asp Gly Leu Gly Val Gln Gln Tyr
        275                 280                 285

Phe Asp Pro Asp Arg Val Ile Gln Asn Pro Glu Leu Ser Leu Ala Gly
    290                 295                 300

Gly Ala Ile Arg Gly Trp Asp Arg Arg Asn Phe Tyr Tyr Phe Gln Met
305                 310                 315                 320

Leu Lys Ser Leu Ala Asp His Tyr Lys Phe Asp Val Glu Ala Pro Trp
                325                 330                 335

Gly Ser Leu Ser Ala Asn Val His Lys Val Val Leu Tyr Gly Ser Gly
            340                 345                 350

Lys Glu Asn Ile Glu Phe Lys Tyr Met Asn Asp Arg Gly Asp Thr Ser
        355                 360                 365

Ile Arg Arg His Pro Phe Glu Gly Val Leu His Asn Met Glu Arg Arg
    370                 375                 380

Tyr Lys Glu Thr Glu Ser Ser Ala Val Arg Glu Glu Leu Ala Lys Phe
385                 390                 395                 400

Ile Ser Asn Arg Pro Cys Ala Ser Cys Glu Gly Thr Arg Leu Arg Arg
                405                 410                 415

Glu Ala Arg His Val Tyr Val Glu Asn Thr Pro Leu Pro Ala Ile Ser
            420                 425                 430

Asp Met Ser Ile Gly His Ala Met Glu Phe Phe Asn Asn Leu Lys Leu
        435                 440                 445

Ala Gly Gln Arg Ala Lys Ile Ala Glu Lys Ile Leu Lys Glu Ile Gly
    450                 455                 460

Asp Arg Leu Lys Phe Leu Val Asn Val Gly Leu Asn Tyr Leu Thr Leu
465                 470                 475                 480
```

```
Ser Arg Ser Ala Glu Thr Leu Ser Gly Gly Glu Ala Gln Arg Ile Arg
            485                 490                 495

Leu Ala Ser Gln Ile Gly Ala Gly Leu Val Gly Val Met Tyr Val Leu
            500                 505                 510

Asp Glu Pro Ser Ile Gly Leu His Gln Arg Asp Asn Glu Arg Leu Leu
            515                 520                 525

Gly Thr Leu Ile His Leu Arg Asp Leu Gly Asn Thr Val Ile Val Val
            530                 535                 540

Glu His Asp Glu Asp Ala Ile Arg Ala Ala Asp His Val Ile Asp Ile
545                 550                 555                 560

Gly Pro Gly Ala Gly Val His Gly Gly Glu Val Val Ala Glu Gly Pro
                565                 570                 575

Leu Glu Ala Ile Met Ala Val Pro Glu Ser Leu Thr Gly Gln Tyr Met
            580                 585                 590

Ser Gly Lys Arg Lys Ile Glu Val Pro Lys Lys Arg Val Pro Ala Asn
            595                 600                 605

Pro Glu Lys Val Leu Lys Leu Thr Gly Ala Arg Gly Asn Asn Leu Lys
            610                 615                 620

Asp Val Thr Leu Thr Leu Pro Val Gly Leu Phe Thr Cys Ile Thr Gly
625                 630                 635                 640

Val Ser Gly Ser Gly Lys Ser Thr Leu Ile Asn Asp Thr Leu Phe Pro
                645                 650                 655

Ile Ala Gln Arg Gln Leu Asn Gly Ala Thr Ile Ala Glu Pro Ala Pro
            660                 665                 670

Tyr Arg Asp Ile Gln Gly Leu Glu His Phe Asp Lys Val Ile Asp Ile
            675                 680                 685

Asp Gln Ser Pro Ile Gly Arg Thr Pro Arg Ser Asn Pro Ala Thr Tyr
            690                 695                 700

Thr Gly Val Phe Thr Pro Val Arg Glu Leu Phe Ala Gly Val Pro Glu
705                 710                 715                 720

Ser Arg Ala Arg Gly Tyr Thr Pro Gly Arg Phe Ser Phe Asn Val Arg
                725                 730                 735

Gly Gly Arg Cys Glu Ala Cys Gln Gly Asp Gly Val Ile Lys Val Glu
            740                 745                 750

Met His Phe Leu Pro Asp Ile Tyr Val Pro Cys Asp Gln Cys Lys Gly
            755                 760                 765

Lys Arg Tyr Asn Arg Glu Thr Leu Glu Ile Lys Tyr Lys Gly Lys Thr
            770                 775                 780

Ile His Glu Val Leu Asp Met Thr Ile Glu Glu Ala Arg Glu Phe Phe
785                 790                 795                 800

Asp Ala Val Pro Ala Leu Ala Arg Lys Leu Gln Thr Leu Met Asp Val
                805                 810                 815

Gly Leu Thr Tyr Ile Arg Leu Gly Gln Ser Ala Thr Thr Leu Ser Gly
            820                 825                 830

Gly Glu Ala Gln Arg Val Lys Leu Ala Arg Glu Leu Ser Lys Arg Gly
            835                 840                 845

Thr Gly Gln Thr Leu Tyr Ile Leu Asp Glu Pro Thr Thr Gly Leu His
            850                 855                 860

Phe Ala Asp Ile Gln Gln Leu Leu Asp Val Leu His Lys Leu Arg Asp
865                 870                 875                 880

Gln Gly Asn Thr Ile Val Val Ile Glu His Asn Leu Asp Val Ile Lys
                885                 890                 895

Thr Ala Asp Trp Ile Val Asp Leu Gly Pro Glu Gly Gly Ser Gly Gly
```

```
                900            905             910
Gly Glu Ile Leu Val Ser Gly Thr Pro Glu Thr Val Ala Glu Cys Glu
            915             920             925

Ala Ser His Thr Ala Arg Phe Leu Lys Pro Met Leu
        930             935             940

<210> SEQ ID NO 102
<211> LENGTH: 3205
<212> TYPE: DNA
<213> ORGANISM: Escherchia coli

<400> SEQUENCE: 102
atgttcgtgt ctcctgaaaa aaatcgttct gaataagtgt aaacgcgcga ttgtaccatt      60
accaatagcg cttttactat gttgtgacct cggttccgcg aaacaaacct ggccagacat     120
tgttacacaa cactccgggt aatgcattcc aatactgtat attcattcag gtcaatttgt     180
gtcataatta accgtttgtg atcgccggta gcaccatgcc accgggcaaa aaagcgttta     240
atccgggaaa ggtgaatgga taagatcgaa gttcggggcg cccgcaccca taatctcaaa     300
aacatcaacc tcgttatccc ccgcgacaag ctcattgtcg tgaccgggct ttcgggttct     360
ggcaaatcct cgctcgcttt cgacacctta tatgccgaag gcagcgccg ttacgttgaa       420
tccctttccg cctacgcgcg gcagtttctg tcactgatga aaaagccgga cgtcgatcat     480
attgaggggc tttctcctgc catctcaatt gagcagaaat cgacgtctca taacccgcgt     540
tctacggtgg ggacaatcac cgaaatccac gactatttgc gtttgttatt cgcccgcgtt     600
ggcgagccgc gctgtccgga ccacgacgtc ccgctggcgg cgcaaaccgt cagccagatg     660
gtggataacg tgctgtcgca gccggaaggc aagcgtctga tgctactcgc gccaatcatt     720
aaagagcgca aggcgaaca caccaaaacg ctggagaacc tggcaagcca gggctacatc     780
cgtgctcgta ttgatggcga agtctgcgat ctttccgatc cgccaaaact ggaactgcaa     840
aagaaacata ccattgaagt ggtggttgat cgcttcaagg tgcgtgacga tcttacccaa     900
cgtcttgccg agtcatttga aaccgcgctg gagctttccg gtggtaccgc ggtagtggcg     960
gatatggacg acccgaaagc ggaagagctg ctgttctccg ccaacttcgc ctgcccaatt    1020
tgcggctaca gtatgcgtga actggagccg cgactgtttt cgtttaacaa cccggcgggg    1080
gcctgcccga cctgcgacgg ccttggcgta cagcaatatt tcgatcctga tcgagtgatc    1140
cagaatccgg aactgtcgct ggctggtggt gcgatccgtg gctgggatcg ccgcaacttc    1200
tattatttcc agatgctgaa atcgctggca gatcactata agttcgacgt cgaagcgccg    1260
tggggcagcc tgagcgcgaa cgtgcataaa gtggtgttgt acggttctgg caaagaaaac    1320
attgaattca atacatgaa cgatcgtggc gatacctcca ttcgtcgtca tccgttcgaa     1380
ggcgtgctgc ataatatgga cgccgctat aaagagacgg aatccagcgc ggtacgcgaa      1440
gaattagcca agtttatcag taatcgtccg tgcgccagct gcgaagggac gcgtctgcgt    1500
cgggaagcgc gccacgtgta tgtcgagaat acgccgctgc ctgctatctc gacatgagc    1560
attggtcatg cgatggaatt cttcaacaat ctcaaactcg caggtcagcg ggcgaagatt    1620
gcagaaaaaa tccttaaaga gatcggcgat cgtctgaaat tcctcgttaa cgtcggcctg    1680
aattacctga cgctttcccg ctcggcagaa acgctttctg gcggtgaagc acagcgtatc    1740
cgtctggcga gccagattgg tgcgggcctg gttggcgtta tgtacgtgct ggacgagccg    1800
tctatcggcc tgcaccagcg tgataacgag cgccgttgg gtacgcttat ccatctgcgc     1860
gatctcggta ataccgtgat tgtggtggag cacgacgaag acgcaattcg cgccgctgac    1920
```

```
catgtgatcg acattggccc gggcgcaggt gttcacggcg gtgaagtggt cgcagaaggt   1980
ccgctggaag cgattatggc ggtgccggag tcgttgaccg ggcagtacat gagcggcaaa   2040
cgcaagattg aagtgccgaa gaaacgcgtt ccggcgaatc cggaaaaagt gctgaagctg   2100
acaggcgcac gcggcaacaa cctgaaggac gtgacgctga cgctgccggt gggtctgttt   2160
acctgcatca ccggggtttc aggttccggt aaatcgacgt gattaacga cacactgttc   2220 ccgattgccc aacgccagtt gaatggggcg accatcgccg aaccagcacc gtatcgcgat   2280
attcaggggc tggagcattt cgataaagtg atcgatatcg accaaagccc aattggtcgt   2340
actccacgtt ctaacccggc gacctatacc ggcgtgttta cgcctgtgcg cgaactgttt   2400
gcgggcgtac cggaatcccg tgcgcgcggc tatacgccgg gacgtttcag ctttaacgtt   2460
cgtggcggac gctgcgaggc ctgtcaggtg gatggcgtga tcaaagtgga gatgcacttc   2520
ctgccggata tctacgtgcc gtgcgaccag tgcaaaggta acgctataa ccgtgaaacg   2580 ctggagatta agtacaaagg caaaaccatc cacgaagtgc tggatatgac catcgaagag   2640
gcgcgtgagt tctttgatgc cgtacctgca ctggcgcgta agctgcaaac gttgatggac   2700
gttggcctga cgtacattcg actggggcag tccgcaacca cccttcagg cggtgaagcc   2760 cagcgcgtga agctggcgcg tgaactgtca aaacgcggca ccgggcagac gctgtatatt   2820
ctcgacgagc cgaccaccgg tctgcacttc gccgatattc agcaactgct cgacgtactg   2880
cataaactgc gcgatcaggg caacaccatt gtggtgattg agcacaatct cgacgtgatc   2940
aaaaccgctg actggattgt cgacctggga ccagaaggcg gcagtggtgg cggcgagatc   3000
ctcgtctccg gtacgccaga aaccgtcgcg gagtgcgaag catcacacac ggcacgcttc   3060
cttaagccga tgctgtaatc gttaaggccg cttctgagc ggccttttcc tttcagagtt   3120
gcaccagcaa tttacgtttt tcttccggca gtaaattcac cgcctgctga taagacgcat   3180
ccaccagata atagatttgc gaatc                                        3205
```

<210> SEQ ID NO 103
<211> LENGTH: 401
<212> TYPE: PRT
<213> ORGANISM: Escherichia coli

<400> SEQUENCE: 103

```
Met Ser Lys Lys Asn Ser Ala Lys Ser Gly Asp Ala Arg Arg Gly Asp
 1               5                  10                  15

Gly Ala His Thr Gly Val Thr Gly Ser Gly Lys Thr Thr Ala Asn Val
            20                  25                  30

Ala Asp Arg Thr Met Val Ala Asn Lys Thr Ala Ala Tyr Gly Met Lys
        35                  40                  45

Asn Ala Val Tyr Val Ser Tyr Tyr Asp Tyr Tyr Ala Tyr Val Ser Ser
    50                  55                  60

Asp Thr Lys Asp Ala Ser Val Asn His Met Arg Ser Ala Thr Lys Ala
65                  70                  75                  80

Met Arg Arg Asp Val Val Val Ala Ser Val Ser Ala Tyr Gly Gly
                85                  90                  95

Asp Asp Tyr Lys Met Met His Thr Val Gly Met Asp Arg Ala Arg Arg
               100                 105                 110

Ala Tyr Ala Arg Asn Asp Ala Arg Gly Thr Arg Val Arg Gly Val Asp
           115                 120                 125

Ala Ser Asp Asp Ala Arg Val Asp Val Arg Ser Asp Thr Gly Val Ser
       130                 135                 140
```

```
Thr Arg Thr Tyr Lys Thr His Tyr Val Thr Arg Val Ala Met Lys
145                 150                 155                 160

Ala Ala Arg Arg Lys Val Asn Asn Lys Arg Thr Arg Thr Asp Met Met
            165                 170                 175

Asn Gly Tyr Cys Ser Gly Asn Tyr Ser Arg Ser Gly Arg Gly Gly Thr
            180                 185                 190

Asp Tyr Ala Asp Gly Val Val Asp Ser His Val Thr Gly Gly Met Tyr
            195                 200                 205

Arg Gly Asp Arg Ala Arg Lys Thr Val Tyr Gly Arg Ser Ala Asp Asn
        210                 215                 220

Arg Lys Ala Ala Thr Tyr Val Ser Ala Thr Gly Asn Tyr Lys Ser Gly
225                 230                 235                 240

Gly Asp Val Val Asp Val Val Arg Thr Gly Asp Val Arg Val Ala Thr
                245                 250                 255

Val Asp Asp Ser Arg Arg Ala Ala Asn Arg Val Val Thr Thr Thr Lys
            260                 265                 270

Arg Met Ala Asp Thr Tyr His Gly Arg Val Arg Tyr Arg Ser Asp Asp
        275                 280                 285

Thr Val Arg Met Arg Asp Arg Gly Asp Val Val Gly Asn Arg Gly Asp
290                 295                 300

Met Val Ser Val Ala Asp Ala Asp Lys Gly Arg Ser Arg Ser Thr Gly
305                 310                 315                 320

Arg Ala Ala Arg Asn Val Asn Gly Lys Ala Tyr Gly Asp Lys Thr Ser
                325                 330                 335

Met Ala Lys Ala Gly Thr Arg Arg Lys Lys Tyr Asn His Gly Thr
            340                 345                 350

Gly Asn Lys Lys Val Val Asp Ala Gly Asn Ala Lys Thr Lys Ala Lys
            355                 360                 365

Gly Arg Gly Lys Ser Arg Val Asp Asn Val Met Asp Met Ser Lys Ala
        370                 375                 380

Lys His Gly Met Met His Ala Asn Ala Ala Arg Asp His Arg Ala Ala
385                 390                 395                 400

Ser
```

<210> SEQ ID NO 104
<211> LENGTH: 2605
<212> TYPE: DNA
<213> ORGANISM: Escherchia coli

<400> SEQUENCE: 104

```
cggcggggga tagggctgg  acacagttat ccactattcc tgtggataac catgtgtatt    60
agagttagaa aacacgaggc aagcgagaga atacgcggct tgcacgcgaa ttggcgttaa   120
agacggctca aagaaatatc ttttattttt taaccggtta gataaatgca atggcagtca   180
ctgaacaggc atctcttgcc ataaaactgt catcactcat cttgacaaat gttaaaaaag   240
ccgttgcttt ggggataacc cggtaaggcc ggagttttat ctcgccacag agtaaatttt   300
gctcatgatt gacagcggag tttacgctgt atcagaaata ttatggtgat gaactgtttt   360
tttatccagt ataatttgtt gggataatta agtacgacga gtaaaattac atacctgccc   420
gcccaactcc ttcaggtagc gactcatgag taaaccgttc aaactgaatt ccgctttaa    480
accttctggc gatcagccag aggcgattcg acgtctcgaa gagggggtgg aagatggcct   540
ggcgcaccag acgttacttg gcgtgactgg ctcagggaaa accttcacca ttgccaatgt   600
```

-continued

```
cattgctgac cttcagcgcc caaccatggt acttgcgccc aacaaaacgc tggcggccca    660
gctgtatggc gaaatgaaag agttcttccc ggaaaacgcg gtggaatatt cgtttccta    720
ctacgactac tatcagccgg aagcctatgt accgagttcc gacactttca ttgagaaaga    780
tgcctcggtt aacgaacata ttgagcagat gcgtttgtcc gccaccaaag cgatgctgga    840
gcggcgtgat gtggttgtgg tggcgtctgt ttccgcgatt tatggtctgg gcgatcctga    900
tttatatctc aagatgatgc tccatctcac ggtcggtatg attatcgatc agcgcgcgat    960
tctgcgccga ctggcggagc tgcaatacgc tcgtaatgat caagcattcc agcgtggtac   1020
tttccgcgtt cgtggcgagg tgatagatat cttcccggca gaatcggatg acattgcact   1080
tcgcgtggaa ctgttttgacg aggaagtgga acgattgtcg ttatttgacc cgctgaccgg   1140
gcagattgtt tccactattc cacgttttac catctacccg aaaacgcact acgtcacacc   1200
gcgcgagcgc atcgtacagg cgatggagga gatcaaagaa gagctggccg ccagacgcaa   1260
agtgctgttg gaaaacaaca aactgctgga gagcagcgg ctgacccagc gtacccagtt    1320
tgatctggag atgatgaacg agctgggcta ctgttcgggg attgaaaact actcgcgctt   1380
cctctccggt cgtggaccgg gtgagccacc gccgacgctg tttgattacc tgcctgccga   1440
tgggctgctg gtcgtcgatg aatctcacgt caccattcca caaattggcg gcatgtatcg   1500
cggtgaccgg gcgcgtaaag agacactggt ggagtacggc ttccgcctgc catcagcgct   1560
ggataaccgt ccgcttaagt ttgaagagtt cgaagcatta gcgccgcaaa ccatctatgt   1620
ttcggcgacg ccgggtaatt acgagctgga aaaatccggc ggcgatgtgg tggatcaggt   1680
ggtgcgtcca accggattgc ttgacccgat tatcgaagtg cggccggtgg cgacacaggt   1740
tgatgatctt ctttcggaga ttcgtcagcg agcggcaatt aacgaacgcg tactggtcac   1800
cacactgacc aagcggatgg cggaagatct taccgaatat ctcgaagaac atggcgagcg   1860
cgtgcgttat cttcgctcag atatcgacac cgtcgaacgt atggagatta ccgcgactt   1920
gcgtctgggt gagttcgacg tgctggtagg gatcaactta ctgcgcgaag gtctggatat   1980
gccggaagtg tcgctggtgg cgatcctcga cgctgacaaa gaaggcttcc tgcgttccga   2040
acgttcgttg atccagacca ttggtcgtgc ggcacgtaac gttaacggta aagcgattct   2100
ctacggcgat aagatcaccc catcaatggc gaaagcgatt ggcgaaaccg aacgtcgccg   2160
tgagaaacag cagaagtaca acgaggaaca cggaattacg ccgcaaggct tgaacaagaa   2220
agtggtcgat atcctggcgc tggggcagaa cattgccaaa accaaagcga agggcagagg   2280
aaaatcgcgc ccgattgttg agccggataa tgtgccgatg gatatgtcgc taaagcgtt    2340
gcagcagaaa atccatgagc tggaagggtt gatgatgcaa cacgcgcaga tctggagtt    2400
cgaagaagcg gcgcaaattc gtgaccagtt gcatcagctg cgtgagctgt ttatcgcggc   2460
atcgtaacag gatagcgaag aagactgatg acaaacggaa aacagcctga tgcgctacgc   2520
ttatcaggcc tacattttct ccgcaatata ttgaatttgc gcggtttgta ggccggtaaa   2580
ggcgatcacg ccgcaaatcc ggcat                                          2605
```

<210> SEQ ID NO 105
<211> LENGTH: 218
<212> TYPE: PRT
<213> ORGANISM: Escherichia coli

<400> SEQUENCE: 105

Met Ile Asn Val Leu Leu Val Asp Asp His Glu Leu Val Arg Ala Gly
 1               5                  10                  15

Ile Arg Arg Ile Leu Glu Asp Ile Lys Gly Ile Lys Val Val Gly Glu
                20                  25                  30

Ala Ser Cys Gly Glu Asp Ala Val Lys Trp Cys Arg Thr Asn Ala Val
            35                  40                  45

Asp Val Val Leu Met Asp Met Ser Met Pro Gly Ile Gly Gly Leu Glu
        50                  55                  60

Ala Thr Arg Lys Ile Ala Arg Ser Thr Ala Asp Val Lys Ile Ile Met
65                  70                  75                  80

Leu Thr Val His Thr Glu Asn Pro Leu Pro Ala Lys Val Met Gln Ala
                85                  90                  95

Gly Ala Ala Gly Tyr Leu Ser Lys Gly Ala Ala Pro Gln Glu Val Val
            100                 105                 110

Ser Ala Ile Arg Ser Val Tyr Ser Gly Gln Arg Tyr Ile Ala Ser Asp
        115                 120                 125

Ile Ala Gln Gln Met Ala Leu Ser Gln Ile Glu Pro Glu Lys Thr Glu
130                 135                 140

Ser Pro Phe Ala Ser Leu Ser Glu Arg Glu Leu Gln Ile Met Leu Met
145                 150                 155                 160

Ile Thr Lys Gly Gln Lys Val Asn Glu Ile Ser Glu Gln Leu Asn Leu
                165                 170                 175

Ser Pro Lys Thr Val Asn Ser Tyr Arg Tyr Arg Met Phe Ser Lys Leu
            180                 185                 190

Asn Ile His Gly Asp Val Glu Leu Thr His Leu Ala Ile Arg His Gly
        195                 200                 205

Leu Cys Asn Ala Glu Thr Leu Ser Ser Gln
    210                 215

<210> SEQ ID NO 106
<211> LENGTH: 840
<212> TYPE: DNA
<213> ORGANISM: Escherchia coli

<400> SEQUENCE: 106
cgaatacccc ccattttaa cgtttcaaag ttgcaataaa aaccgctaat atacgaatga     60
ctaactatca gtagcgttat ccctatttct ggagatattc ctttgatcaa cgttctactt    120
gttgatgacc acgaactggt gcgcgcaggg atacgacgca ttctggaaga tataaagggt    180
ataaaagtcg tcggtgaggc atcgtgcggt gaagacgccg ttaagtggtg ccggacaaat    240
gccgttgacg tggtgctaat ggacatgagt atgccgggca ttggcggtct tgaggcgacg    300
cgtaaaatcg cgcgttccac agctgatgtc aaaatcatca tgcttaccgt ccatacagaa    360
aaccctttac cagcgaaagt catgcaggcc ggtgctgcgg gctacctcag caaaggcgcg    420
gctccgcagg aagtcgtgag tgcgattcgt tctgtctatt cagggcagcg ttacattgct    480
tctgacatcg ctcaacaaat ggcgttaagc cagatcgaac cagaaaaaac agaaagccca    540
tttgccagtt tgtctgaacg tgaattgcag attatgctga tgatcaccaa gggccagaag    600
gtcaatgaga tctcagaaca gctcaatctc agtccgaaaa cggtgaacag ctaccgctat    660
cgtatgttca gtaaactaaa cattcatggc gatgttgagc tgactcacct ggcaattcgc    720
catggtctgt gtaatgcgga gacattatca agtcagtgag tgatcagttt gacgcaaaag    780
cgtttttaaa aaccgtaacc agccagccag gcgtttatcg catgtacgat gctggtggta    840